United States Patent
Hayashi et al.

(10) Patent No.: US 11,510,850 B2
(45) Date of Patent: Nov. 29, 2022

(54) MEDICATION SUPPORT APPARATUS

(71) Applicants: Hirotaka Hayashi, Kanagawa (JP); Akira Kojima, Kanagawa (JP); Takuya Morinaga, Tokyo (JP); Norio Kimura, Kanagawa (JP); Wataru Nozaki, Kanagawa (JP)

(72) Inventors: Hirotaka Hayashi, Kanagawa (JP); Akira Kojima, Kanagawa (JP); Takuya Morinaga, Tokyo (JP); Norio Kimura, Kanagawa (JP); Wataru Nozaki, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 15 days.

(21) Appl. No.: 17/326,753

(22) Filed: May 21, 2021

(65) Prior Publication Data

US 2021/0361532 A1    Nov. 25, 2021

(30) Foreign Application Priority Data

May 25, 2020    (JP) .............................. JP2020-090945

(51) Int. Cl.
*G16H 20/13*    (2018.01)
*A61J 7/04*    (2006.01)
(Continued)

(52) U.S. Cl.
CPC ........... *A61J 7/0463* (2015.05); *A61J 7/0069* (2013.01); *A61J 7/0076* (2013.01); *A61J 7/0084* (2013.01);
(Continued)

(58) Field of Classification Search
CPC ... G16H 20/13; G07F 17/0092; G07F 11/165; A61J 7/0069; A61J 7/0463
See application file for complete search history.

(56) References Cited

U.S. PATENT DOCUMENTS 3,627,122 A * 12/1971 Garbe, Jr. ............... A47B 87/02
                                                         206/366
4,019,793 A *  4/1977 Gerding ............... A61G 12/001
                                                         312/249.8
(Continued)

FOREIGN PATENT DOCUMENTS

JP    2017-184877    10/2017
JP    2017-192455    10/2017

*Primary Examiner* — Timothy R Waggoner
(74) *Attorney, Agent, or Firm* — Harness, Dickey & Pierce, P.L.C.

(57) ABSTRACT

A medication support apparatus includes a container, a medicine distribution member, a port, a take-out device, and a transfer device. The container is configured to store one-dose packages of medicines. The medicine distribution member includes a plurality of partitions configured to separately include the one-dose packages of medicines. The medicine distribution member is configured to enter and exit the medication support apparatus through the port. The take-out device is configured to take out a specific one of the one-dose packages of medicines from the container. The transfer device is configured to transfer the specific one of the one-dose packages of medicines taken out from the container. The one-dose packages of medicines are configured to be placed at predetermined positions partitioned by the plurality of partitions in the medicine distribution member.

9 Claims, 59 Drawing Sheets

(51) Int. Cl.
*A61J 7/00* (2006.01)
*G07F 17/00* (2006.01)
(52) U.S. Cl.
CPC ........ *A61J 7/0481* (2013.01); *G07F 17/0092* (2013.01); *G16H 20/13* (2018.01)

(56) References Cited

U.S. PATENT DOCUMENTS

| | | | | |
|---|---|---|---|---|
| 5,046,609 | A * | 9/1991 | Mangini | G09F 3/0288 |
| | | | | 40/310 |
| 5,468,110 | A * | 11/1995 | McDonald | G07F 17/0092 |
| | | | | 414/268 |
| 5,771,657 | A * | 6/1998 | Lasher | B65B 61/20 |
| | | | | 53/493 |
| 6,293,403 | B1 * | 9/2001 | Holmberg | A61J 7/0069 |
| | | | | 206/534 |
| 6,564,945 | B1 * | 5/2003 | Weinstein | A61J 1/03 |
| | | | | 206/459.5 |
| 7,958,701 | B2 * | 6/2011 | Knoth | B65B 5/103 |
| | | | | 221/121 |
| 8,914,146 | B2 * | 12/2014 | Carson | B65D 75/327 |
| | | | | 700/214 |
| 2008/0272138 | A1 * | 11/2008 | Ross | G07F 11/1657 |
| | | | | 705/2 |
| 2009/0188937 | A1 * | 7/2009 | Kim | A61J 7/0069 |
| | | | | 221/312 B |
| 2010/0172724 | A1 * | 7/2010 | Hawkes | G06F 17/00 |
| | | | | 414/807 |
| 2012/0296592 | A1 * | 11/2012 | Luciano, Jr | A61J 7/0084 |
| | | | | 702/84 |
| 2019/0102965 | A1 * | 4/2019 | Greyshock | G07F 11/60 |
| 2020/0226869 | A1 * | 7/2020 | Cohen-Daniel | G07F 17/0092 |

* cited by examiner

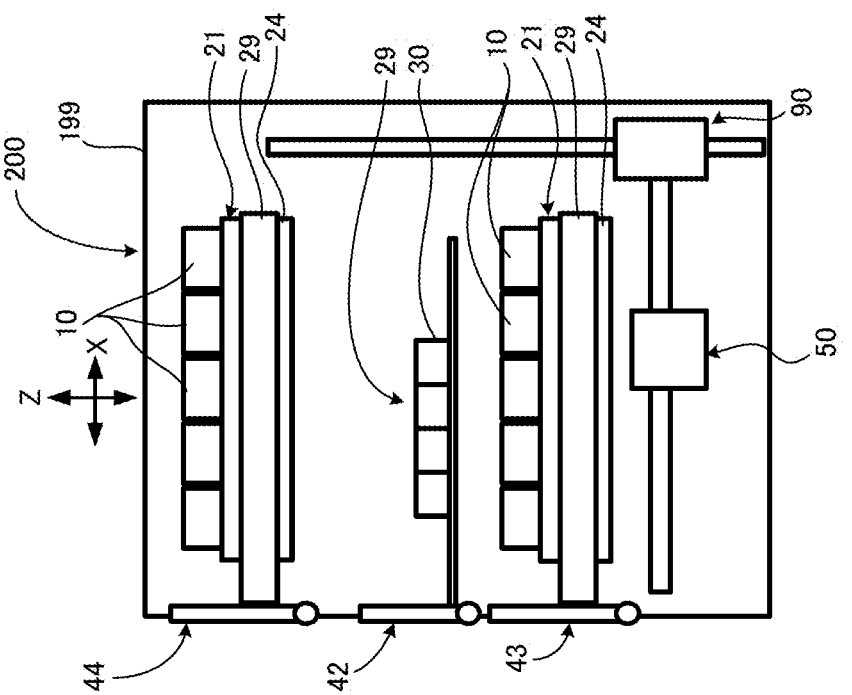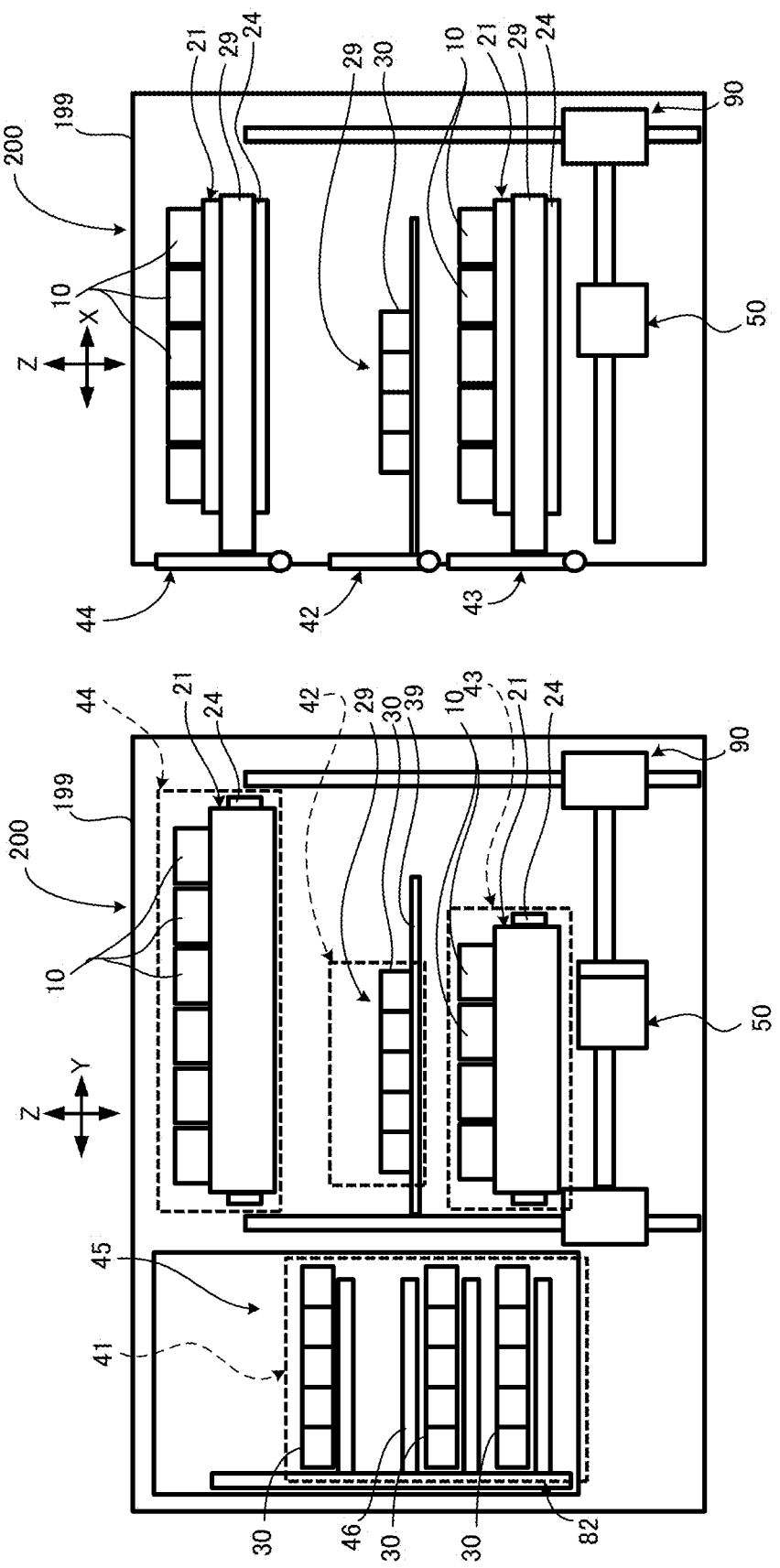

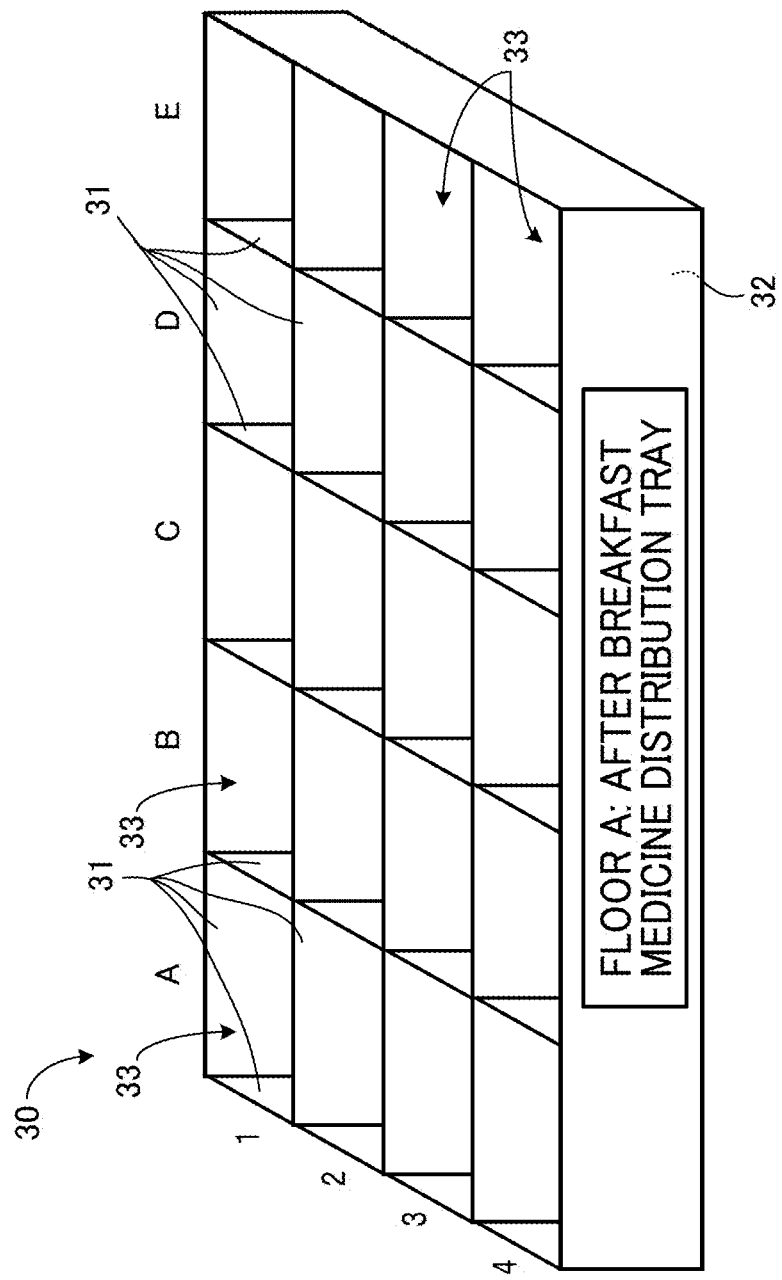

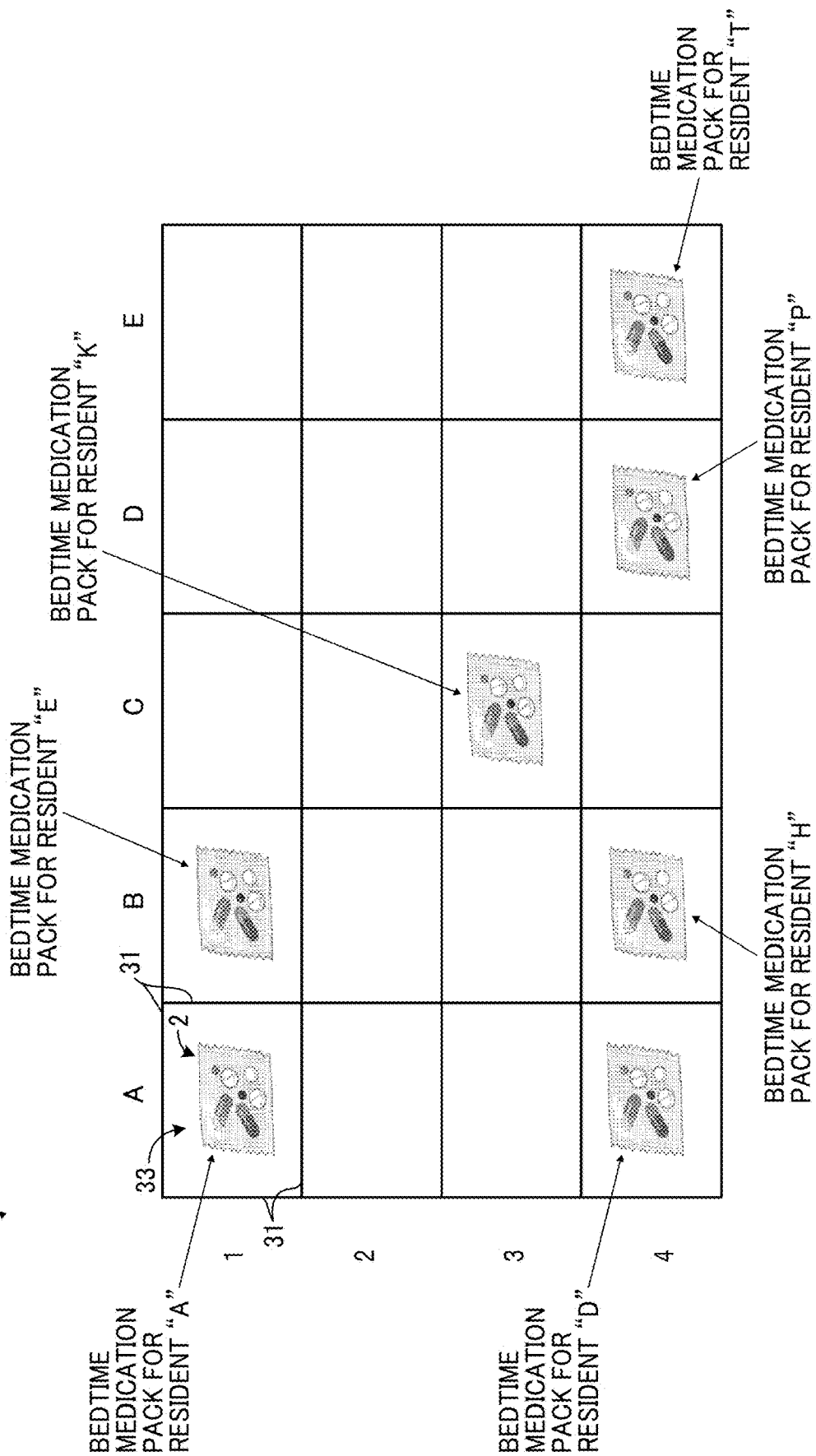

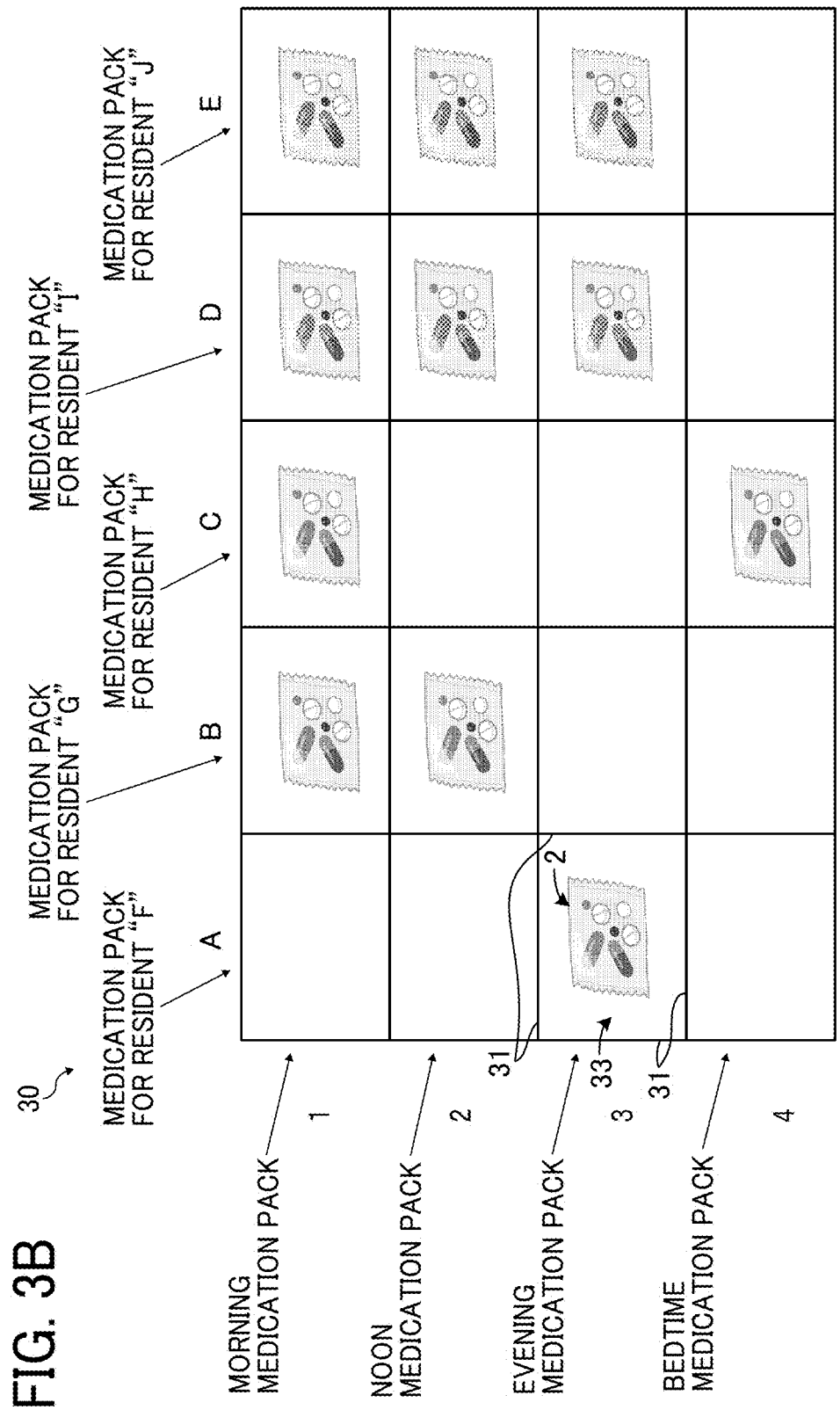

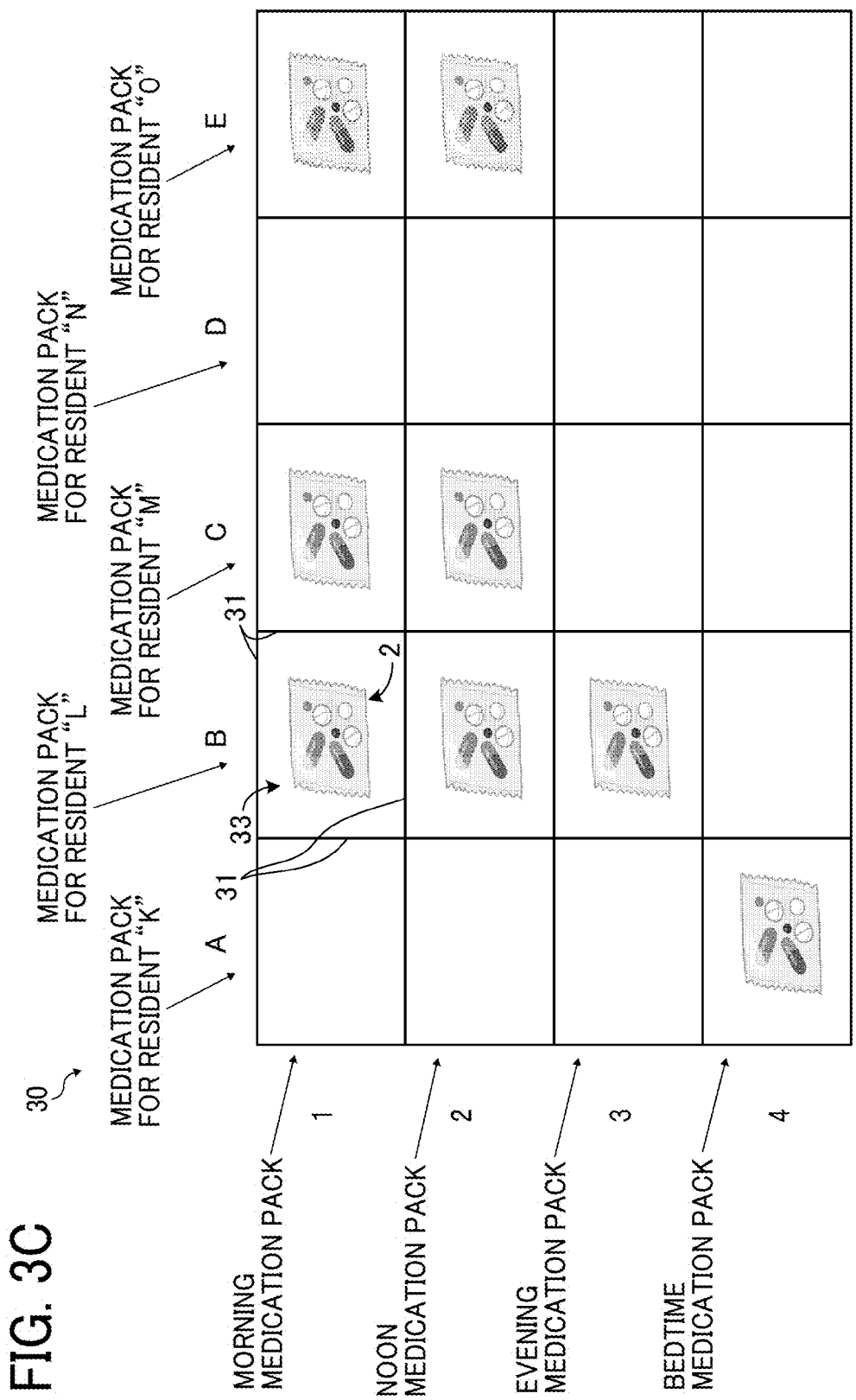

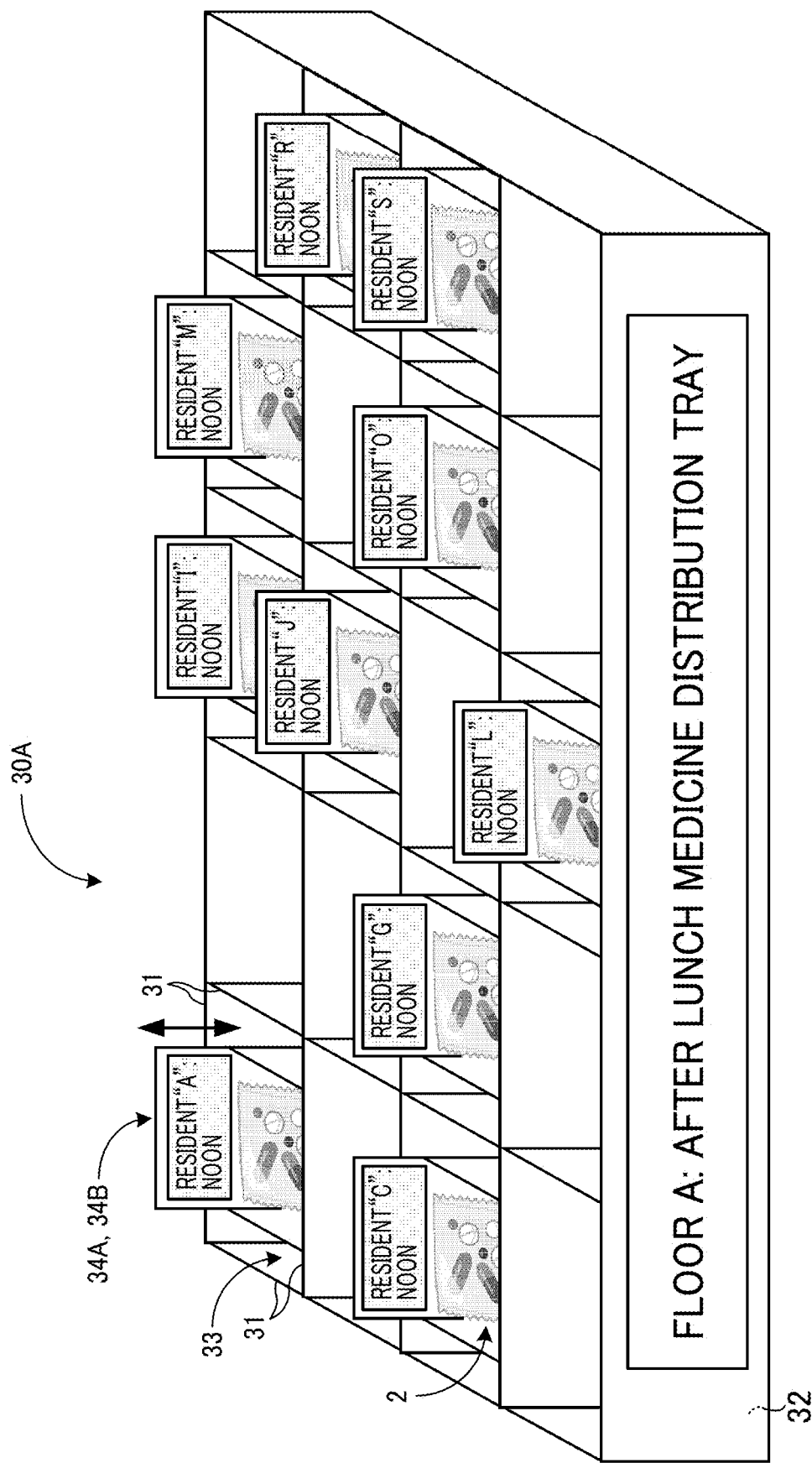

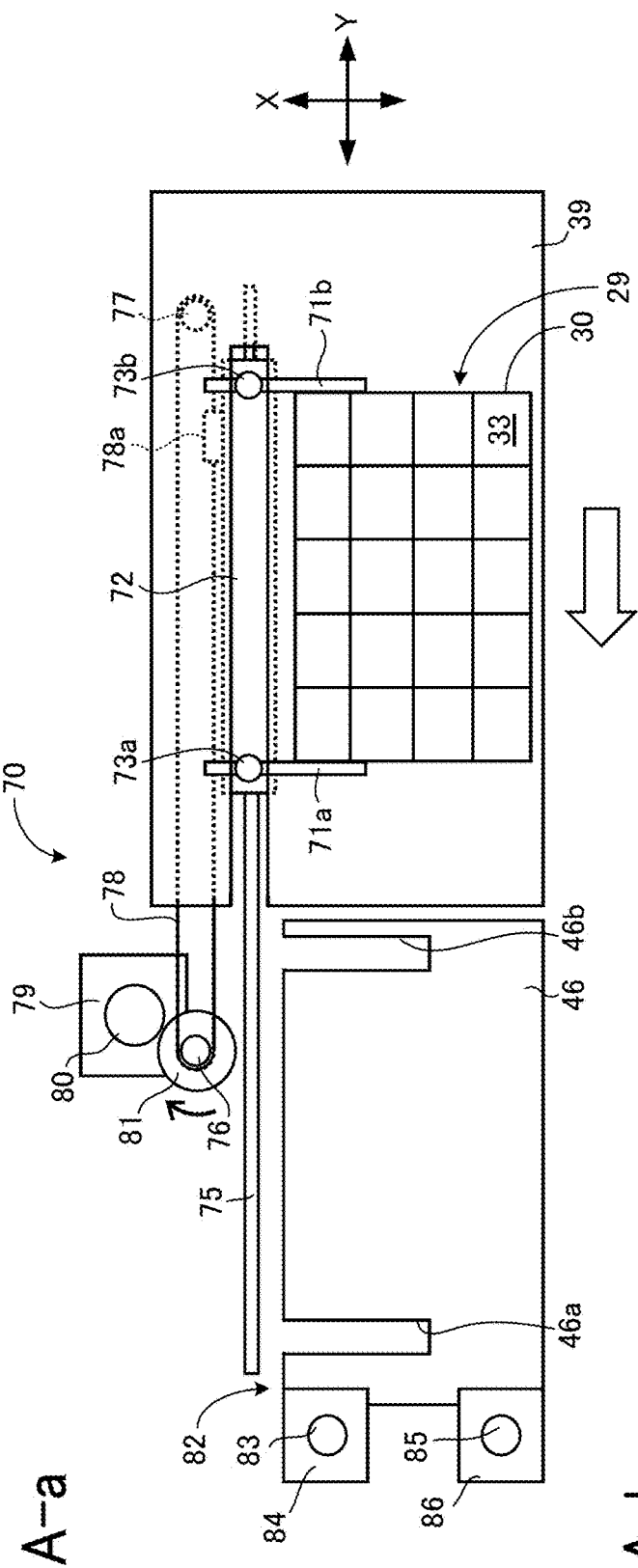

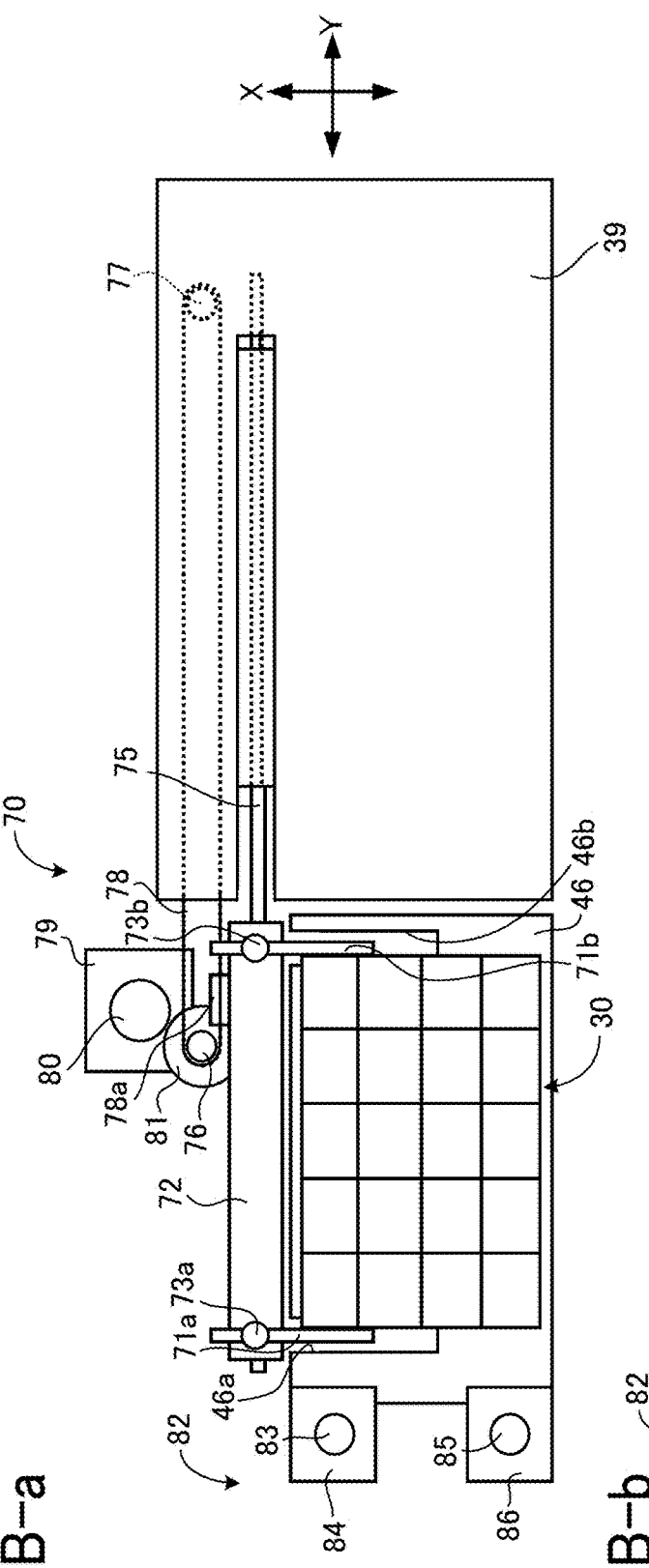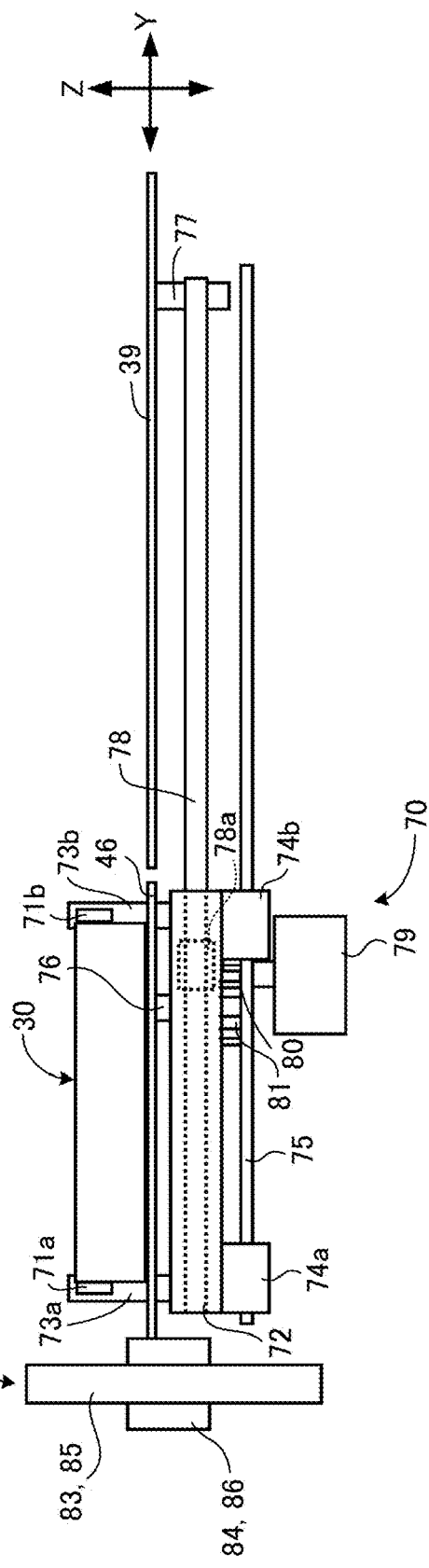

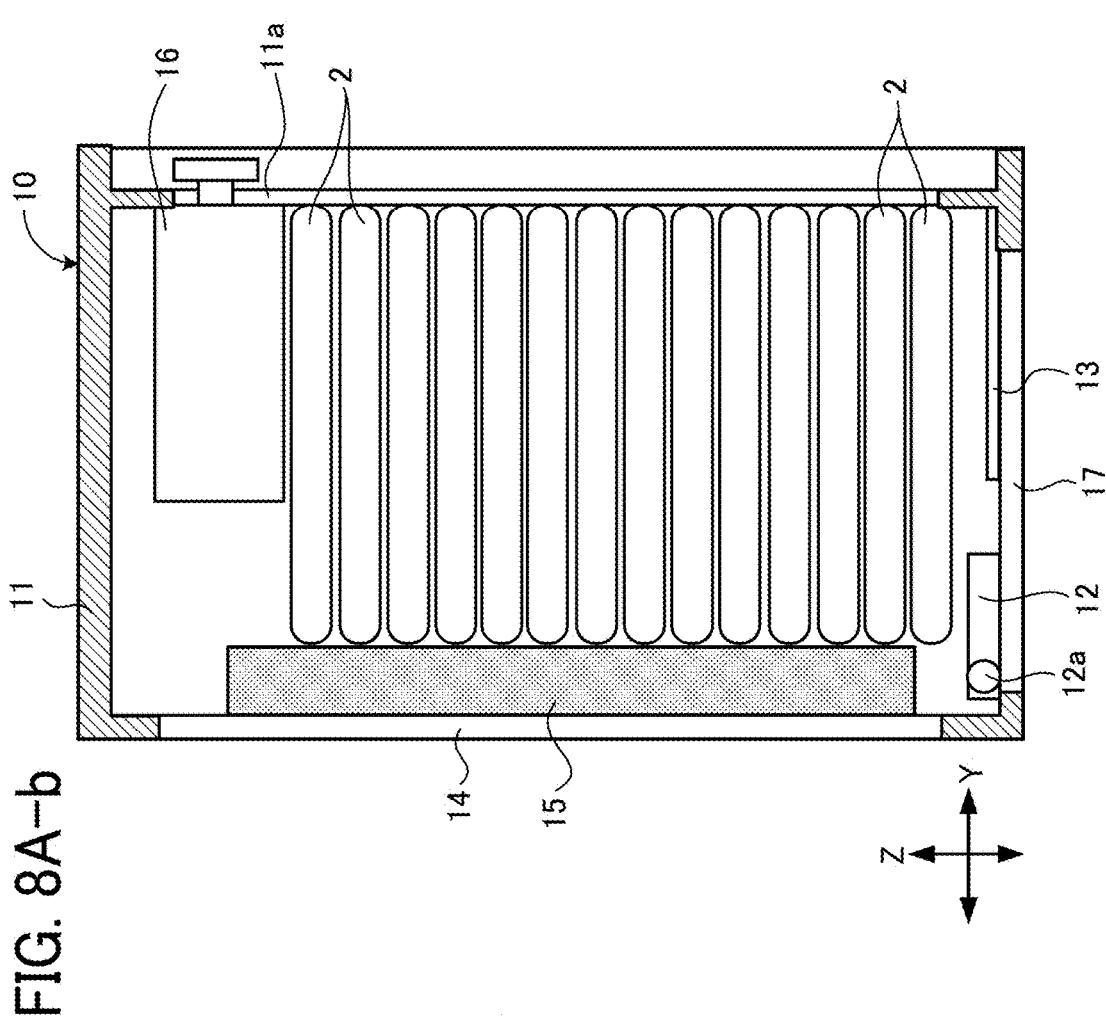
FIG. 8A-a
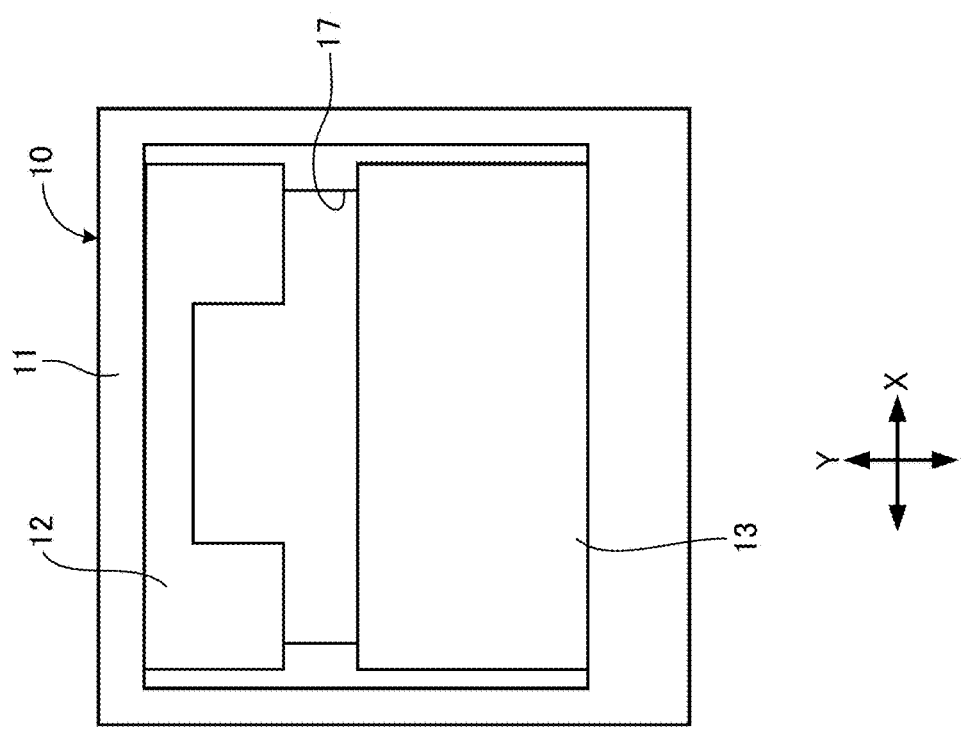
FIG. 8A-b

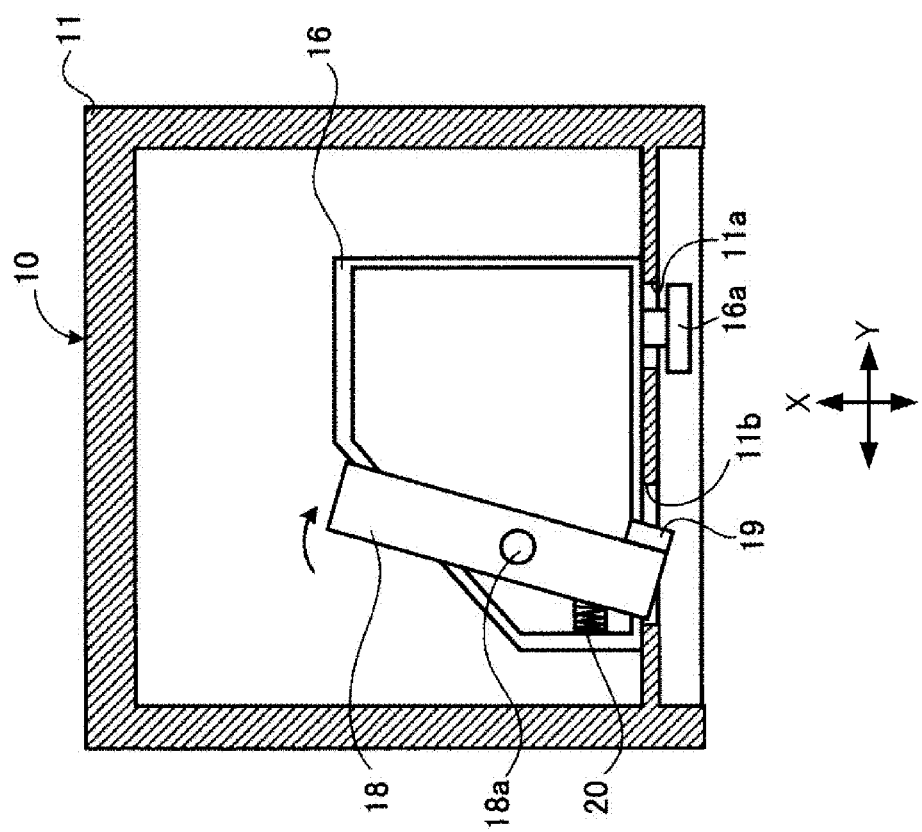
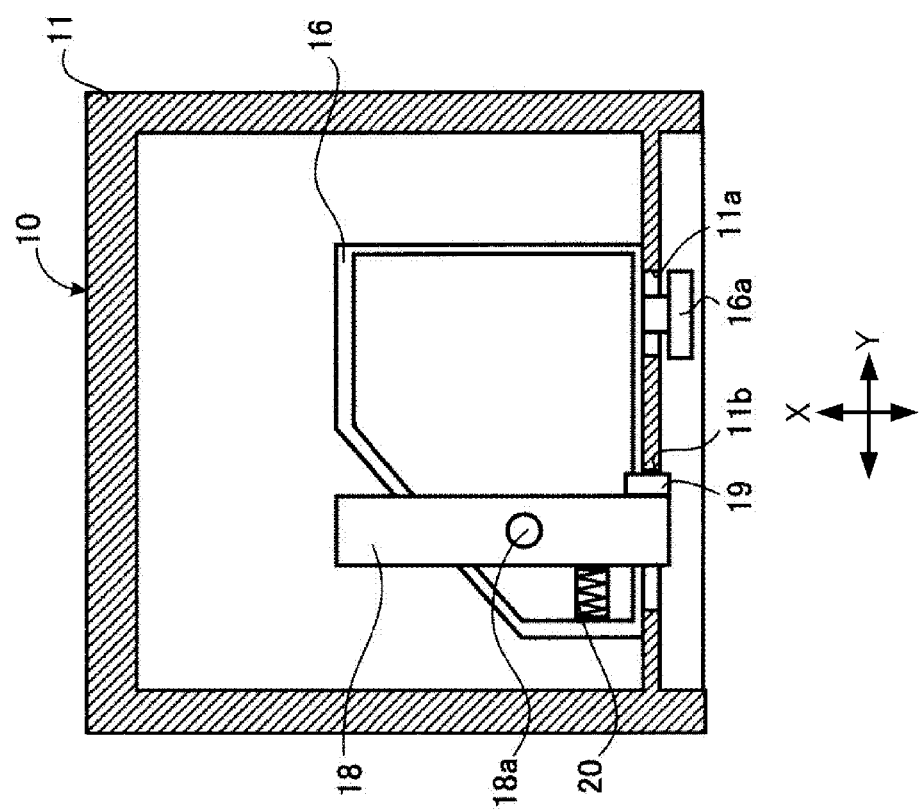

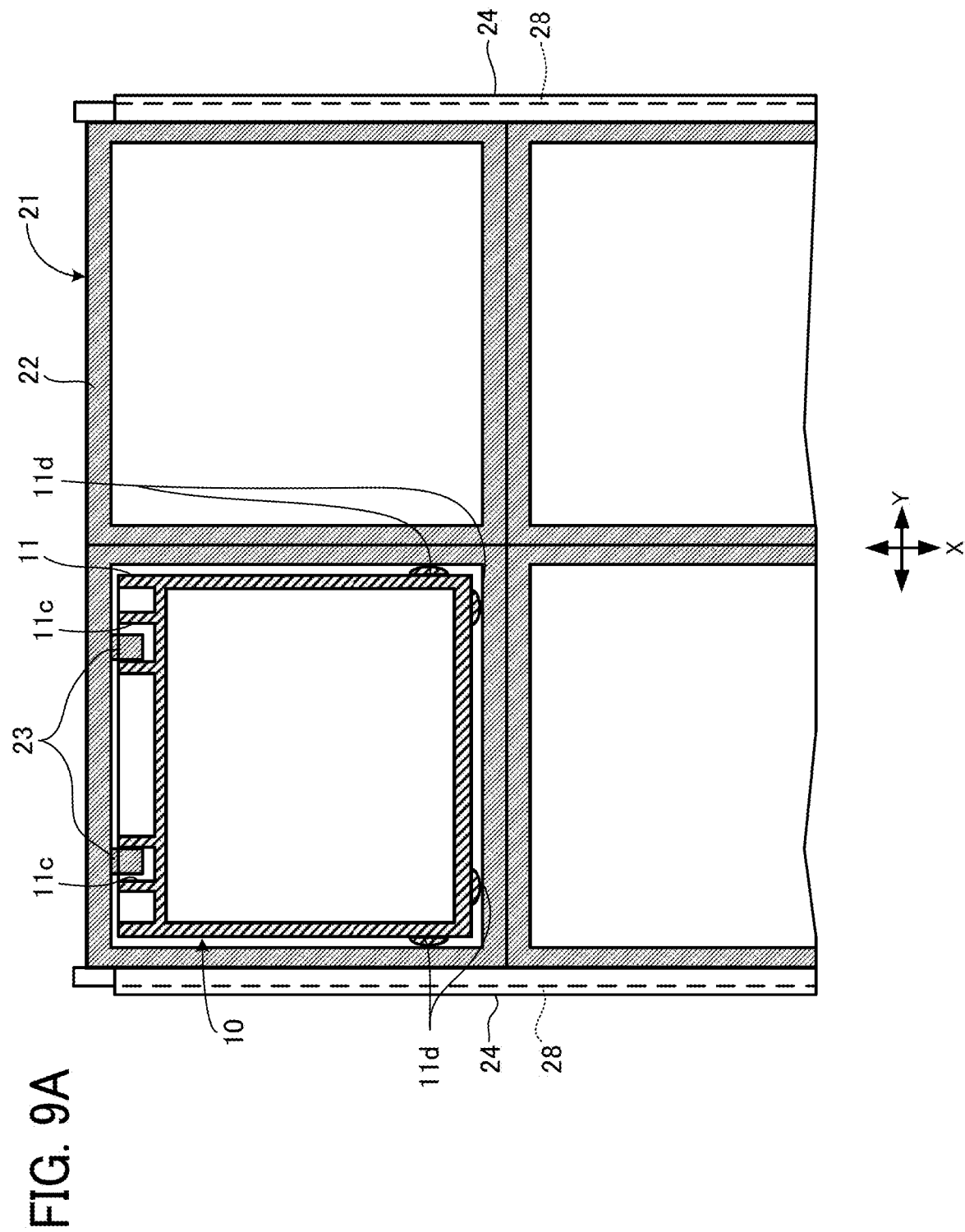

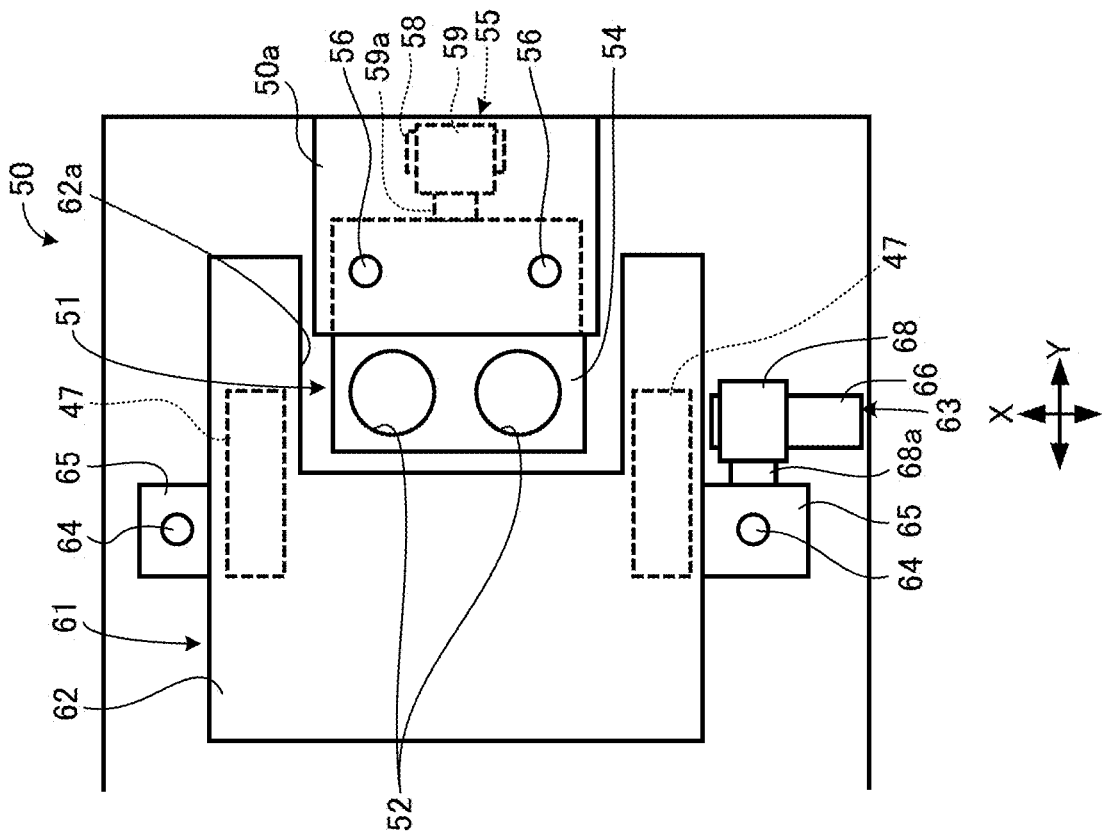
FIG. 10A-b
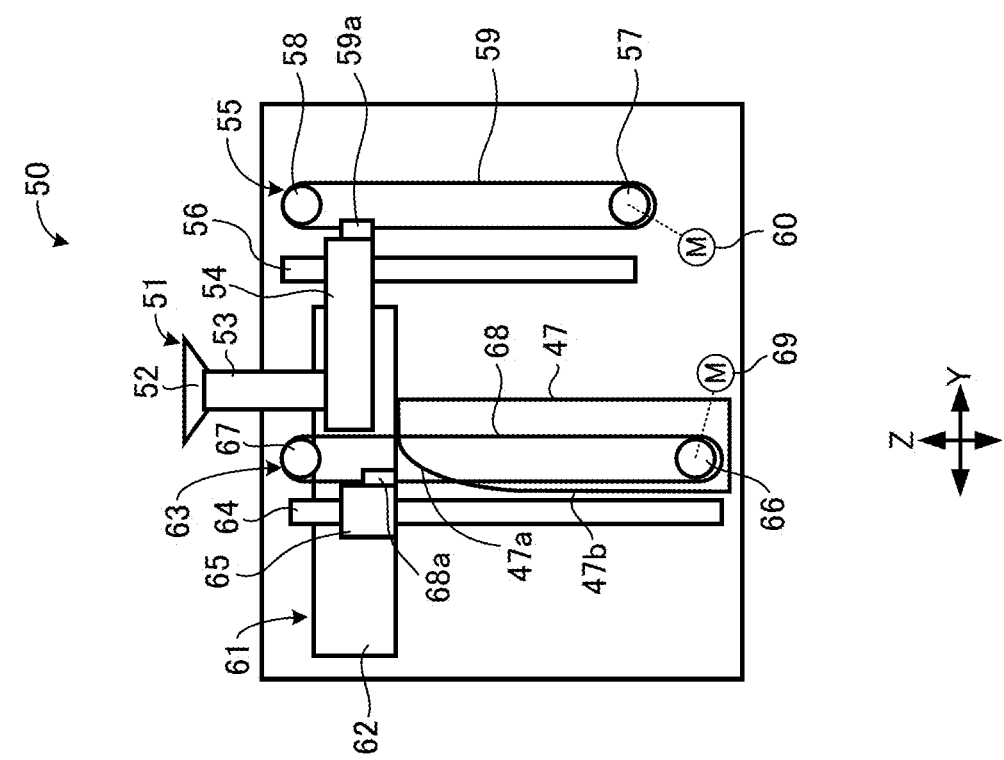
FIG. 10A-a

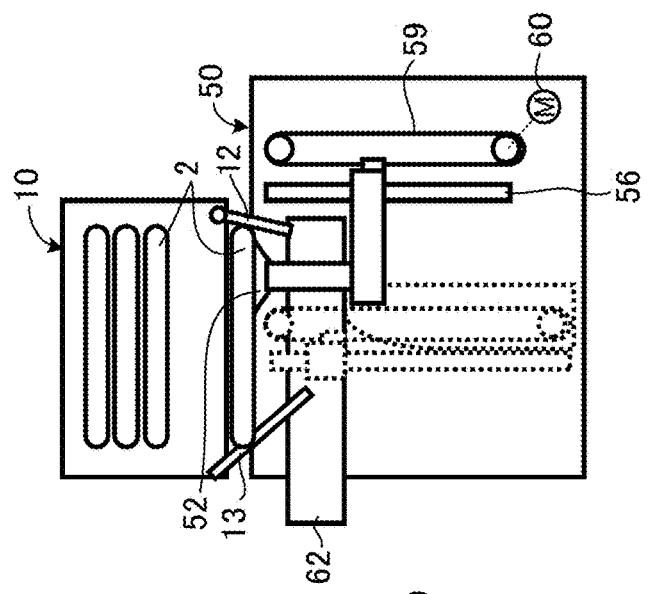
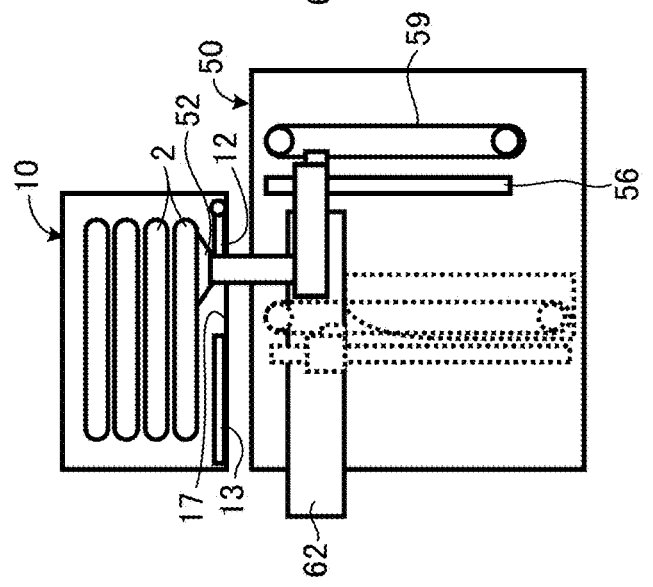
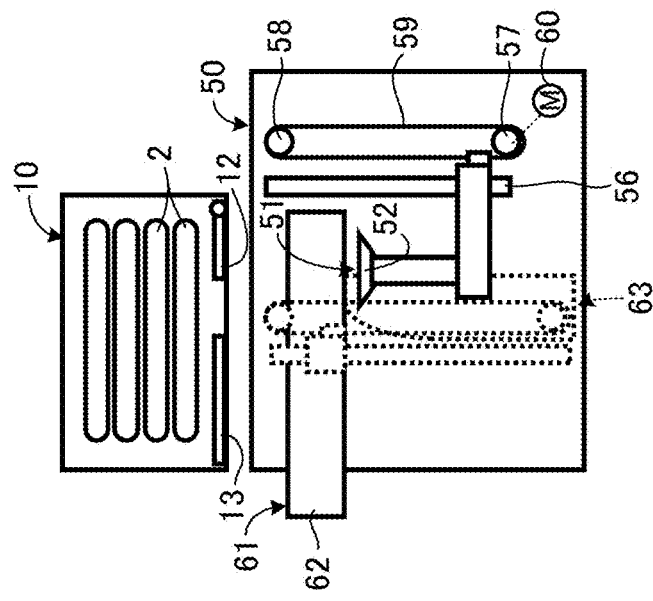

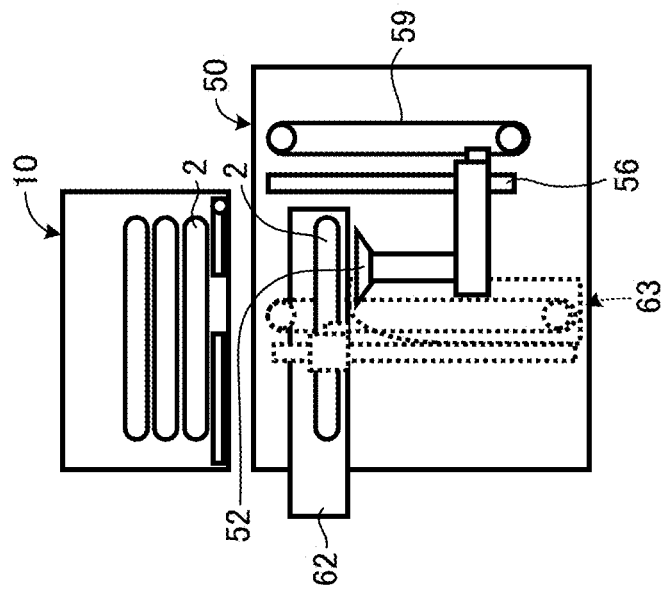
FIG. 10B-d
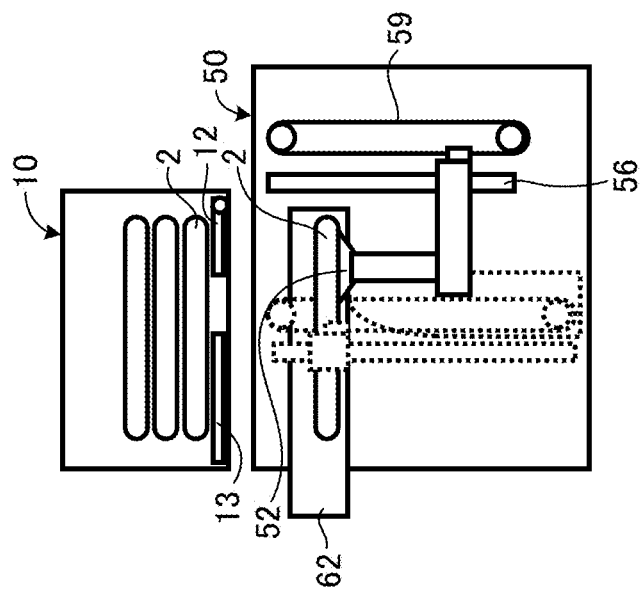
FIG. 10B-e

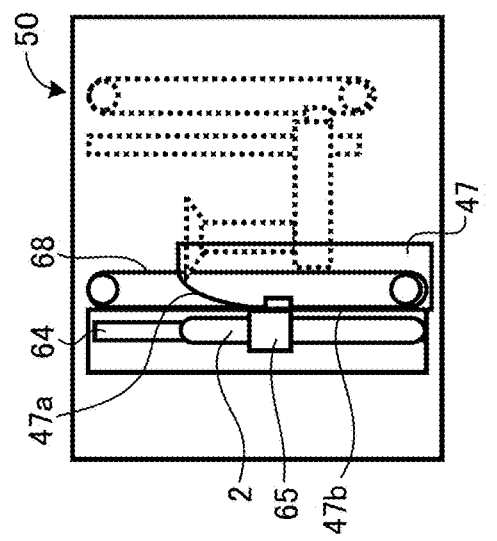
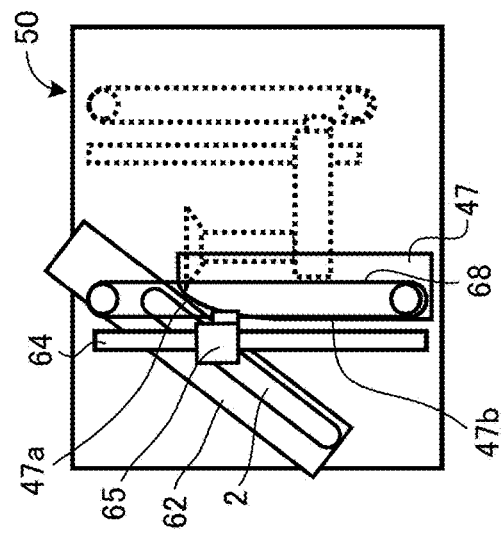
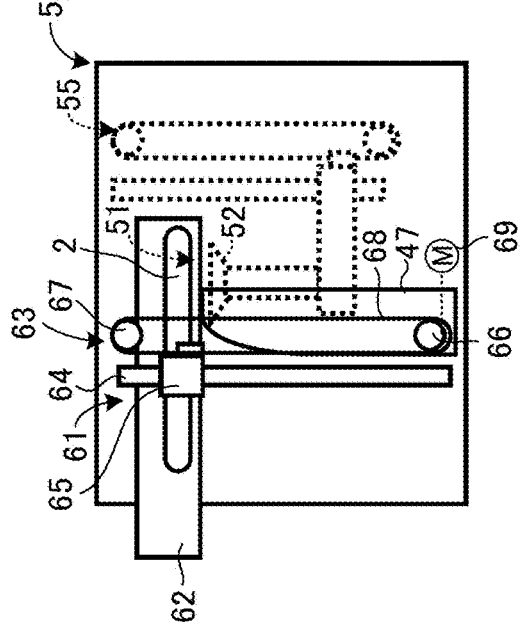
FIG. 10C-a  FIG. 10C-a'  FIG. 10C-b

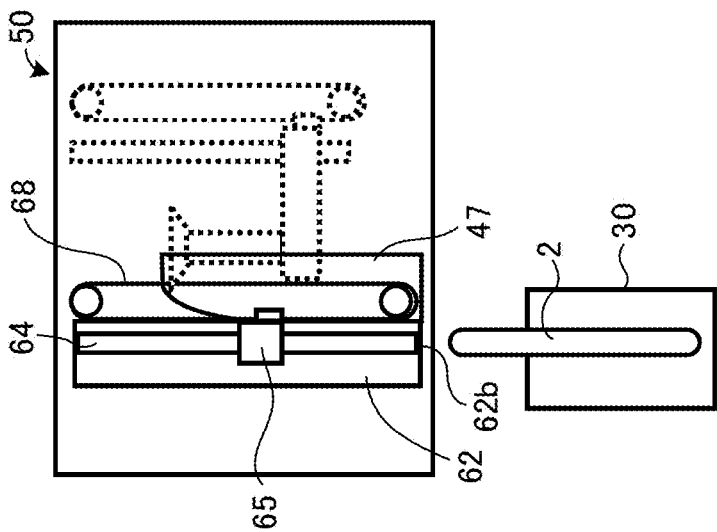
FIG. 10C-e
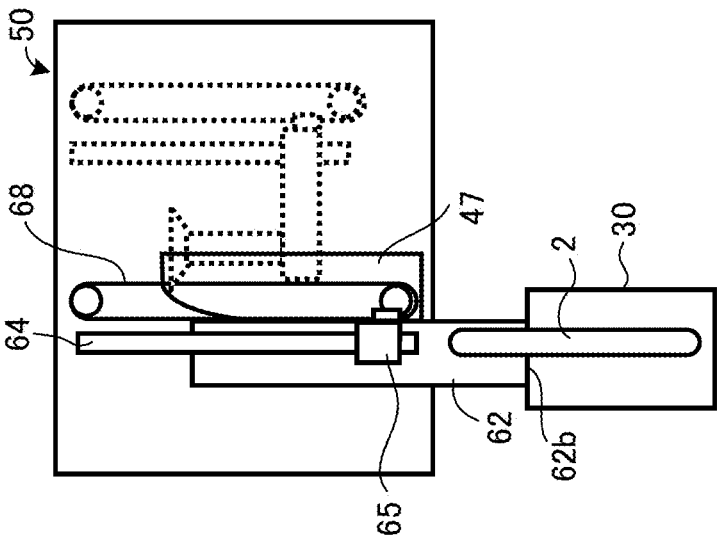
FIG. 10C-d
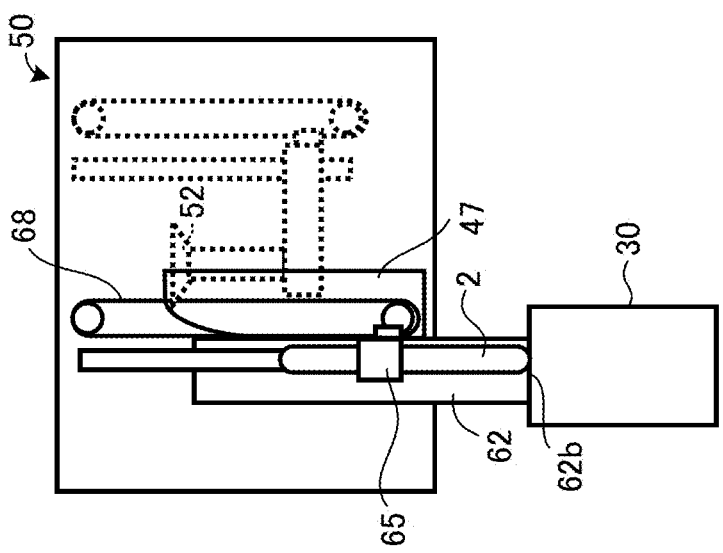
FIG. 10C-c

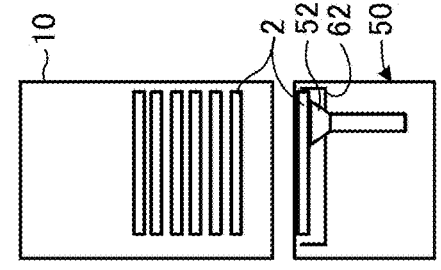
FIG. 16A1
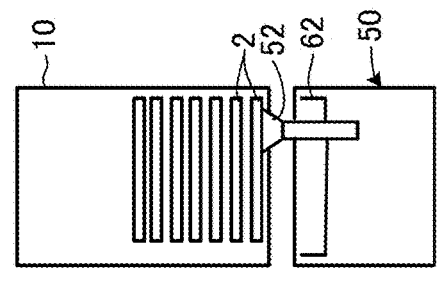
FIG. 16A2
FIG. 16A3
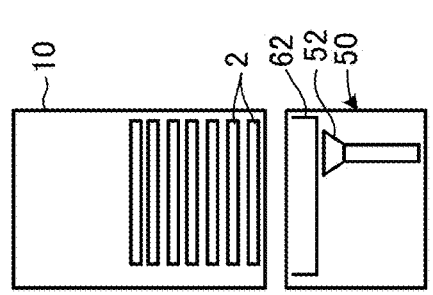
FIG. 16B
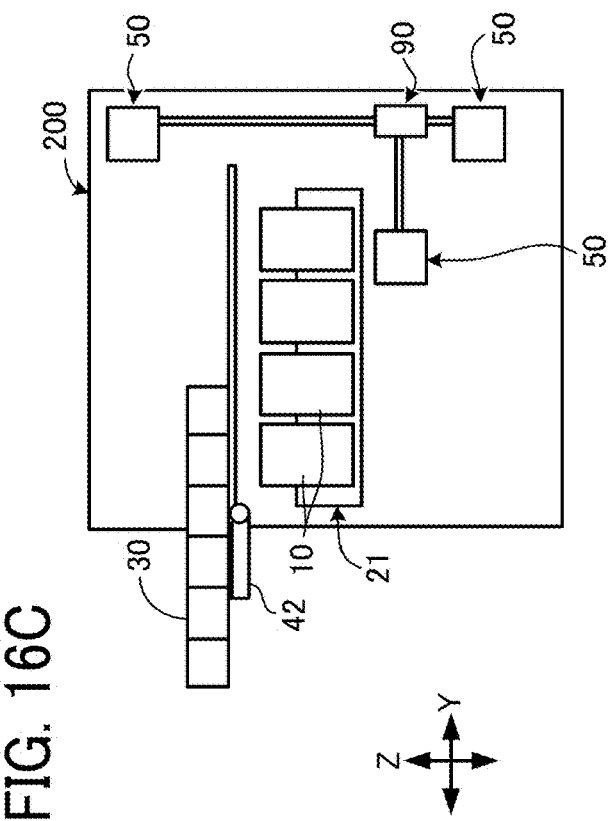
FIG. 16C
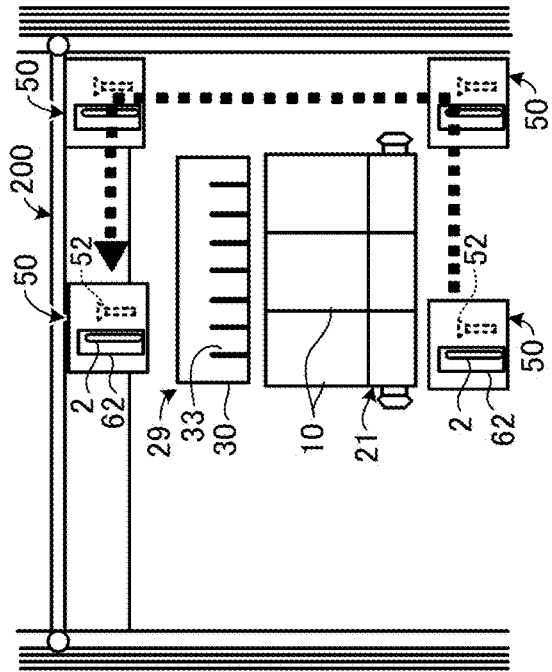

BASIC INFORMATION

| | |
|---:|:---|
| ID: | INPUT ID NO. |
| NAME (FAMILY NAME): | INPUT LAST NAME |
| NAME (FIRST NAME): | INPUT FIRST NAME |
| DATE OF BIRTH: | [Y ∨] [M ∨] [D ∨]   AGE: [ ] |
| SEX: | SELECT SEX ∨ |
| BLOOD TYPE: | SELECT BLOOD TYPE ∨ |
| DATE OF ADMISSION: | [Y ∨] [M ∨] [D ∨] |
| ROOM NUMBER: | [BD ∨] [FL ∨] [RM ∨] |

[RETURN] [REGISTER]

FIG. 22

MEDICATION INFORMATION

| PACK NO. 1 | PACK NO. 2 | PACK NO. 3 | PACK NO. 4 | PACK NO. 5 |

NAME: A

ROOM NUMBER: A-1F-101

| No. | MEDI-CINE | DOSE | TYPE | | |
|---|---|---|---|---|---|
| 1 | MEDI-CINE A | 2 [TABLET] | TABLET ▽ | | |
| 2 | MEDI-CINE B | 1 [CAPSULE] | CAPSULE ▽ | | |
| 3 | | | | | |
| 4 | | | | | |
| 5 | | | | | |
| 6 | | | | | |

NUMBER OF PACK: SELECT QUANTITY ▽

CONTAINER NO.: SELECT CARTRIDGE ▽

MEDICATION TIMING: SELECT TIMING ▽

[CONTAINER]

DRAWER NO. [ ] COLUMN NO. [ ] ROW NO. [ ]

[MEDICINE DISTRIBU-TION TRAY]

TRAY NO. [ ] COLUMN NO. [ ] ROW NO. [ ]

[RETURN] [REGISTER]

MEDICATION INFORMATION (CONTAINER)

PACK NO.: 1
NAME: A
MEDICATION TIMING: MORNING

DRAWER NO.: SELECT DRAWER NO. ▽
COLUMN NO.: SELECT COLUMN NO. ▽
ROW NO.: SELECT ROW NO. ▽

NO. 2 [SELECT]
NO. 1 [SELECT]

|   | A | B | C | D |
|---|---|---|---|---|
| 5 | SELECT | SELECT | SELECT | SELECT |
| 4 | SELECT | SELECT | SELECT | SELECT |
| 3 |   |   |   |   |
| 2 | SELECT |   | SELECT | SELECT |
| 1 | SELECT |   | SELECT | SELECT |

[RETURN] [REGISTER]

FIG. 24

**MEDICATION INFORMATION
(MEDICINE DISTRIBUTION TRAY)**

PACK NO.: 1  
NAME: A  
MEDICATION TIMING: MORNING

TRAY NO.: SELECT TRAY NO. ▽  
COLUMN NO.: SELECT COLUMN NO. ▽  
ROW NO.: SELECT ROW NO. ▽

|   | A | B | C | D | E |
|---|---|---|---|---|---|
| 1 | SELECT | SELECT | SELECT | SELECT | SELECT |
| 2 |        | SELECT | SELECT | SELECT | SELECT |
| 3 |        | SELECT | SELECT | SELECT | SELECT |
| 4 |        | SELECT | SELECT | SELECT | SELECT |

[RETURN] [REGISTER]

FIG. 25

MEDICATION INFORMATION

| PACK NO. 1 | PACK NO. 2 | PACK NO. 3 | PACK NO. 4 | PACK NO. 5 |

NAME: A

ROOM NUMBER: A-1F-101

| No. | MEDI-CINE | DOSE | TYPE | | | |
|---|---|---|---|---|---|---|
| 1 | MEDI-CINE A | 2 [TABLET] | TABLET ∨ | | | |
| 2 | MEDI-CINE B | 1 [CAPSULE] | CAPSULE ∨ | | | |
| 3 | | | | | | |
| 4 | | | | | | |
| 5 | | | | | | |
| 6 | | | | | | |

NUMBER OF PACK: 14 ∨

CONTAINER NO.: A-A-1 ∨

MEDICATION TIMING: MORNING ∨

[CONTAINER]
DRAWER NO. 1 | COLUMN NO. A | ROW NO. 1

[MEDICINE DISTRIBU-TION TRAY]
TRAY NO. A(MOR-NING) | COLUMN NO. A | ROW NO. 1

[RETURN] [REGISTER]

MEDICATION INFORMATION

| PACK NO.① | PACK NO.② | PACK NO.③ | PACK NO.④ | PACK NO.⑤ |

NAME: A    ROOM NUMBER: A-1F-101    NUMBER OF PACK CONTAINED: 14    A-A-1 ⌄

| No. | MEDI-CINE | DOSE | TYPE | | |
|---|---|---|---|---|---|
| 1 | MEDI-CINE A | 2 [TABLETS] | | | |
| 2 | MEDI-CINE B | 1 [CAPSULE] | | | |
| 3 | | | | | |
| 4 | | | | | |
| 5 | | | | | |
| 6 | | | | | ⌄ |

REGISTRATION OK

[CLOSE]

MEDICINE DISTRIBU-TION TRAY

MORNING ⌄

| DRAWER NO. | COLUMN NO. | ROW NO. |
|---|---|---|
| 1 | A | 1 |

| TRAY NO. | COLUMN NO. | ROW NO. |
|---|---|---|
| A (MOR-NING) | A | 1 |

[RETURN] [REGISTER]

FIG. 27

**CONFIRM REGISTRATION INFORMATION
(CONTAINER/MEDICINE DISTRIBUTION TRAY)**

| MORNING | NOON | EVENING | BEDTIME |
|---|---|---|---|

| ID | NAME | SEX | ROOM NUMBER | CONTAINER NO. | MEDICINE DISTRIBUTION TRAY NO. | |
|---|---|---|---|---|---|---|
| 1 | A | MALE | A-1F-101 | ①-A-1 | A(MORNING)-A-1 | DETAIL |
| 2 | B | MALE | A-1F-102 | ①-B-1 | A(MORNING)-A-2 | DETAIL |
| 3 | C | MALE | A-1F-103 | ①-C-1 | A(MORNING)-A-3 | DETAIL |
| 4 | D | FEMALE | A-1F-104 | ①-D-1 | A(MORNING)-A-4 | DETAIL |
| 5 | E | FEMALE | A-1F-105 | ①-A-2 | A(MORNING)-B-1 | DETAIL |
| 6 | F | FEMALE | A-1F-106 | UNREGISTERED | UNREGISTERED | |

[MEDICATION TIMING] [RETURN]

FIG. 28

CONFIRM REGISTRATION INFORMATION (MEDICATION TIMING)

| ID | NAME | SEX | ROOM NUMBER | MORNING | NOON | EVENING | BEDTIME | |
|----|------|-----|-------------|---------|------|---------|---------|---|
| 1 | A | MALE | A-1F-101 | MEDICATION (1) | MEDICATION (1) | MEDICATION (1) | MEDICATION (1) | DETAIL |
| 2 | B | MALE | A-1F-102 | MEDICATION (1) | UNREGISTERED | MEDICATION (1) | UNREGISTERED | DETAIL |
| 3 | C | MALE | A-1F-103 | MEDICATION (1) | MEDICATION (1) | UNREGISTERED | UNREGISTERED | DETAIL |
| 4 | D | FEMALE | A-1F-104 | MEDICATION (13) | UNREGISTERED | UNREGISTERED | MEDICATION (13) | DETAIL |
| 5 | E | FEMALE | A-1F-105 | MEDICATION (13) | UNREGISTERED | MEDICATION (13) | MEDICATION (13) | DETAIL |
| 6 | F | FEMALE | A-1F-106 | UNREGISTERED | UNREGISTERED | MEDICATION (13) | UNREGISTERED | DETAIL |

CONTAINER / TRAY

RETURN

FIG. 29

CHANGE OR DELETE

| ID | NAME | SEX | ROOM NUMBER | MORNING | NOON | EVENING | BEDTIME | | |
|---|---|---|---|---|---|---|---|---|---|
| 1 | A | MALE | A-1F-101 | MEDICA-TION (1) | MEDICA-TION (1) | MEDICA-TION (1) | MEDICA-TION (1) | CHANGE | DELETE |
| 2 | B | MALE | A-1F-102 | MEDICA-TION (1) | UNREGIS-TERED | MEDICA-TION (1) | UNREGIS-TERED | CHANGE | DELETE |
| 3 | C | MALE | A-1F-103 | MEDICA-TION (1) | MEDICA-TION (1) | UNREGIS-TERED | UNREGIS-TERED | CHANGE | DELETE |
| 4 | D | FEMALE | A-1F-104 | MEDICA-TION (13) | UNREGIS-TERED | UNREGIS-TERED | MEDICA-TION (13) | CHANGE | DELETE |
| 5 | E | FEMALE | A-1F-105 | MEDICA-TION (13) | UNREGIS-TERED | MEDICA-TION (13) | MEDICA-TION (13) | CHANGE | DELETE |
| 6 | F | FEMALE | A-1F-106 | UNREGIS-TERED | UNREGIS-TERED | MEDICA-TION (13) | UNREGIS-TERED | CHANGE | DELETE |

151

RETURN

FIG. 32

CONFIRM CONTAINER INFORMATION

| | A | B | C | D |
|---|---|---|---|---|
| 5 | NAME: F / TIMING: EVENING [DETAIL] | NAME: G / TIMING: MORNING [DETAIL] | NAME: G / TIMING: NOON [DETAIL] | UNREGISTERED [DETAIL] |
| 4 | NAME: E / TIMING: MORNING [DETAIL] | UNREGISTERED [REGISTER] | NAME: E / TIMING: EVENING [DETAIL] | NAME: E / TIMING: BEDTIME [DETAIL] |
| 3 | NAME: C / TIMING: MORNING [DETAIL] | NAME: C / TIMING: NOON [DETAIL] | NAME: D / TIMING: MORNING [DETAIL] | NAME: D / TIMING: BEDTIME [DETAIL] |
| 2 | NAME: B / TIMING: MORNING [DETAIL] | NAME: B / TIMING: EVENING [DETAIL] | UNREGISTERED [REGISTER] | UNREGISTERED [REGISTER] |
| 1 | NAME: A / TIMING: MORNING [DETAIL] | NAME: A / TIMING: NOON [DETAIL] | NAME: A / TIMING: EVENING [DETAIL] | NAME: A / TIMING: BEDTIME [DETAIL] |

DRAWER NO. ①     DRAWER NO. ②

[RETURN]

ADD OR DELETE MEDICINE

| ID | NAME | SEX | ROOM NUMBER | MORNING | NOON | EVENING | BEDTIME | |
|----|------|-----|-------------|---------|------|---------|---------|---|
| 1 | A | MALE | A-1F-101 | MEDICATION (1) | MEDICATION (1) | MEDICATION (1) | MEDICATION (1) | SELECT |
| 2 | B | MALE | A-1F-102 | MEDICATION (1) | UNREGISTERED | MEDICATION (1) | UNREGISTERED | SELECT |
| 3 | C | MALE | A-1F-103 | MEDICATION (1) | MEDICATION (1) | UNREGISTERED | UNREGISTERED | SELECT |
| 4 | D | FEMALE | A-1F-104 | MEDICATION (13) | UNREGISTERED | UNREGISTERED | MEDICATION (13) | SELECT |
| 5 | E | FEMALE | A-1F-105 | MEDICATION (13) | UNREGISTERED | MEDICATION (13) | MEDICATION (13) | SELECT |
| 6 | F | FEMALE | A-1F-106 | UNREGISTERED | UNREGISTERED | MEDICATION (13) | UNREGISTERED | SELECT |

RETURN

FIG. 34

| PACK NO.① | PACK NO.② | PACK NO.③ | PACK NO.④ | PACK NO.⑤ |

ADD OR DELETE MEDICINE

NAME: A    ROOM NUMBER: A-1F-101

| No. | MEDI-CINE | DOSE | TYPE | | | |
|---|---|---|---|---|---|---|
| 1 | MEDI-CINE A | 2 [TABLET] | TABLET ∨ | | | |
| 2 | MEDI-CINE B | 1 [CAPSULE] | CAPSULE ∨ | | | |
| 3 | | | | | | |
| 4 | | | | | | |
| 5 | | | | | | |
| 6 | | | | | | |

NUMBER OF ADDED PACK: SELECT NUMBER OF ADDED PACK ∨

CONTAINER NO.: A-A-1 ∨

MEDICATION TIMING: MORNING ∨

CONTAINER
DRAWER NO. ① | COLUMN NO. A | ROW NO. 1

MEDICINE DISTRIBU-TION TRAY
TRAY NO. A(MOR-NING) | COLUMN NO. A | ROW NO. 1

RETURN    REGISTER

FIG. 36

| | TRAY NO. A(MORNING) | | TRAY NO. B(NOON) | | TRAY NO. C (EVENING) | | TRAY NO. D(BEDTIME) | |
|---|---|---|---|---|---|---|---|---|
| | \multicolumn{8}{l}{MEDICINE DISTRIBUTION COMPLETION TIME: 16:00   MEDICINE DISTRIBUTION TIME (APPROX.): 17 MIN.} | |
| | A | | B | | C | | D | | E | |
| 1 | NAME: A / TIMING: MORNING | CHANGE | NAME: E / TIMING: MORNING | CHANGE | NAME: I / TIMING: EVENING | CHANGE | NAME: M / TIMING: MORNING | CHANGE | NAME: Q / TIMING: MORNING | CHANGE |
| 2 | NAME: B / TIMING: MORNING | CHANGE | UNREGISTERED | REGISTER | NAME: J / TIMING: MORNING | CHANGE | UNREGISTERED | REGISTER | NAME: R / TIMING: MORNING | CHANGE |
| 3 | NAME: C / TIMING: MORNING | CHANGE | NAME: G / TIMING: MORNING | CHANGE | UNREGISTERED | REGISTER | NAME: O / TIMING: MORNING | CHANGE | NAME: S / TIMING: MORNING | CHANGE |
| 4 | NAME: D / TIMING: MORNING | CHANGE | NAME: H / TIMING: MORNING | CHANGE | NAME: L / TIMING: MORNING | CHANGE | NAME: P / TIMING: MORNING | CHANGE | NAME: T / TIMING: MORNING | CHANGE |

CONFIRM MEDICINE DISTRIBUTION TRAY INFORMATION

RETURN

CHANGE OF MEDICINE DISTRIBUTION TIME

| | DISTRIBUTION TRAY NO. | STATUS | REQUIRED DIS-TRIBUTION TIME | DISTRIBUTION START TIME | | DISTRIBUTION COMPLETION TIME | |
|---|---|---|---|---|---|---|---|
| 1 | A (MORNING) | IN USE | 17 [MIN.] | NON-ACTIVE ∨ | 15:33 (APPROX.) | ACTIVE ∨ | 16 : 00 ∨ |
| 2 | B (NOON) | IN USE | 10 [MIN.] | NON-ACTIVE ∨ | 15:50 (APPROX.) | ACTIVE ∨ | 16 : 00 ∨ |
| 3 | C (EVENING) | IN USE | 9 [MIN.] | ACTIVE ∨ | 10 : 00 ∨ | NON-ACTIVE ∨ | 10:09 (APPROX.) |
| 4 | D (BEDTIME) | IN USE | 8 [MIN.] | ACTIVE ∨ | 10 : 00 ∨ | NON-ACTIVE ∨ | 10:17 (APPROX.) |
| 5 | E (MORNING BACKUP) | ACTUAL USAGE | − [MIN.] | NON-ACTIVE ∨ | | NON-ACTIVE ∨ | |
| 6 | F (EVENING BACKUP) | ACTUAL USAGE | − [MIN.] | NON-ACTIVE ∨ | | NON-ACTIVE ∨ | |

RETURN

FIG. 38

CHANGE OF MEDICINE DISTRIBUTION TIME

| | DISTRIBUTION TRAY NO. | STATUS | TRAY TAKE-OUT TIME | | NEXT DAY | TRAY RETURN TIME | | NEXT DAY |
|---|---|---|---|---|---|---|---|---|
| 1 | A(MORNING) | IN USE | ACTIVE ∨ | 8 : 00 ∨ | | ACTIVE ∨ | 15 : 00 ∨ | |
| 2 | B(NOON) | IN USE | ACTIVE ∨ | 8 : 00 ∨ | | ACTIVE ∨ | 15 : 00 ∨ | |
| 3 | C(EVENING) | IN USE | ACTIVE ∨ | 10 : 30 ∨ | | ACTIVE ∨ | 18 : 30 ∨ | |
| 4 | D(BEDTIME) | IN USE | ACTIVE ∨ | 10 : 30 ∨ | | ACTIVE ∨ | 8 : 00 ∨ | ● |
| 5 | E(MORNING: BACKUP) | ACTUAL USAGE | NON-ACTIVE ∨ | | | NON-ACTIVE ∨ | | |
| 6 | F(EVENING: BACKUP) | ACTUAL USAGE | NON-ACTIVE ∨ | | | NON-ACTIVE ∨ | | |

RETURN

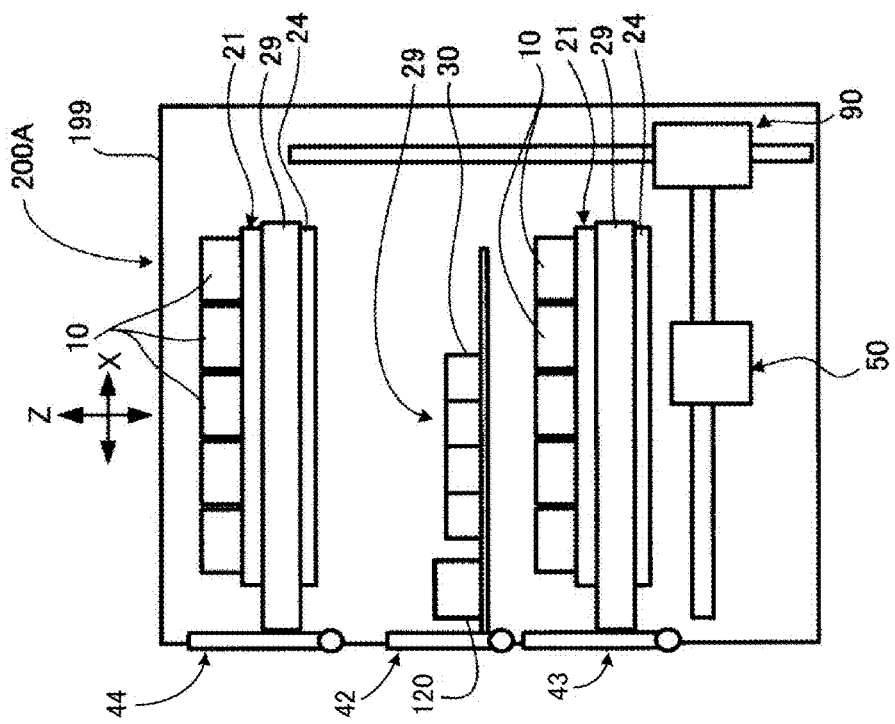
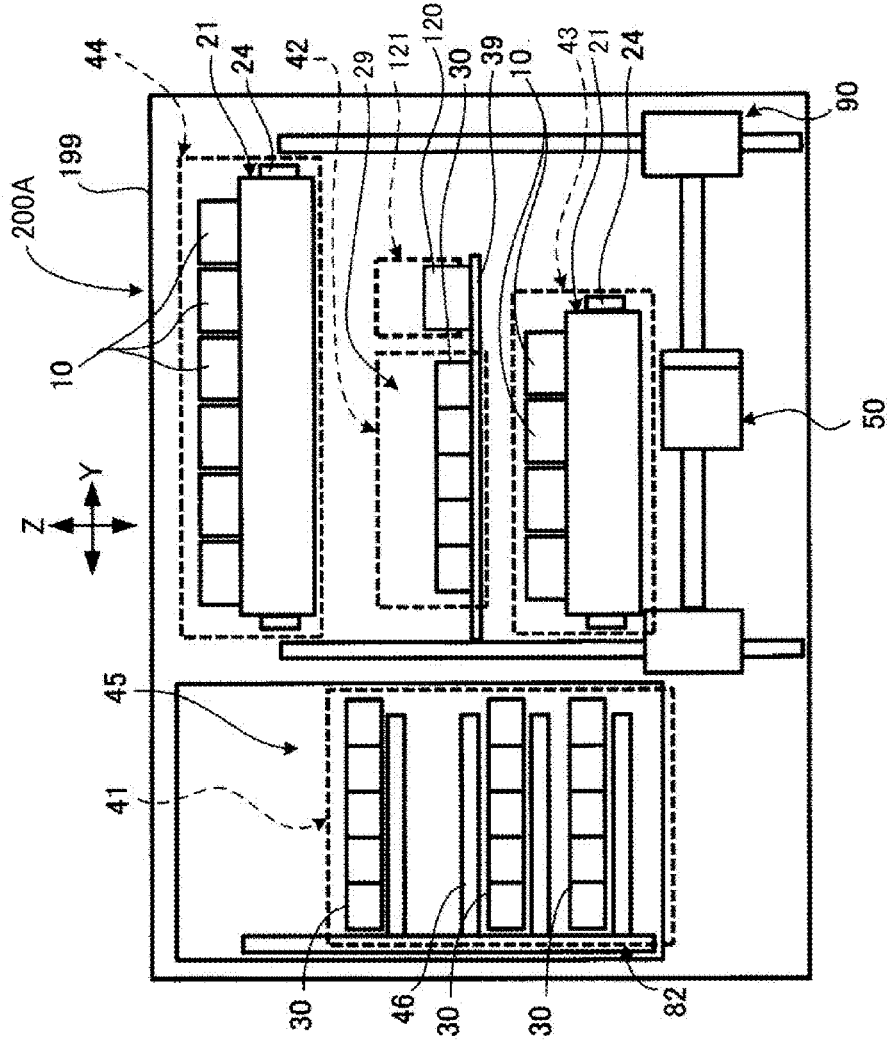

FIG. 41

| | DISTRIBUTION TRAY NO. | STATUS | REQUIRED DIS-TRIBUTION TIME | |
|---|---|---|---|---|
| 1 | A(MORNING) | IN USE | 17 [MIN.] | SELECT |
| 2 | B(NOON) | IN USE | 10 [MIN.] | SELECT |
| 3 | C(EVENING) | IN USE | 9 [MIN.] | SELECT |
| 4 | D(BEDTIME) | IN USE | 8 [MIN.] | SELECT |
| 5 | E(MORNING: BACKUP) | ACTUAL USAGE | - [MIN.] | SELECT |
| 6 | F(EVENING: BACKUP) | ACTUAL USAGE | - [MIN.] | SELECT |

FORCED MEDICINE (TRAY) DISTRIBUTION

RETURN

FIG. 43

FORCED MEDICINE (SINGLE TRAY) DISTRIBUTION

| ID | NAME | SEX | ROOM NUMBER | MORNING | NOON | EVENING | BEDTIME |
|---|---|---|---|---|---|---|---|
| 1 | A | MALE | A-1F-101 | MEDICA-TION (1) SELECT | MEDICA-TION (1) SELECT | MEDICA-TION (1) SELECT | MEDICA-TION (1) SELECT |
| 2 | B | MALE | A-1F-102 | MEDICA-TION (1) SELECT | UNREGISTERED | MEDICA-TION (1) SELECT | UNREGISTERED |
| 3 | C | MALE | A-1F-103 | MEDICA-TION (1) SELECT | MEDICA-TION (1) SELECT | UNREGISTERED | UNREGISTERED |
| 4 | D | FEMALE | A-1F-104 | MEDICA-TION (13) SELECT | UNREGISTERED | UNREGISTERED | MEDICA-TION (13) SELECT |
| 5 | E | FEMALE | A-1F-105 | MEDICA-TION (13) SELECT | UNREGISTERED | MEDICA-TION (13) SELECT | MEDICA-TION (13) SELECT |
| 6 | F | FEMALE | A-1F-106 | UNREGISTERED | UNREGISTERED | MEDICA-TION (13) SELECT | UNREGISTERED |

RETURN

FIG. 46

FORCED MEDICINE (SINGLE TRAY) DISTRIBUTION

| ID | NAME | SEX | ROOM NUMBER | MORNING | NOON | EVENING | BEDTIME |
|----|------|-----|-------------|---------|------|---------|---------|
| 1 | A | MALE | A-1F-101 | MEDICA-TION (1) [SELECT] | MEDICA-TION (1) [SELECT] | MEDICA-TION (1) [SELECT] | MEDICA-TION (1) [SELECT] |
| 2 | B | MALE | A-1F-102 | MEDICA-TION (1) [SELECT] | UNREGISTERED | MEDICA-TION (1) [SELECT] | UNREGISTERED |
| 3 | C | MALE | A-1F-103 | MEDICA-TION (1) [SELECT] | MEDICA-TION (1) [SELECT] | UNREGISTERED | UNREGISTERED |
| 4 | D | FEMALE | A-1F-104 | MEDICA-TION (13) [SELECT] | UNREGISTERED | UNREGISTERED | MEDICA-TION (13) [SELECT] |
| 5 | E | FEMALE | A-1F-105 | MEDICA-TION (13) [SELECT] | UNREGISTERED | MEDICA-TION (13) [SELECT] | MEDICA-TION (13) [SELECT] |
| 6 | F | FEMALE | A-1F-106 | UNREGISTERED | UNREGISTERED | MEDICA-TION (13) [SELECT] | UNREGISTERED |

[RETURN]

MEDICATION SUPPORT APPARATUS

CROSS-REFERENCE TO RELATED APPLICATION

This patent application is based on and claims priority pursuant to 35 U.S.C. § 119(a) to Japanese Patent Application No. 2020-090945, filed on May 25, 2020, in the Japan Patent Office, the entire disclosure of which is hereby incorporated by reference herein.

BACKGROUND

Technical Field

Embodiments of the present disclosure relate to a medication support apparatus.

Description of the Related Art

There is known a medication support apparatus that uses a suction device to take out a pack from a container that stores medicine packs (one-dose package of medicines), delivers the pack to a tray, and causes the pack to appear in an opening (outlet) of a body casing of the apparatus to deliver the medicine to a medicine recipient taking the medicine or a caregiver.

The above-described medication support apparatus allows to regularly deliver medicine to an individual medicine recipient. However, in a care facility or the like in which a plurality of medicine recipients is present, it is necessary to prepare medication support apparatuses for the number of medicine recipients.

SUMMARY

In an aspect of the present disclosure, a medication support apparatus includes a container, a medicine distribution member, a port, a take-out device, and a transfer device. The container is configured to store one-dose packages of medicines. The medicine distribution member includes a plurality of partitions configured to separately include the one-dose packages of medicines. The medicine distribution member is configured to enter and exit the medication support apparatus through the port. The take-out device is configured to take out a specific one of the one-dose packages of medicines from the container. The transfer device is configured to transfer the specific one of the one-dose packages of medicines taken out from the container. The one-dose packages of medicines are configured to be placed at predetermined positions partitioned by the plurality of partitions in the medicine distribution member.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 1A is a front view of an entire medication support apparatus according to an embodiment of the present disclosure;

FIG. 1B is a side view of the medication support apparatus illustrated in FIG. 1A according to an embodiment of the present disclosure;

FIG. 2A is an external perspective view of a basic configuration of a medicine distribution tray of a medication support apparatus according to an embodiment of the present disclosure;

FIG. 2E is a plan view of the medicine distribution tray according to Example 1 of the present disclosure;

FIG. 3B is a plan view of the medicine distribution tray according to Example 2 of the present disclosure;

FIG. 3C is a plan view of the medicine distribution tray according to Example 2 of the present disclosure;

FIG. 5 is an external perspective view of a medicine distribution tray according to a variation of Examples 1, 2, and 3 of the present disclosure;

FIG. 7A-a is a plan view illustrating a configuration and operation of a main part of a medicine-distribution-tray lateral mover of a medicine distribution tray stocker according to an embodiment of the present disclosure;

FIG. 7A-b is a plan view of the main part of the medicine-distribution-tray lateral mover of FIG. 7A-a;

FIG. 7B-a is a plan view illustrating the configuration and operation of the main part of the medicine-distribution-tray lateral mover of the medicine distribution tray stocker according to an embodiment of the present disclosure;

FIG. 7B-b is a plan view of the main part of the medicine-distribution-tray lateral mover of FIG. 7B-a;

FIG. 8A-a is a front view of a container according to an embodiment of the present disclosure;

FIG. 8A-b is a cross-sectional side view of the container of FIG. 8A-a;

FIG. 8B-a is a cross-sectional front view of the periphery of a partition of a container according to an embodiment of the present disclosure;

FIG. 8B-b is a cross-sectional front view of the container, illustrating an operation of adjusting the position of the partition of the container of FIG. 8B-a FIG. 9A is a cross-sectional plan view of a main part of an attachment and detachment mechanism of a container provided in one of a plurality of drawers of a medication support apparatus according to an embodiment of the present disclosure;

FIG. 10A-a is a front view of a take-out device of a medication support apparatus according to an embodiment of the present disclosure;

FIG. 10A-b is a plan view of the take-out device of FIG. 10A-a;

FIGS. 10B-a, 10B-b, 10B-c, 10B-d, and 10B-e are front views illustrating an operation of a take-out device of a medication support apparatus according to an embodiment of the present disclosure;

FIGS. 10C-a, 10C-a', 10C-b, 10C-c, 10C-d, and 10C-e are front views illustrating an operation of a take-out device of a medication support apparatus according to an embodiment of the present disclosure;

FIGS. 16A1, 16A2, 16A3, 16B, and 16C are diagrams illustrating a main overall operation flow of the medication support apparatus of FIG. 1 according to an embodiment of the present disclosure;

FIG. 21 is a diagram illustrating a "basic information" screen displayed on a touch panel of a medication support apparatus according to an embodiment of the present disclosure;

FIG. 22 is a diagram illustrating a "medication information" screen displayed on a touch panel of a medication support apparatus according to an embodiment of the present disclosure;

FIG. 23 is a diagram illustrating a "medication information (container)" screen displayed on a touch panel of a medication support apparatus according to an embodiment of the present disclosure;

FIG. 24 is a diagram illustrating a "medicine information (medicine distribution tray)" screen displayed on a touch panel of a medication support apparatus according to an embodiment of the present disclosure;

FIG. 25 is a diagram illustrating a "medication information" screen displayed on a touch panel of a medication support apparatus according to an embodiment of the present disclosure;

FIG. 26 is a diagram illustrating a "registration OK" screen displayed on a touch panel of a medication support apparatus according to an embodiment of the present disclosure;

FIG. 27 is a diagram illustrating a "registration information confirmation (container and tray)" screen displayed on a touch panel of a medication support apparatus according to an embodiment of the present disclosure;

FIG. 28 is a diagram illustrating a "confirmation of registration information (medication timing)" screen displayed on a touch panel of a medication support apparatus according to an embodiment of the present disclosure;

FIG. 29 is a diagram illustrating a "change and delete" screen displayed on a touch panel of a medication support apparatus according to an embodiment of the present disclosure;

FIG. 32 is a diagram illustrating a "confirmation of container information" screen displayed on a touch panel of a medication support apparatus according to an embodiment of the present disclosure;

FIG. 33 is a diagram illustrating an "add or delete" screen displayed on a touch panel of a medication support apparatus according to an embodiment of the present disclosure;

FIG. 34 is a diagram illustrating an "add or delete" screen displayed on a touch panel of a medication support apparatus according to an embodiment of the present disclosure;

FIG. 36 is a diagram illustrating a screen displayed on a touch panel of a medication support apparatus when "Confirm medicine distribution tray information" in FIG. 35 is selected according to an embodiment of the present disclosure;

FIG. 37 is a diagram illustrating a screen displayed on a touch panel of a medication support apparatus when "change medicine distribution time" in FIG. 35 is selected according to an embodiment of the present disclosure;

FIG. 38 is a diagram illustrating a screen displayed on a touch panel of a medication support apparatus when "change of medicine distribution time" in FIG. 35 is selected according to an embodiment of the present disclosure;

FIG. 39A is a front view of an overall configuration of a medication support apparatus of FIG. 1 according to a variation of the present disclosure;

FIG. 39B is a side view of the medication support apparatus of FIG. 39A according to an embodiment of the present disclosure;

FIG. 41 is a diagram illustrating a "Forced Medicine Distribution (tray)" screen displayed on a touch panel of a medication support apparatus according to an embodiment of the present disclosure;

FIG. 43 is a diagram illustrating a "Forced Medicine Distribution (Single tray)" screen displayed on a touch panel of a medication support apparatus according to an embodiment of the present disclosure;

FIG. 46 is a diagram illustrating a "Forced Medicine Distribution (Single tray)" screen displayed on a touch panel of a medication support apparatus according to an embodiment of the present disclosure;

Figure 2B:
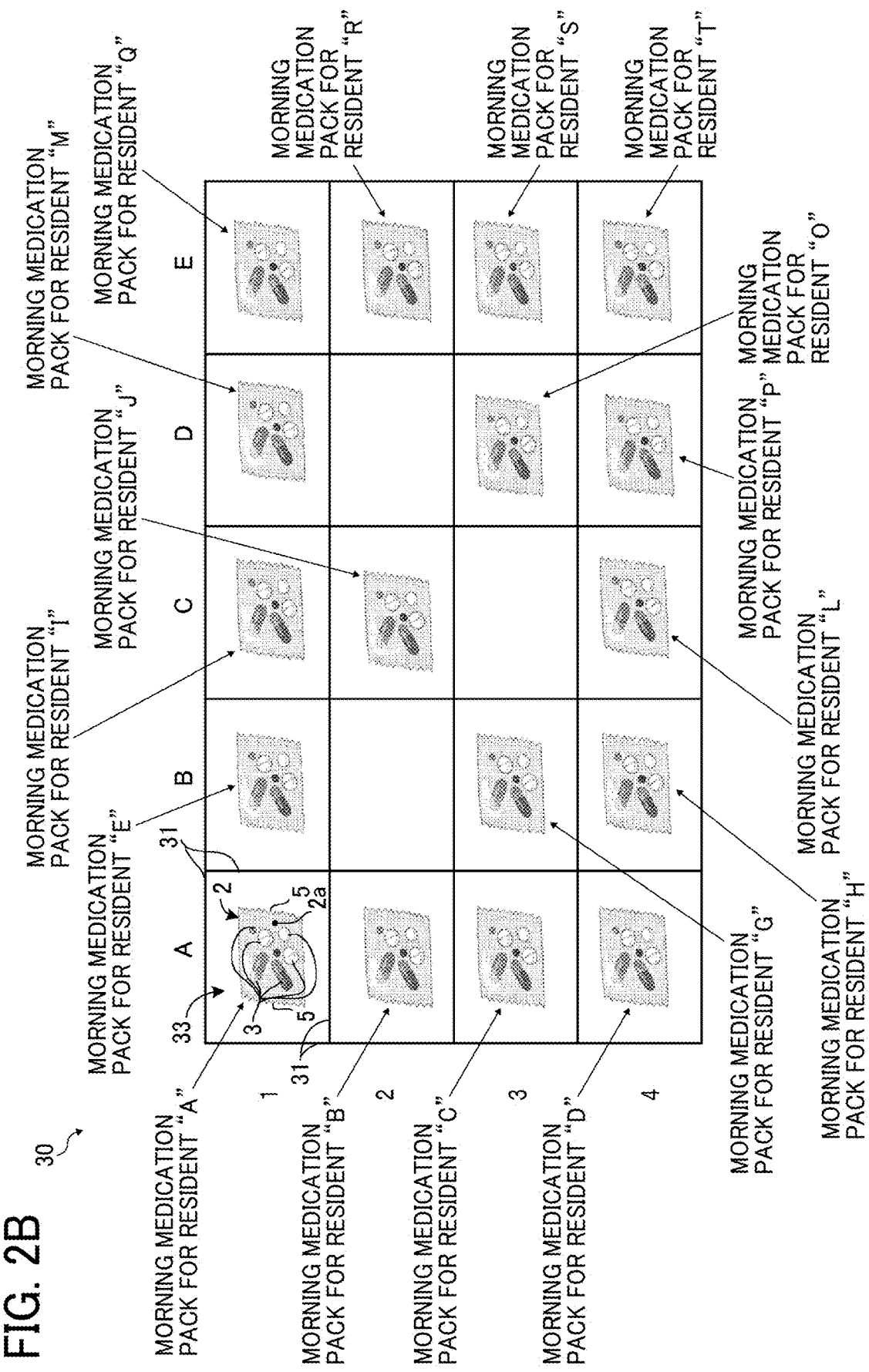
FIG. 2B is a plan view of the medicine distribution tray of a medication support apparatus according to Example 1 of the present disclosure.

The accompanying drawings are intended to depict embodiments of the present disclosure and should not be interpreted to limit the scope thereof. The accompanying drawings are not to be considered as drawn to scale unless explicitly noted.

DETAILED DESCRIPTION

In describing embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner and achieve similar results.

Although the embodiments are described with technical limitations with reference to the attached drawings, such description is not intended to limit the scope of the disclosure and all of the components or elements described in the embodiments of this disclosure are not necessarily indispensable.

Referring now to the drawings, embodiments of the present disclosure are described below. In the drawings for explaining the following embodiments, the same reference codes are allocated to elements (members or components) having the same function or shape and redundant descriptions thereof are omitted below.

Hereinafter, a detailed description is given of embodiments of the present disclosure with reference to the drawings. Elements (for example, mechanical parts and components) having the same functions and shapes are denoted by the same reference numerals throughout the embodiments and variations of the present disclosure and redundant descriptions are omitted.

With reference to FIGS. 1A and 1B, a main configuration of an entire medication support apparatus according to an embodiment of the present disclosure is described. FIG. 1A is a front view schematically illustrating a main configuration of the entire medication support apparatus. FIG. 1B is a side view of the medication support apparatus schematically, illustrating a side configuration of the medication support apparatus of FIG. 1A. As illustrated in FIG. 1, a medication support apparatus 200 according to an embodiment of the present disclosure includes a plurality of containers 10 as containers that stores one-dose packages of medicines (hereinafter also simply referred to as "packs"), and a medicine distribution tray 30 as a medicine distribution member or tray having a plurality of partitions (described later) in which specific packs are placed. Hereinafter, a location on which the medicine distribution tray 30 is placed (a location to which a pack is delivered such that the pack is automatically distributed to the medicine distribution tray 30) is referred to as a medicine distribution unit 29. In FIG. 1, the front-rear direction of the medication support apparatus 200 is defined as an X direction, a lateral direction thereof is defined as a Y direction, and a vertical direction thereof is defined as a Z direction.

The medication support apparatus 200 also includes a first port 41, a second port 42, a third port 43, and a fourth port 44 as ports that allow the medicine distribution tray 30 to enter and exit a body frame 199 as an apparatus body, a take-out device 50 as a take-out device that takes out a specific pack from the container 10, and a transfer device 90 as a transfer device that transfers the pack taken out from the container 10.

The medication support apparatus 200 also includes a medicine distribution tray stocker 45 as a medicine-distribution-member stocker that stores the plurality of medicine distribution trays 30. The medicine distribution tray stocker 45 includes a medicine-distribution-tray vertical mover 82 as a medicine-distribution-member vertical mover that moves the medicine distribution tray 30 in the Z direction. A detailed configuration of the medicine distribution tray stocker 45 will be described later.

The container 10 is inserted into and set in the body frame 199 through the third port 43 and the fourth port 44. Opening and closing doors of the third port 43 and the fourth port 44 are opened to draw out a drawer 21 in which the container 10 is set. Thus, the container 10 is attached and detached.

The first port 41 allows the medicine distribution trays 30 to be collectively taken out or inserted into the body frame 199. The second port 42 is provided so that the pack can be removed immediately after being placed (hereinafter also referred to as "set" or "inserted") in the medicine distribution tray 30.

EXAMPLE 1

First, the medicine distribution tray 30 is described with reference to FIGS. 2A, 2B, 2C, 2D, and 2E. FIG. 2A is an external perspective view of the configuration of the medicine distribution tray 30. FIGS. 2B, 2C, 2D, and 2E are plan views illustrating Example 1 in which a plurality of sections of the medicine distribution tray 30 are allocated to each medicine taker.

As illustrated in FIG. 2A, the medicine distribution tray 30 includes partition walls 31 as partitions as a plurality of partitions that arranges specific packs, and is partitioned by each set of the four standing partitions 31. In the example illustrated in FIG. 2A, the medicine distribution tray 30 includes a total of twenty compartments 33 divided by a plurality of partitions 31. That is, the medicine distribution tray 30 arranges a specific pack in a predetermined (specific) compartment 33 as a predetermined location partitioned by a plurality of partitions 31.

The twenty compartments 33 of the medicine distribution tray 30 can be described as elements of a matrix consisting of five columns A, B, C, D and E in the vertical direction (line feed direction) and four rows 1, 2, 3, and 4 in the horizontal direction (character feed direction). Thus, each of the twenty compartments 33 of the medicine distribution tray 30 can be uniquely positioned by a component (hereinafter also referred to as an address) of a matrix of five columns and four rows. The medicine distribution tray 30 further includes a bottom wall 32 on which arranged packs are placed. In this manner, in the medicine distribution tray 30, the plurality of (four) partitions 31 and the common bottom wall 32 ensure that a specific pack placed in a specific compartment 33 is placed in the specific compartment 33 so as not to be mixed with packs in other compartments 33 or to be dropped from the bottom wall 32 (this also applies to Examples 2 and 3 described later).

"Floor A: After breakfast: Medicine distribution tray" displayed on a front outer wall surface of the medicine distribution tray 30 illustrated in FIG. 2A indicates that packs to be taken after breakfast (in the morning) by a plurality of medicine takers living on the same floor A in, for example, a care facility, are placed in the medicine distribution tray 30.

As illustrated in FIG. 2B with "A1" as one of the compartments 33 as a specific compartment as a representative compartment, a pack 2 according to an embodiment of the present disclosure includes for a bag 2a and a leakage preventing member. The bag 2a covers a drug 3 such as a capsule or a tablet which is divided into small portions and packed in a transparent or semi-transparent bag made of a resinous film. The leakage preventing member (a portion at which usually two or three sides of a bag are compressed) prevents the drug 3 from leaking from the bag 2a. One pack 2 is usually a unit dose of each administration of medicine for a medicine taker.

Two or more packs that are connected in a band shape are referred to as a pack continuous body. The pack continuous bodies sold or provided to medicine takers in pharmacies or the like are usually in a single form. However, the pack described in embodiments of the present disclosure is one (single) pack separated from the pack continuous body.

One pack in which a same medicine is sealed is illustrated to simplify the description in the description below. However, it is needless to say that packs in which different medicines are sealed may be used depending on the use and purpose of medicine takers.

Note that among packs illustrated in FIGS. 2B, 2C, 2D, and 2E, FIGS. 3A, 3B, 3C, and 3D, FIG. 4, and the like that illustrate Examples described later, only the pack placed in any one specific compartment (for example, A1 in FIGS. 2B, 2C, 2D, and 2E) is denoted by the reference numeral "2", and the packs placed in other compartments are not denoted by the reference numeral "2" to simplify drawings.

The medicine distribution tray 30 illustrated in FIG. 2B includes a total of twenty compartments 33 divided by a plurality of partitions 31. Positions at which the compartments 33 are set and inserted on the medicine distribution tray 30 are determined depending on the pack to be taken by each medicine taker. In other words, the plurality of compartments 33 in the medicine distribution tray 30 are allocated to the plurality of medicine takers (twenty medicine takers of A to T), respectively, at a same medication timing.

Specifically, the medicine distribution tray 30 for morning administration illustrated in FIG. 2B is divided into compartments 33 (locations positioned by matrix components) allocated for twenty medicine takers, respectively. For example, the compartment 33 of A1 is allocated to a morning medicine pack for the medicine taker A (described as "morning medicine pack for resident A" at A1 in FIG. 2B), the compartment 33 of A2 is allocated to a morning medicine pack for the medicine taker B (described as "morning medicine pack for resident B" at A2 in FIG. 2B), the compartment 33 of A3 is allocated to a morning medicine pack for the medicine taker C, and similarly, and the compartment 33 of E4 is allocated to a morning medicine pack for the medicine taker T. In this case, the medicine distribution tray 30 itself is used for morning administration. Note that although the compartments 33 corresponding to the respective specific packs are illustrated (for example, B2 indicates the compartment corresponding to the pack taken in the morning by the medicine taker F, C3 indicates the compartment corresponding to the pack taken in the morning by the medicine taker K, and D2 indicates the compartment corresponding to the pack taken in the morning by the medicine taker N). However, some corresponding packs are not distributed as collectively described with the medicine distribution tray 30 for noon illustrated in FIG. 2C described later.

In some cases, a specific medicine taker does not take medicine at a specific timing. For example, in the medicine distribution tray 30 for noon illustrated in FIG. 2C, when the pack for noon administration of the medicine taker B is not necessary, the pack for noon administration of the medicine taker B is not placed in the compartment 33 of A2. Similarly, if the medicine taker D does not need a pack for noon time medication, the pack for the medicine taker D for noon time medication is not placed in the compartment 33 of A4. In the same manner, if there is no need for corresponding packs, no corresponding packs are placed in the compartments 33. A pack to be taken by the medicine taker E, a pack to be taken by the medicine taker F, a pack to be taken by the medicine taker H, a pack to be taken by 4, medicine taker K, a pack to be taken by the medicine taker N, a pack to be taken by the medicine taker P, a pack to be taken by the medicine taker Q, and a pack to be taken by the medicine taker T are not placed in the compartments 33 of B1, B2, B4, C3, D2, D4, E11 E4, respectively.

Figure 2C:
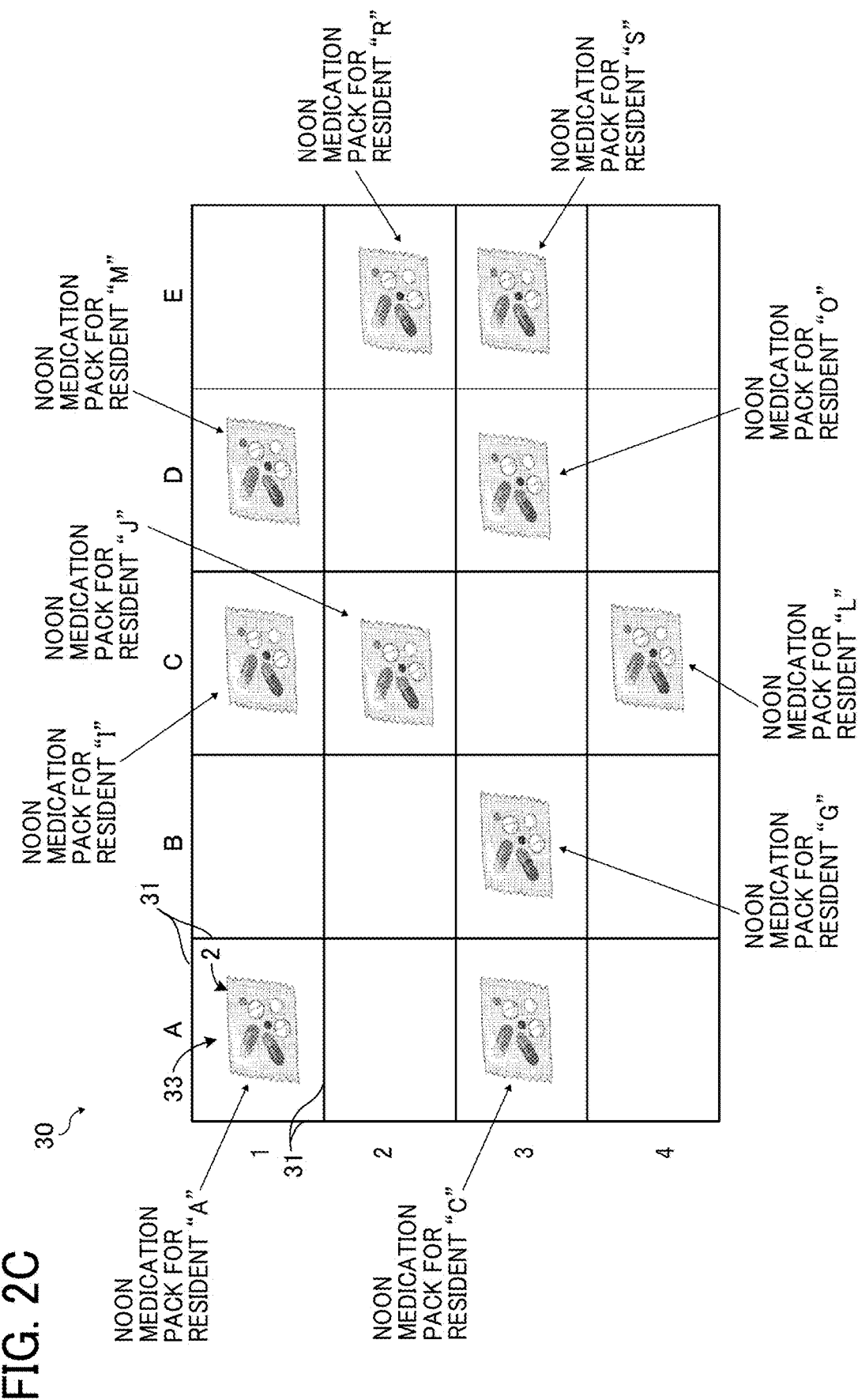
FIG. 2C is a plan view of the medicine distribution tray according to Example 1 of the present disclosure.

A pack to be taken by each medicine taker at a same medication timing is determined for each of the medicine distribution trays 30 to be used for the timing in the same manner as described in FIG. 2C. For example, in the medicine distribution tray 30 for evening illustrated in FIG. 2D, when a pack for medication in evening is not necessary for the medicine taker C, it is determined that the pack for the medicine taker C for evening is not placed in the compartment 33 of A3.

Figure 2D:
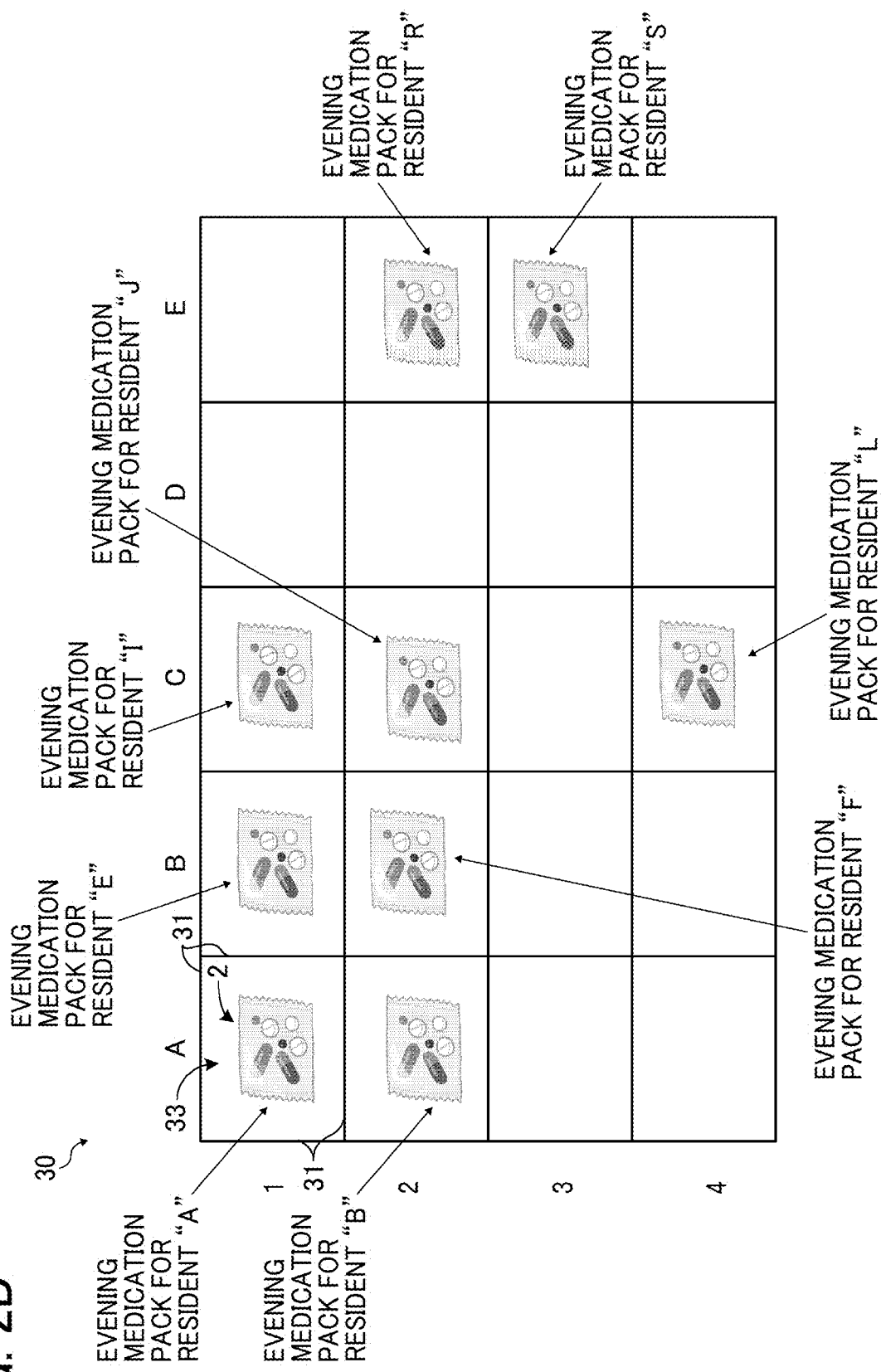
FIG. 2D is a plan view of the medicine distribution tray according to Example 1 of the present disclosure.

Similarly as in FIG. 2D, for example, in the medicine distribution tray 30 for bedtime illustrated in FIG. 2E, when a pack for medication is not required before the medicine taker C sleeps, it is determined that the pack for bedtime of the medicine taker C is not placed in the compartment 33 of A3 for each of the medicine distribution trays 30.

In the medicine distribution tray 30 of Example 1 illustrated in FIGS. 2B, 2C, 2D, and 2E, a specific pack 2 is distributed in a specific compartment 33 as a predetermined location partitioned by a plurality of partitions 31, and the plurality of compartments 33 of the medicine distribution tray 30 are allocated to the medicine takers, respectively, at the same medication timing.

According to Example 1, each of the compartments 33 is designated to a medicine taker. Accordingly, a staff member or the like (including pharmacists, nurses, care givers, or medication supporters) of, for example, a care facility performing medication support or the like with the medicine distribution tray 30 can take a medicine for each medicine taker from the same compartment 33 (address) at each time of performing medication. Thus, medication errors can be prevented. In other words, the location of each of the compartments 33 designated to a medicine taker does not change day by day, the workload of the staff members or the like in the care facility, the welfare facility, or the like can be reduced.

EXAMPLE 2

The medicine distribution tray 30 according to Example 2 is described with reference to FIGS. 3A, 3B, 3C, and 3D. FIGS. 3A, 3B, 3C, and 3D are plan views illustrating Example 2 in which a plurality of compartments 33 of the medicine distribution tray 30 are allocated for a plurality of medication timings, respectively, of each of the medicine takers. The configuration of the medicine distribution tray 30 is not limited to the configuration described in Example 1 illustrated in FIGS. 2B, 2C, 2D, and 2E. For example, the medicine distribution tray 30 may be configured such that the plurality of compartments 33 of the medicine distribution tray 30 are allocated to the plurality of medication timings of each medicine taker as in Example 2 illustrated in FIGS. 3A, 3B, 3C, and to 3D.

Figure 3A:
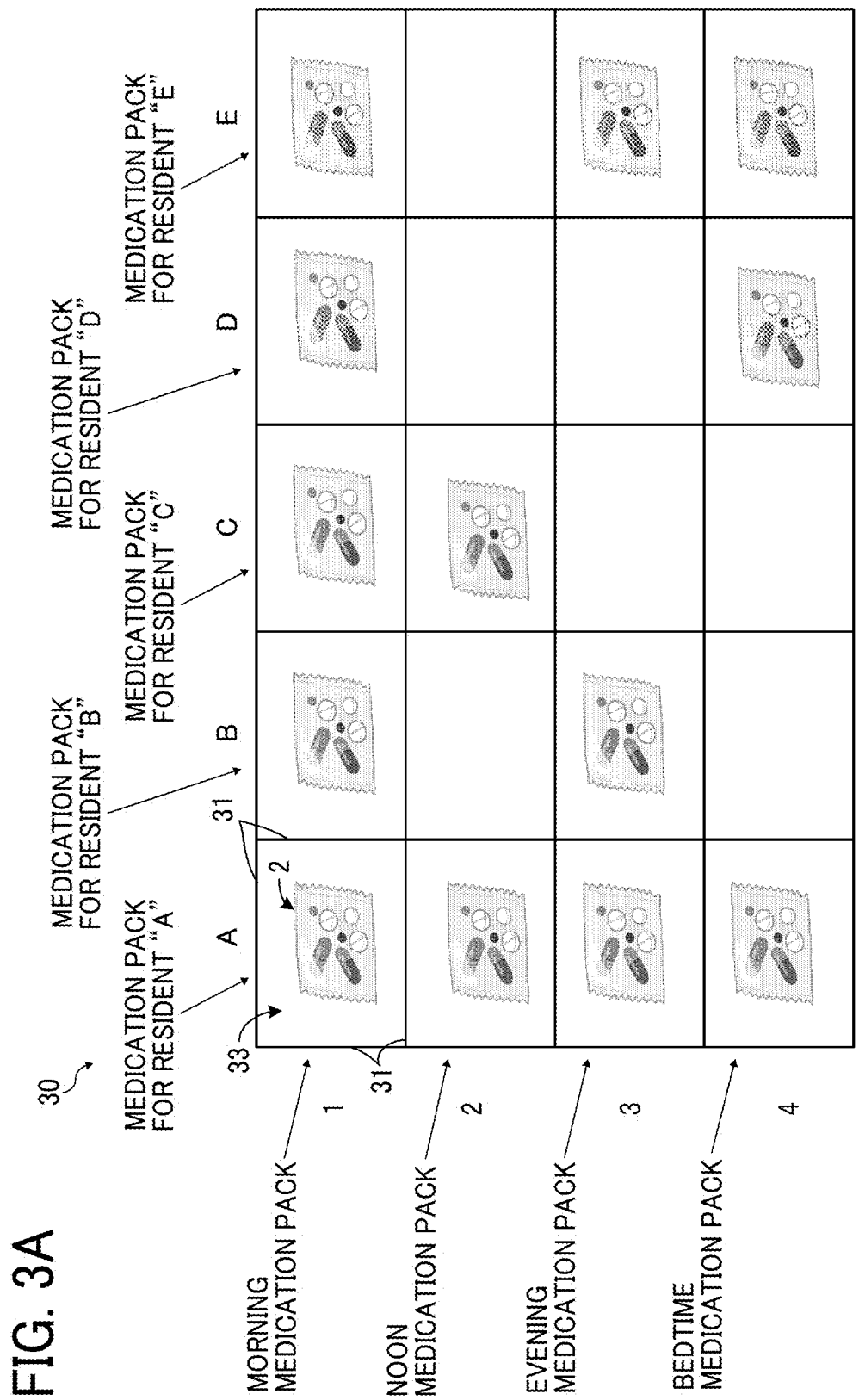
FIG. 3A is a plan view of the medicine distribution tray according to Example 2 of the present disclosure.

In the medicine distribution tray 30 illustrated in FIG. 3A, a plurality of compartments 33 are allocated for a plurality of medication timings, respectively, of the packs 2 to be taken in the morning, noontime, evening, and bedtime, and for each of the medicine takers A to E. For example, an empty compartment 33 of 2B in which the pack for noontime is not placed indicates a case in which the pack for noontime of medicine taker B is not necessary.

In the medicine distribution tray 30 illustrated in FIG. 3B, a plurality of compartments 33 are allocated for each medication timing of the packs 2 to be taken in the morning, noontime, evening, and bedtime, and for each of the medicine takers F to J. For example, a compartment 33 of A1 in which a pack for morning is not placed, a compartment 33 of A2 in which a pack for afternoon is not placed, and a compartment 33 of A4 in which a pack for evening is not placed indicate a case in which no packs for the morning, afternoon, and evening of medicine taker F are not necessary.

In the medicine distribution tray 30 illustrated in FIG. 3C, a plurality of compartments 33 are allocated for a plurality of medication timings of the packs 2 to be taken in the morning, noontime, evening, and bedtime, respectively, and for each of the medicine takers K to O. For example, a compartment 33 of A1 in which a pack for morning is not placed, a compartment 33 of A2 in which a pack for afternoon is not placed, and a compartment 33 of A3 in which a pack for evening is not placed indicates a case in which packs for morning, afternoon, and evening of medicine taker K are not necessary.

Figure 3D:
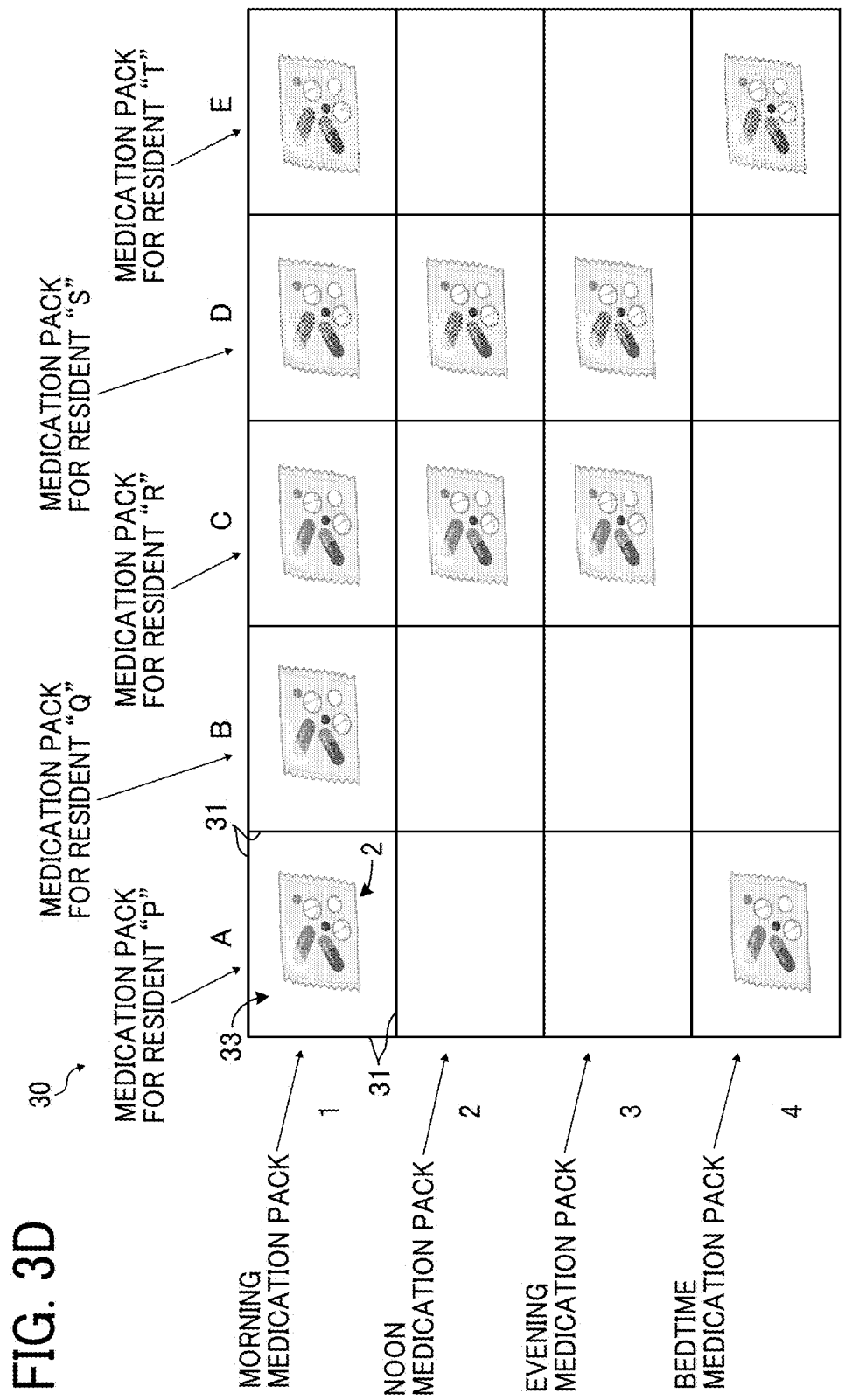
FIG. 3D is a plan view of the medicine distribution tray according to Example 2 of the present disclosure.

In the medicine distribution tray 30 illustrated in FIG. 3D, a plurality of compartments 33 are allocated for each medication timing of the packs 2 to be taken in the morning, noontime, evening, and bedtime, and for each of the medicine takers P to T. For example, a compartment 33 of A2 in which a pack for noontime is not placed and a compartment 33 of A3 in which a pack for evening is not placed indicate a case in which no packs for noontime and evening of medicine taker K are necessary.

In the medicine distribution trays 30 illustrated in FIGS. 3A, 3B, 3C, and 3D, the medicine distribution trays 30 are managed in units of floor or in units of room in which a plurality of medicine takers who reside, and packs 2 for the day (or several days) are distributed to the medicine distribution trays 30 in advance.

In the medicine distribution tray 30 of Example 2 illustrated in FIGS. 3A, 3B, 3C, and 3D, a specific pack 2 is placed in a specific compartment 33 as a predetermined location partitioned by a plurality of partitions 31, and the plurality of compartments 33 of the medicine distribution tray 30 are allocated for a plurality of medication timings, respectively, of each individual medicine taker.

According to Example 2, the plurality of compartments 33 are allocated for a plurality of medication timings such as morning, noontime, evening, and bedtime. Thus, performing medication for each medicine taker at a wrong timing can be prevented.

EXAMPLE 3

Figure 4:
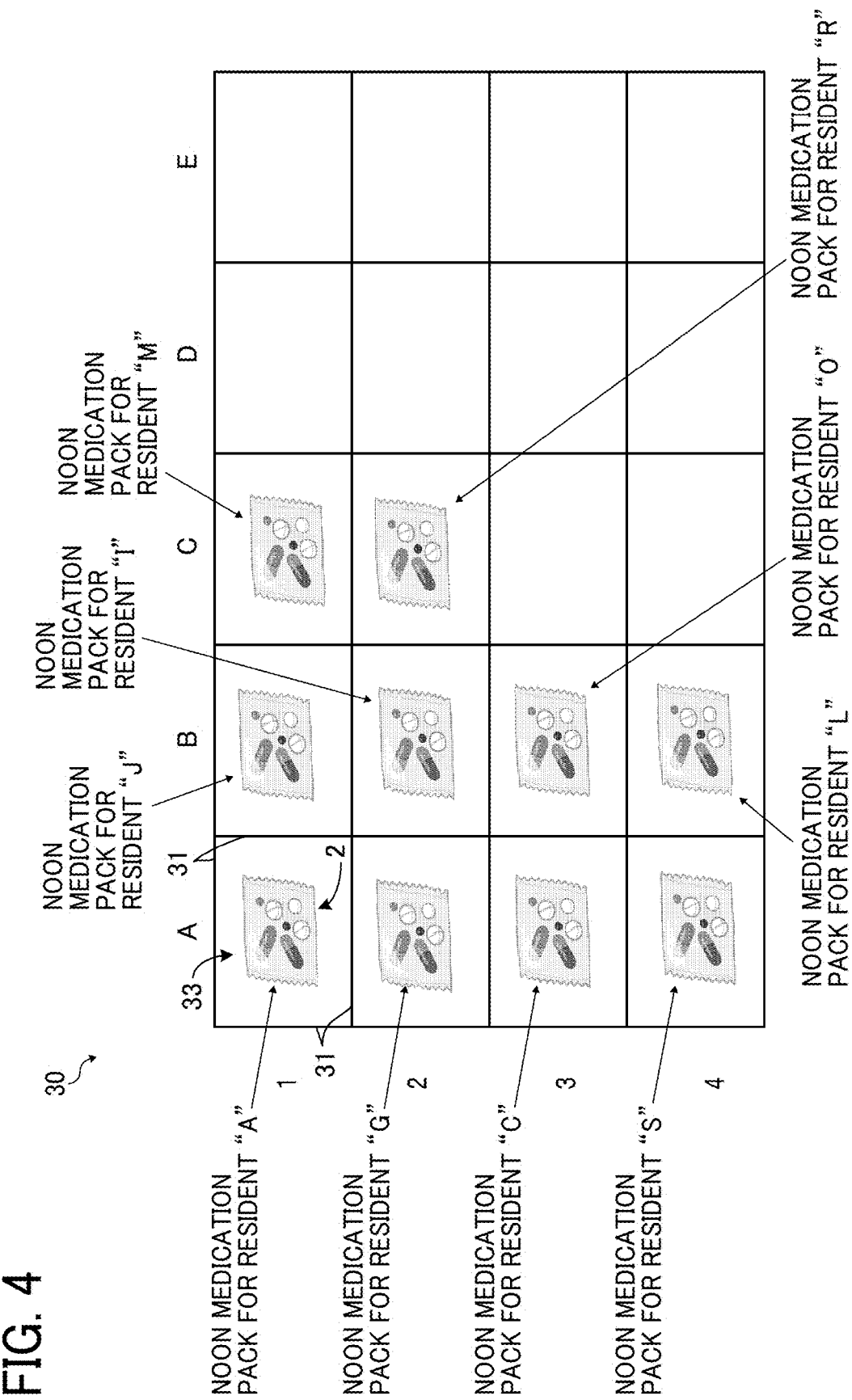
FIG. 4 is a plan view of a medicine distribution tray according to Example 3 of the present disclosure.

With reference to FIG. 4, a medicine distribution tray 30 according to Example 3 is described. FIG. 4 is a plan view of the medicine distribution tray 30 according to Example 3. The plurality of compartments 33 of the medicine distribution tray 30 illustrated in FIG. 4 are arranged in the order of medication from the top of the medicine distribution tray 30. Specifically, the arrangement of the compartments 33 on the medicine distribution tray 30 is as follows. A pack 2 for noontime of a medicine taker A is placed in a compartment 33 of A1 positioned at an upper end of the medicine distribution tray 30 in FIG. 4. a pack 2 for noontime of a medicine taker G is placed in a compartment 33 of A2. a pack 2 for noontime of a medicine taker C is placed in a compartment 33 of A3, and the pack 2 for noontime of medicine taker S is placed in a compartment 33 of A4. At this time, the order of medication is determined in advance in the order of the medicine taker A, the medicine taker G, the medicine taker C, and the medicine taker S.

In the medicine distribution tray 30 illustrated in FIG. 4, when the same medicine distribution tray 30 is used, there is empty compartments 33 which are not used in compartments 33 of C3 to E4 in which the packs 2 are not distributed. In this case, no packs are placed in the empty compartments 33 which are not used. The unused empty compartments 33 may be used as a place to place a medicine to be taken in common among the medicine takers or other medication assistance equipment (such as a towel, a spoon, and a sucker). In this case, care assistance equipment or the like may be set in advance even after the packs are distributed by the medication support apparatus.

When the order of medication is determined in advance as described above, the packs 2 are delivered to the medicine takers in order from the pack 2 placed in the compartment 33 at the endmost portion of the medicine distribution tray 30. Thus, erroneous delivery of a pack 2 to be delivered to another medicine taker can be prevented. According to Example 3, in a care facility or the like in which medicine takers taking medication in a predetermined order lives, the medicine takers who take medication, care staffs, or the like take packs in order from the end of the medicine distribution tray. Thus, an error due to mix-up of packs can be prevented.

Figure 6A:
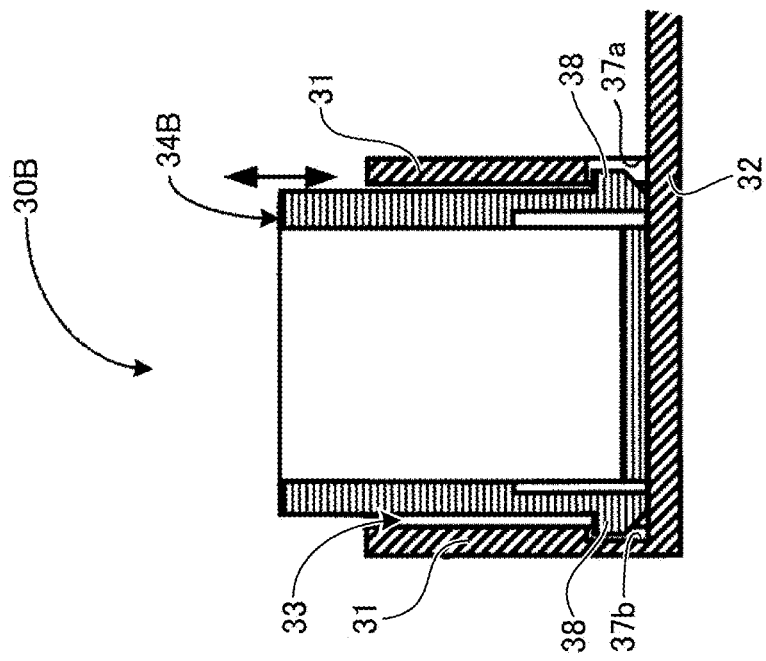
FIG. 6A is a cross-sectional view of a medicine distribution tray according to a variation of Examples 1, 2, and 3 of the present disclosure.
Figure 6B:
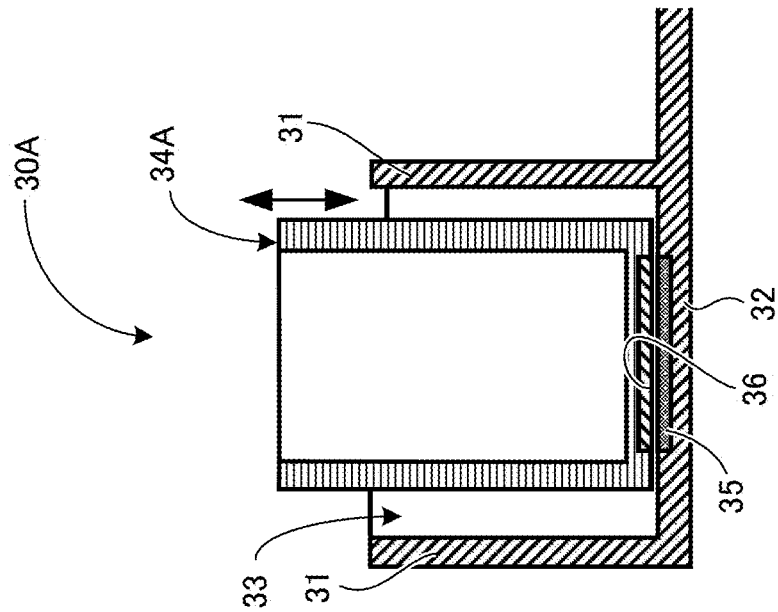
FIG. 6B is a cross-sectional view of a medicine distribution tray according to another variation of Examples 1, 2, and 3 of the present disclosure.

Variations of Examples 1, 2, and 3 are described with reference to FIGS. 5 and 6. FIG. 5 is an external perspective view of a medicine distribution tray 30A according to a variation. FIG. 6A is a cross-sectional view of the medicine distribution tray 30A according to the variation. FIG. 6B is a cross-sectional view of the medicine distribution tray 30A according to another variation different from the variation of FIG. 6A. In Examples 1, 2, and 3 described above, the configurations in which the packs are placed in the medicine distribution tray 30 or the medicine distribution tray 30A itself has been described. However, as illustrated in FIGS. 5 and 6, a variation in which a detachable smaller-size box is placed in the medicine distribution tray 30 or the medicine distribution tray 30A in advance may be employed.

The medicine distribution tray 30A according to the variation illustrated in FIGS. 5 and 6 is different from the medicine distribution tray 30 of Examples 1, 2, and 3 in that a subdivision box 34A as a detachable housing is provided in each compartment 33 (partitions 31 and a bottom wall 32) of the medicine distribution tray 30A and in that a pack 2 is placed in the subdivision box 34A.

The subdivision box 34A is integrally formed of, for example, resin, and a permanent magnet 36 is provided on an outer bottom wall surface of the subdivision box 34A. On the other hand, a metal plate 35 that attracts the permanent magnet 36 of the subdivision box 34A with each other as a ferromagnetic material is provided on the inner surface side of the bottom wall 32 constituting the compartment 33. Such an attachment and detachment mechanism (attaching and detaching device), the subdivision box 34A can be detached upward and held downward from the compartment 33 of the medicine distribution tray 30A. The permanent magnet 36 may be provided on the bottom wall 32 side, and the metallic plate 35 may be provided on the bottom wall surface of the subdivision box 34A.

A medicine distribution tray 30B according to another variation illustrated in FIG. 5 is different from the medicine distribution tray 30A in that the subdivision box 34B as a detachable housing is used in each of the compartments 33 (partitions 31 and a bottom wall 32) of the medicine distribution tray 30B instead of the subdivision box 34A. The subdivision box 34B is integrally formed of, for example, resin, and elastically deformable elastic fitting claws 38 are provided on both sides of the outer walls of the subdivision box 34B. On both sides of a lower portion of the partitions 31 constituting the compartment 33, there are provided a fitting hole 37a and a fitting hole 37b that are fitted to the elastic fitting claws 38 of the subdivision box 34B. The fitting hole 37a penetrates a lower side wall of the partition 31, and the fitting hole 37b is formed as a hole that does not penetrate the lower side wall of the partition 31. Such an attachment and detachment mechanism allows the subdivision box 34B to be detached upward and held downward from each of the compartments 33 of the medicine distribution tray 30B.

In the variations illustrated in FIGS. 5 and 6A and 6B, normally, a pack of medicine is given to a resident (a medicine taker) in a care facility or the like after a meal or before a meal, and residents gather in a dining room or the like in the care facility. If packs of medicines are taken together with a medicine distribution tray when packs of medicines are distributed to residents, it is assumed that there is no place for storing the medicine distribution tray or the medicine distribution tray becomes an obstacle at the time of medication assistance. Therefore, placing the medicine distribution tray 30A or the medicine distribution tray 30B according to the variations in a back yard of a dining room and removing the subdivision box 34A from the medicine distribution tray 30A or the subdivision box 34B from the medicine distribution tray 30B at the time of medication assistance allows to go to the residents without carrying a large object. Further, since the residents are identified when the subdivision box 34A or the subdivision box 34B is removed, the number of check steps increases. Thus, medication errors can be prevented.

As illustrated in FIG. 5, the name and room number of the resident (medicine taker) and other information that can identify the resident are attached in advance to the medicine distribution tray 30A and the medicine distribution tray 30B. Such an arrangement allows staff members or the like in a care facility or the like to check the medicine distribution status after the packs 2 are distributed by the medication support apparatus 200 (see FIG. 1), and to add or remove a pack (drug) depending on the status of the resident at that time in an easier manner. Equivalent effects can be obtained by adding the information of the residents to the subdivision boxes.

As the identification information of the resident, not only the characters illustrated in FIG. 5 but also a QR code (registered trademark), a barcode, a non-contact Integrated Circuit (IC) tag, or the like may be used from the viewpoint of privacy. In this case, reading a QR code, a barcode, an IC tag, or the like with a dedicated terminal (or application) allows to check the identity of the resident. Further, a number, a bar code, a QR code, or a non-contact IC tag may be attached to the medicine distribution tray so that the medicine distribution tray can be individually recognized.

According to the above-described variation, carrying the medicine distribution tray of Examples 1, 2, and 3 is not necessary. Medication assistance can be performed by a simpler operation of taking out the subdivision box 34A as a housing from the medicine distribution tray 30A or taking out the subdivision box 34B from the medicine distribution tray 30B and bringing the subdivision box 34B to the medicine taker. This also prevents mistakes of taking a wrong medicine distribution tray and prevents the packs placed on the medicine distribution tray from being scattered.

Variations of FIGS. 6A and 6B can be applied to the medicine distribution tray 30 according to any of Examples 1, 2, and 3. Note that the variation illustrated in FIG. 6 is applied to the Example 1 illustrated in FIG. 2C.

Figure 7C:
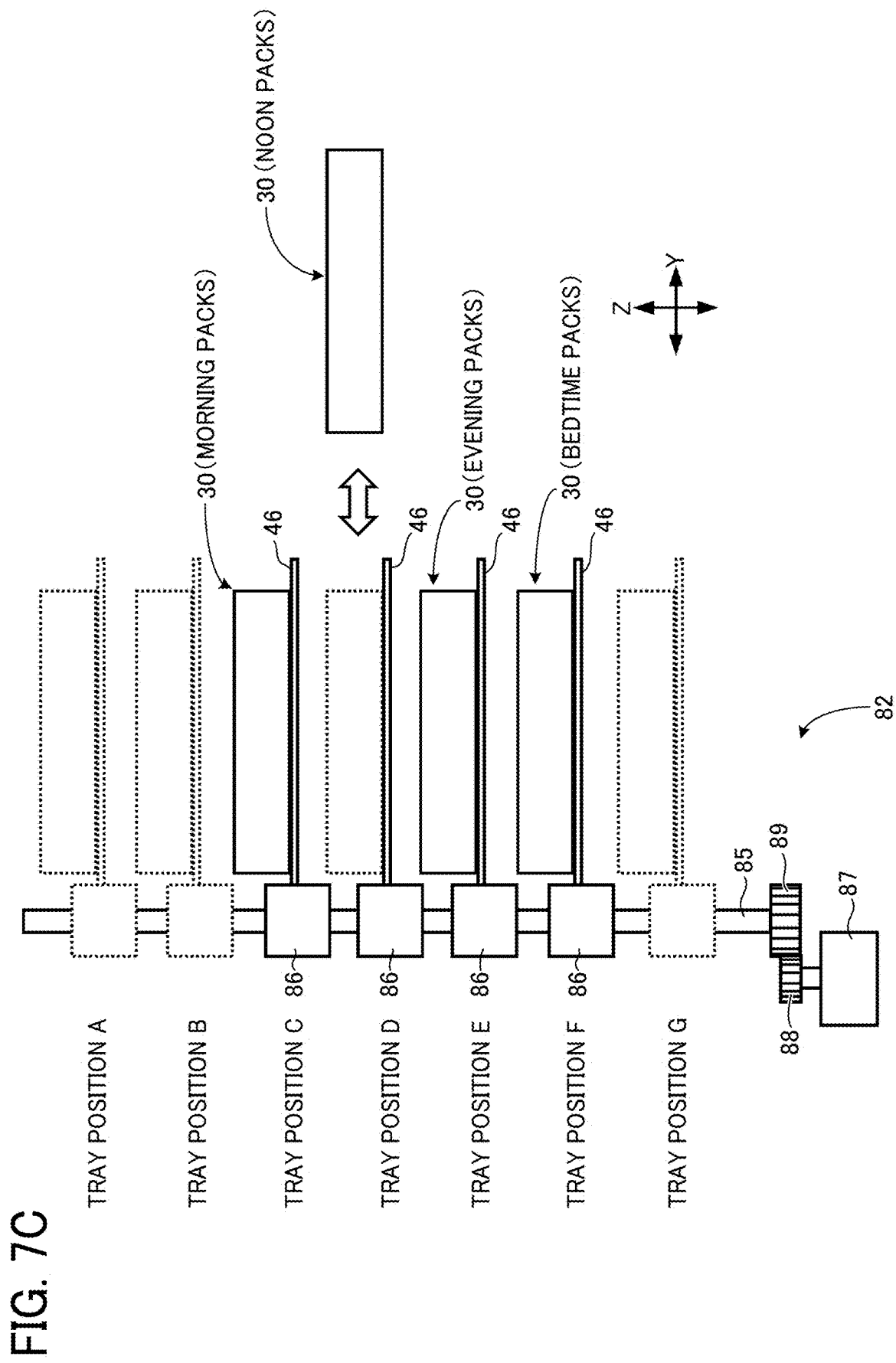
FIG. 7C is a front view illustrating a configuration and an operation of a main part of a medicine-distribution-tray vertical mover of a medicine distribution tray stocker according to an embodiment of the present disclosure.

With reference to FIGS. 7A, 7B, and 7C, a detailed configuration and operation of the medicine distribution tray stocker 45 in FIG. 1 is described. FIG. 7A-a and FIG. 7B-a are plan views of the configuration and operation of a main part of a medicine-distribution-tray lateral mover 70 provided in the medicine distribution tray stocker 45. FIG. 7A-b is a front view of the medicine-distribution-tray lateral mover 70 of FIG. 7A-a. FIG. 7B-b is a front view of the medicine-distribution-tray lateral mover 70 of FIG. 7B-a. FIG. 7C is a front view of the configuration and operation of a main part of the medicine-distribution-tray vertical mover 82 provided in the medicine distribution tray stocker 45. The medicine distribution tray stocker 45 includes the medicine-distribution-tray lateral mover 70 as a medicine-distribution-member lateral mover that selects one medicine distribution tray 30 from the medicine distribution tray stocker 45 in which a plurality of medicine distribution trays 30 are stored and moves the selected medicine distribution tray 30 in the Y direction. The medicine distribution tray stocker 45 includes medicine-distribution-tray stocker bottom plates 46 on which the medicine distribution trays 30 are placed. A pair of notches 46a and 46b are formed in each of the medicine-distribution-tray stocker bottom plates 46. The pair of notches 46a and 46b prevent interference in the Z direction with a pair of arms 71a and 71b described later, which sandwich the medicine distribution tray 30, and allow the medicine distribution tray 30 in a state being sandwiched by the pair of arms 71a and 71b to move in the Z direction.

As illustrated in FIGS. 7A-a and 7A-b, one medicine distribution tray 30 is placed on a flat bottom plate 39. The medicine-distribution-tray lateral mover 70 includes a pair of arms 71a and 71b, an arm holder 72, and arm couplers 73a and 73b. The pair of arms 71a and 71b holds left and right ends of the medicine distribution tray 30 placed on the bottom plate 39. The arm holder 72 holds the arms 71a and 71b. The arm couplers 73a and 73b connect the arms 71a and 71b to the end portions of the arm holder 72. The medicine-distribution-tray lateral mover 70 also includes guides 74a and 74b, a guide rod 75, and the arm couplers 73a and 73b. The guides 74a and 74b are fixed to left and right ends of an arm holder 72, respectively, formed with a through hole. The guide rod 75 penetrates the holes of the guides 74a and 74b to integrally move and guide the pair of arms 71a and 71b, the arm holder 72, and the arm couplers 73a and 73b in the lateral direction Y. The medicine-distribution-tray lateral mover 70 includes a medicine-distribution-tray lateral moving mechanism that integrally moving the pair of arms 71a and 71b, the arm holder 72, and the arm couplers 73a and 73b in the lateral direction Y.

The medicine-distribution-tray lateral moving mechanism includes an endless belt 78, a belt grip 78a, a pulley gear 81, and a lateral movement motor 79. The endless belt 78 is wound around a driving pulley 76 and a driven pulley 77. The belt grip 78a integrally connects the belt 78 and the arm holder 72. A pulley gear 81 is fixed to a shaft of the driving pulley 76. The lateral movement motor 79 is fixed to the body frame 199 and includes a motor gear 80 fixed to an output shaft of the medicine distributing tray. The motor gear 80 meshes with the pulley gear 81. The lateral movement motor 79 is a control target driver of the medicine-distribution-tray lateral mover 70 (see FIG. 13 described later). The lateral movement motor 79 is preferably a stepping motor driven by pulse input from the viewpoint of accurate drive control. However, the lateral movement motor 79 may be a direct current (DC) motor or the like. The same applies to motors that are drivers of corresponding driving mechanisms described later.

As illustrated in FIGS. 7A-a and 7A-b, when the lateral movement motor 79 rotates in the counterclockwise direction in a state in which both ends of the medicine distribution tray 30 are sandwiched by the arms 71a and 71b, the drive pulley 76 and the belt 78 are rotationally driven in the clockwise direction via the rotation transmission of the pulley gear 81 meshing with the motor gear 80. As a result, the pair of arms 71a and 71b, the arm holder 72, and the arm couplers 73a and 73b are integrally moved together, and the guides 74a and 74b are moved in a leftward direction indicated by a thick arrow in FIG. 7A-a in accordance with the movement of the belt 78 while being guided by the guide rod 75.

After packs are placed on the medicine distribution tray 30 (see Examples 1, 2, and 3 described above), an operation of moving the medicine distribution tray 30 to the medicine distribution tray stocker 45 is performed. Note that the medicine distribution tray 30 illustrated in FIGS. 7B-a and 7B-b is in a state in which the medicine distribution tray 30, placed on the bottom plate 39 in a state of being sandwiched by the arms 71a and 71b, has moved to a predetermined position at which the medicine distribution tray 30 is delivered onto the medicine-distribution-tray stocker bottom plate 46 by the above-described operation in FIGS. 7A-a and 7A-b.

The medicine distribution tray 30 being located at a predetermined position on the bottom plate 39 in the medicine distribution unit 29 in FIG. 7A is grasped by a medicine-distribution-tray detection sensor 131 (illustrated only in the block diagram of FIG. 13 described later). The medicine distribution tray 30 having moved to a predetermined position on the medicine-distribution-tray stocker bottom plate 46 of the medicine distribution tray stocker is grasped by a medicine-distribution-tray detection sensor 130 (illustrated in the block diagram of FIG. 13 described later) disposed in the medicine distribution tray stocker 45.

As illustrated in FIGS. 7A-a, 7A-b, 7B-a, 7B-b, and 7C, the medicine-distribution-tray vertical mover 82 includes four guides 86 (illustrated by solid lines) and a drive rod 85 (illustrated by solid lines). The four guides 86 have a spiral concavo-convex groove shape (screw shape) formed on the inner peripheral portion of the guides 86 and the medicine-distribution-tray stocker bottom plate 46 is fixed by the four guides 86. The drive rod 85, which has a spiral concavo-convex groove shape (screw shape) on the outer peripheral portion, is fixed to the medicine-distribution-tray stocker bottom plate 46 and placed at a predetermined distance from the guides 86 in the X direction. Each of the four guides 84 has a substantially cubic shape, and is movable in the Z direction on a drive rod 85 serving as a drive guide via engagement between the above-described helical concavo-convex groove shaped portions (screw shapes).

The medicine-distribution-tray vertical mover 82 also includes the four guides 84 and the guide rod 83. Each of the medicine-distribution-tray stocker bottom plates 46 is fixed to corresponding one of the four guides 84 and a spiral concavo-convex groove shape is not formed on the inner peripheral portion of each of the four guides 84. Each of the medicine-distribution-tray stocker bottom plates 46 is fixed to corresponding one of the four guide rods 83 and is placed at a predetermined distance from corresponding one of the guides 84 in the X direction and the spiral concavo-convex groove shape is not formed on the outer peripheral portion of each of the four guide rods 83. The four guides 84 have a substantially cubic shape and are movable in the Z direction through engagement with the guide rods 83 serving as guides.

The medicine-distribution-tray vertical mover 82 includes a medicine-distribution-tray vertical movement mechanism that moves the four guides 84 to fix the medicine-distribution-tray stocker bottom plates 46 and four guides 86 to fix the medicine-distribution-tray stocker bottom plates 46 in the Z direction.

The medicine-distribution-tray vertical movement mechanism includes a vertical movement motor 87 and a drive rod gear 89. The vertical movement motor 87 is fixed to the body frame 199 and has a drive gear 88 on an output shaft of the vertical movement motor 87. The drive rod gear 89 is fixed to the drive rod 85 and constantly meshed with the drive gear 88. The vertical movement motor 87 is a control target driver of the medicine-distribution-tray vertical mover 82 (see FIG. 13 described later). As the vertical movement motor 87, for example, a stepping motor driven by pulse input or the like is used.

In FIG. 7C, when the vertical movement motor 87 is rotationally driven in a predetermined direction, the driving rod 85 is rotated in a direction opposite to the predetermined direction via the driving force transmission of the driving rod gear 89 meshing with the driving gear 88. Thus, each guide 86 is moved in upward or downward along the Z direction via the engagement between the spiral convex-concave groove shapes (screw shapes). At this time, as illustrated in FIG. 7C, each medicine distribution tray 30 on the medicine-distribution-tray stocker bottom plate 46 is moved to the position of each medicine distribution tray 30 (in FIG. 7C, "tray positions A, B, C, D, E, F, and G" are illustrated). In the example illustrated in FIG. 7C, the medicine-distribution-tray stocker bottom plate 46 on which the medicine distribution tray 30 on which packs to be taken in the morning are placed is moved to the tray position C, the medicine-distribution-tray stocker bottom plate 46 on which the medicine distribution tray 30 on which packs to be taken in the noontime are placed is moved to the tray position D, the medicine-distribution-tray stocker bottom plate 46 on which the medicine distribution tray 30 on which packs to be taken in the evening are placed is moved to the tray position E, and the medicine-distribution-tray stocker bottom plate 46 on which packs to be taken bedtime is placed are moved to the tray position F. Note that in the tray position D, the medicine distribution tray 30 on which the packs to be taken in the noontime are placed can be moved to the left in the Y direction and placed on the medicine-distribution-tray stocker bottom plate 46 or the medicine distribution tray 30 can be moved to the right in the Y direction and separated from the medicine-distribution-tray stocker bottom plate 46.

The detailed configuration and operation of the container 10 are described with reference to FIGS. 8A-a, 8A-b, 8B-a, and 8B-b. FIG. 8A-a is a front view of the container 10. FIG. 8A-b is a cross-sectional side view of the container 10. FIG. 8B-a is a cross-sectional front view of the periphery of a partition disposed in the container 10. FIG. 8B-b is a cross-sectional front view illustrating an operation of adjusting the position of the partition in the container 10.

The container 10 mainly includes a case 11 that stores a plurality of packs 2, a lid 14 that allows the packs 2 to be taken in and out, a partition 16 that prevents the packs 2 from falling, a cushion 15 that holds the postures of the packs 2, and a flap portion through which the packs 2 pass when the packs 2 are taken out by the take-out device 50 (see FIG. 1 and the like). The cushion 15 is formed of sponge rubber having appropriate elasticity. Accordingly, the cushion 15 and the partition 16 normally hold the postures of the plurality of packs 2 stored in the case 11 (as illustrated in FIG. 8B-b, the postures of the packs 2 are orderly held in a substantially horizontal state along the Z direction).

The flap portion includes a left flap 12 and a right flap 13. The left flap 12 and the right flap 13 are openable and closable and provided at left and right bottom-wall ends, respectively, of a pack take-out opening 17 opened in a bottom wall of the case 11. The left flap 12 is provided so as to be swingable, openable, and closable about a rotation shaft 12a provided at an end of a left bottom-wall end of the pack take-out opening 17. The right flap 13 is provided so as to be swingable, openable, and closable about a rotation shaft provided at an end of a right bottom-wall end of the pack take-out opening 17.

That is, when a pack 2 is taken out from the container 10 by the take-out device 50 (see FIG. 1), the left flap 12 and the right flap 13 allow the pack 2 to pass through between the left flap 12 and the right flap 13. On the other hand, when the pack 2 is not taken out from the container 10, the left flap 12 and the right flap 13 restrict the passage of the pack 2 to store and hold the plurality of packs 2 in the case 11. Specifically, a torsion coil spring having a biasing force within a predetermined range is mounted between the rotation shaft 12a of the left flap 12 and the left bottom-wall end and between the right flap 13 and the right bottom-wall end. The biasing force of the torsion coil spring is set so that when the pack 2 is taken out from the container 10 by the take-out device 50, the left flap 12 and the right flap 13 allow the passage of the pack 2. When the pack 2 is not taken out from the container 10, the maximum number of packs 2 stored in the case 11 are stored and held.

The lid 14 is formed to be long in the Z direction of the case 11 and to have a predetermined opening width, as illustrated in FIG. 8A-b, such that packs 2 stored in the container 10 can be taken in and out by a staff of a care facility or the like.

As illustrated in FIG. 8A-b, a plurality of packs 2 are stored in the container 10, and the types of the packs 2 are divided for each timing of medication. For example, a type of the packs 2 is allocated for medication in the morning for 14 days taken by a medicine taker A. Therefore, when the medicine taker A takes a medicine in the noontime, the evening, and the bedtime in addition to the morning, a total of four containers 10 are required. The configuration of the container 10 is not limited to the above-described example. For example, a single container 10 may be designated for each medicine taker (person), and packs 2 may be delivered in the take-out direction of the packs 2 upward through the pack take-out opening 17 of the container 10, for example, in the order of: morning, noontime, evening, and bedtime on the first day; morning, noontime, evening, and bedtime on the second day; and so on.

The configuration of the periphery of the partition 16 is described. As illustrated in FIGS. 8A-b, 8B-a, and 8B-b, a long groove 11a having a predetermined width in the Y direction and extending in the Z direction is formed on a side wall of the case 11. At one side end of the partition 16, a shaft 16a with a flange is provided so as to protrude from the long groove 11a. As illustrated in FIGS. 8B-a and 8B-b, a lever 18 is swingably supported on an outer wall of the partition 16 via a rotation fulcrum 18a. A spring 20 is mounted between the inside wall of the partition 16 and the lower end of the lever 18 as illustrated in FIG. 8B-b to apply a biasing force in a direction to constantly rotate the upper end of the lever 18 counterclockwise about the rotation fulcrum 18a. A meshing portion 19 is integrally fixed to the lower end of the lever 18 in FIGS. 8B-a and 8B-b. The meshing portion 19 is integrally formed with a meshing projection that engages with a groove 11b formed with a predetermined width on the side wall of the case 11.

When packs 2 are set in the case 11, the packs 2 are stored in turn upward from the pack take-out opening 17 on the left flap 12 and the right flap 13. Further, as illustrated in FIG. 8B-b, the position of the partition 16 is adjusted so that the stored packs 2 do not fall in the case 11. In the above-described adjustment, the upper end of the lever 18 is pushed so as to swing in the clockwise direction in the FIG. 8B-b around the rotation fulcrum 8B against the biasing force of the spring 20 so as to change from a state in which the lever 18 is substantially vertical as illustrated in FIG. 8B-a to a state illustrated in the FIG. 8B-b. Thus, the engagement between the above-described engagement projection and the groove 11b is released. Owing to this configuration, the position of the partition 16 can be freely adjusted in the Z direction.

The timing at which packs 2 are replenished into the container 10 may be, for example, the timing at which a medicine taker (resident) in a care facility or the like is examined (normally two weeks interval) or the timing at which the packs 2 in the container 10 have run out. When a pack 2 remains in the container 10 at the time of replenishment, the packs 2 are subsequentially replenished from the rear of the remaining pack 2.

The above-described setting of the packs 2 in the container 10, replenishment of the packs 2, or adjustment of the position of the partition 16 are performed by a staff member or the like in a care facility or the like. However, examples and embodiments of the present disclosure are not limited to the above-described example. In some embodiments and examples, for example, a cartridge system may be employed for the container 10 to automate the setting of the packs 2 in the container 10, replenishment of the packs 2, or adjustment of the position of the partition 16.

Figure 9B:
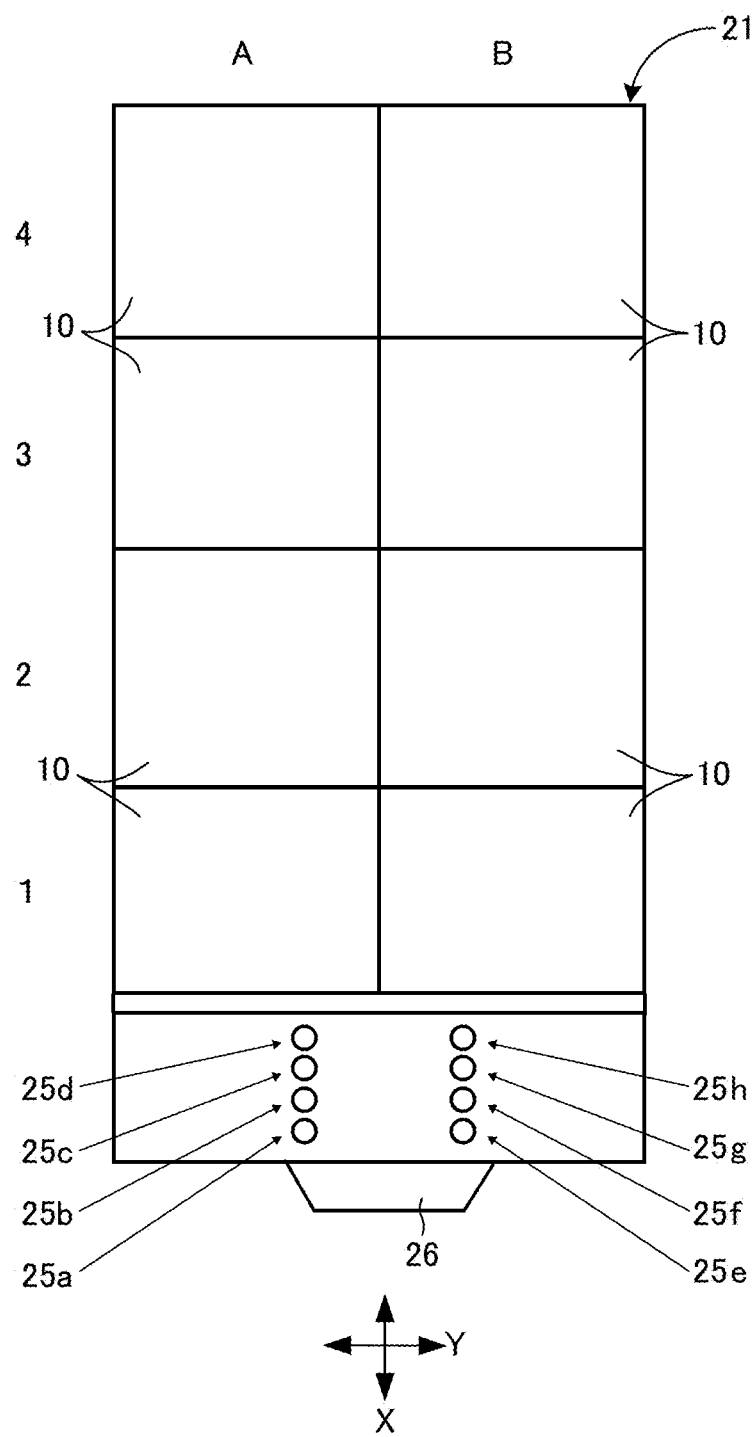
FIG. 9B is a plan view of a drawer of a medication support apparatus illustrating a configuration to identify containers provided in the drawer according to an embodiment of the present disclosure.

With reference to FIGS. 9A and 9B, the attachment and detachment mechanism and operation of the container 10 provided in the drawer 21 are described. FIG. 9A is a cross-sectional plan view of a main part of an attachment and detachment mechanism of the container 10 provided in the drawer 21. FIG. 9B is a schematic plan view illustrating a configuration of identifying the container 10 provided in the drawer 21. As illustrated in FIG. 9A, a plurality of containers 10 is attachable to and detachable from the drawer 21. The container 10 that is attachable and detachable in this manner is generally referred to as a "cartridge". Slide rails 24 are provided on outer left and right wall surfaces of the case 22 of the drawer 21. Each of the slide rails 24 is slidable with a body rail 28 disposed on the body frame 199 (see FIG. 1). Accordingly, the drawer 21 can be pulled out from the inside of the body frame 199 (see FIG. 1) via engagement between the slide rail 24 and the body rail 28 and can be attached to and detached from the body frame 199.

As illustrated in FIG. 9A, the container 10 is attached to and detached from the drawer 21 via engagement and disengagement between a pair of convex portions 23 formed on the inner wall surface of the case 22 of the drawer 21 and a pair of concave portions 11c formed on the outer wall surface of the case 11 of the container 10 and engagement and disengagement between the inner wall surfaces of the case 22 and four hemispherical protrusions 11d formed on the outer wall surfaces of the case 11. Such a configuration of the drawer 21 as described above allows the plurality of containers 10 to be easily attached to and detached from the drawer 21 with good operability. In the above-described example, the containers 10 are attachable to and detachable from the drawer 21 through fitting and engagement of the concave and convex portions. However, embodiments of the present disclosure are not limited to such a configuration and similar effects as described above can be obtained by providing an elastic material in a gap between the inner wall surface of the case 22 and the outer wall surface of the case 11, a configuration using magnetic force as illustrated in FIG. 6, or a snap-fit structure.

As illustrated in 9B, the drawer 21 includes a guide display unit such as LEDs (light emitting diodes) 25a, 25b, 25c, 25d, 25e, 25f, 25g, and 25h in the vicinity of a handle 26 which is held by a hand when the drawer 21 is attached or detached. The guide display unit allows the user to recognize installation positions of the plurality of containers 10. Such a configuration allows to grasp at a glance where the target storage section 10 is located in the drawer 21. In the same FIG. 9B, the LED 25a detects the presence or absence of the container 10 which is attached to or detached from a location A1 of the drawer 21 (which represents a portion or section uniquely determined by vertical columns and horizontal rows in the drawer 21). Similarly, the LED 25b corresponds to a location A2 of the drawer 21, the LED 25c corresponds to a location A3 of the drawer 21, the LED 25d corresponds to a location A4 of the drawer 21, the LED 25e corresponds to a location B1 of the drawer 21, the LED 25f corresponds to a location B2 of the drawer 21, the LED 25g corresponds to a location B3 of the drawer 21, and the LED 25h corresponds to a location B4 of the drawer 21. Note that there is a possibility that a staff or the like as an operator who attaches and detaches the container 10 might make a mistake in reading the guide display unit of the LED 25a, 25b, 25c, 25d, 25e, 25f, 25g, and 25h or the like. In such a case, the presence or absence of the container 10 may be electronically identified by, for example, a sensor or a switch.

Alternatively, a number, a bar code, a QR code, a non-contact IC tag, or the like may be provided on the container 10 to identify the container 10. In such a case, information as to which medicine is stored in which container 10 is stored on the system side. After the drawer 21 to which the containers 10 are attached is set in the body of the medication support apparatus 200, the body side of the medication support apparatus 200 identifies each of the containers 10. Thus, the medication support apparatus 200 can select the target pack 2 without error.

The configuration and operation of the take-out device 50 is described with reference to FIGS. 10A-a and 10A-b, 10B-a to 10B-e, and 10C-a to 10C-e. FIG. 10A-a is a front view of the configuration of the take-out device 50. FIG. 10A-b is a plan view of the take-out device 50 of FIG. 10A-a. FIGS. 10B and 10C are front views of the operation of the take-out device 50. As illustrated in FIGS. 10A-a and 10A-b, the take-out device 50 includes a suction device 51 that takes out a pack 2 from the container 10 and a holder 61 that holds the taken-out pack 2. The suction device 51 includes an air-type suction pump 48 (illustrated in the block diagram of FIG. 13 described later). The suction pump 48 turns the inside of the pack 2 in a negative pressure state to attract the pack 2. The suction pump 48 may be disposed in the take-out device 50 or may be disposed in another portion in the medication support apparatus 200. When the suction pump 48 is disposed in the medication support apparatus 200, the suction device 51 is connected to the suction pump 48 via a communication member such as an air tube.

The suction device 51 includes a pair of suction pads 52 provided in the X direction and communicating with the suction pump 48 to suck the pack 2, a suction duct 53 connected to the suction pads 52, a duct connecter 54 connected to the suction duct 53, and a suction-device vertical mover 55 that moves an integrated body of the suction pads 52, the suction duct 53, and the duct connecter 54 in the Z direction.

The suction-device vertical mover 55 includes a pair of guide rods 56 provided in the X direction to guide the duct connecter 54 in the Z direction, an endless belt 59 wound around a drive pulley 57 and a driven pulley 58, and a suction-device vertical movement motor 60 connected to the drive pulley 57 via a drive transmission member such as a gear or a belt. The duct connecter 54 is connected and fixed to the belt 59 at the belt grip 59a. The guide rod 56 is fixed to a guide rod holder 50a fixed to the take-out frame of the take-out device 50. The suction-device vertical movement motor 60 is fixed to the take-out frame of the take-out device 50. The suction-device vertical movement motor 60 is a control target driver of the suction-device vertical mover 55 (see FIG. 13 described later).

The holder 61 includes a holding tray 62 serving as a receiving base that temporarily holds the taken-out pack 2, guide rod holders 65 connected to both sides of the holding tray 62 in the X direction so that the posture of the holding tray 62 can be changed, a pair of posture change assisting members 47 provided in the X direction to change the posture of the holding tray 62, and a holder vertical mover 63 to move the holding tray 62 in the Z direction. The holding tray 62 has a substantially box shape that temporarily holds the taken-out pack 2, and includes a concave 62a that avoids interference with the above-described integrated body (the suction pad 52, the suction duct 53, and the duct connecter 54) of the suction device 51. A slope 47a is formed in an upper left portion of each of the posture change assisting members 47 in FIG. 10A-a.

The holder vertical mover 63 includes a pair of guide rods 64 provided in the X direction for guiding the holding tray 62 in the Z direction, an endless belt 68 wound around a drive pulley 66 and a driven pulley 67, and a holder vertical movement motor 69 connected to the drive pulley 66 via a drive transmission member such as a gear or a belt. The holder vertical movement motor 69 is a control target driver of the holder vertical mover 63 (see FIG. 13 described later). The guide rod holder 65 is connected and fixed to the belt 68 at the belt grip 68a. The holder vertical movement motor 69 is fixed to the take-out frame of the take-out device 50. Note that the configuration of the suction-device vertical mover 55 or the holder vertical mover 63 is not limited to the above-described vertical reciprocating motion mechanism driven by a belt. For example, a reciprocating linear motion mechanism using a rack and pinion system or the like may be employed for the suction-device vertical mover 55 and the holder vertical mover 63.

The operation of the take-out device 50 is described with reference to FIGS. 10B-a to 10B-e and FIGS. 10C-a to 10C-e. Note that, in the present embodiment, to simplify the descriptions and facilitate understanding, it is assumed that the take-out device 50 is positioned between the container 10 of the drawer 21 disposed at the uppermost portion of the body frame 199 in FIG. 1 and the medicine distribution tray 30 disposed immediately below the container 10 by the operation of the transfer device 90 in FIG. 1. As illustrated in FIG. 10B-a, the take-out device 50 is moved to a position directly below the container 10 by the operation of the transfer device 90 illustrated in FIG. 1 and is in a stop state. At this time, the suction-device vertical movement motor 60 of the suction-device vertical mover 55 is stopped, and the suction pad 52 is positioned below and near the holding tray 62 in the horizontal state. Thereafter, as illustrated in FIG. 10B-b, the suction pad 52 is moved upward by the operation of the suction-device vertical movement motor 60, enters from the pack take-out opening 17 between the left flap 12 and the right flap 13, comes into contact with the pack 2 positioned at the lowermost portion of the container 10, and simultaneously attracts the pack 2. At this time, the suction pump 48 is driven in advance so that the suction operation can be performed.

Next, as illustrated in FIG. 10B-c, the suction pad 52 moves downward while attracting the pack 2 by the suction pad 52 by the reverse operation of the suction-device vertical movement motor 60, and the pack 2 is pulled out from the container 10. Note that the pack take-out opening 17 of the container 10 is formed in a flap shape by the biasing force within a predetermined range of the torsion coil spring as described above. Thus, the pack take-out opening 17 is opened and closed by the drawing operation of the suction pad 52.

Next, as illustrated in FIGS. 10B-d and 10B-e, the taken-out pack 2 is held by the holding tray 62. Thereafter, the suction pad 52 is lowered to a position at which the suction pad 52 does not come into contact with the take-out pack 2, that is, a position (also an initial position of the suction pad 52) in the vicinity of the bottom surface of the holding tray 62 which is in the horizontal state as illustrated in FIG. 10B-a. At this time, the outer bottom surface of the holding tray 62 is in contact with the outer upper surface of the posture change assisting member 47.

Next, as illustrated in FIG. 10C-a, 10C-a', 10C-b, the posture of the holding tray 62 is changed, and an operation of inserting the pack 2 in the holding tray 62 into the medicine distribution tray 30 is performed. After the operation illustrated in FIG. 10C-a, the operation by the suction device 51 is stopped (the suction pad 52 is at the above-described initial position), and only the operation by the holder 61 is performed. Accordingly, components of the suction device 51 are illustrated in solid line and components of the holder 61 are illustrated in broken lines.

Here, an operation illustrated in FIGS. 10C-a, 10C-a', and 10C-b, is described while describing the mechanism for changing the posture of the holding tray 62 holding the pack 2. The holding tray 62 rotates by 90 degrees to change the posture of the pack 2 in the holding tray 62 from a horizontal posture in the horizontal state to the vertical posture in the vertical state. A coupler between the holding tray 62 and the guide rod holder 65 is rotatably connected to the holding tray 62 and the guide rod holder 65. As the belt 68 rotates, the guide rod holder 65 moves downward in the Z direction along the guide rod 64, and the outer bottom surface of the holding tray 62 comes into contact with the slope 47a of the posture change assisting member 47. Thereafter, the outer bottom surface of the holding tray 62 comes into contact with the vertical portion 47b of the posture change assisting member 47. Owing to this mechanism, the posture of the holding tray 62 and the pack 2 held by the holding tray 62 is changed from the horizontal posture to the vertical posture. At this time, a biasing force of a spring in a clockwise direction in FIG. 10C-a acts on the holding tray 62 so that the holding tray 62 and the pack 2 held by the holding tray 62 are always in a horizontal position.

Next, as illustrated in FIGS. 10C-c and 10C-d, the holding tray 62 in the vertical state holding the pack 2 moves downward in the Z direction along the guide rod 64 via the guide rod holder 65 as the belt 68 further rotates. When the holding tray 62 in the vertical state comes into contact with the upper end of the medicine distribution tray 30, a bottom portion 62b of the holding tray 62 is opened in conjunction with the downward movement of the holding tray 62 in the Z direction, and the pack 2 in the holding tray 62 is transferred into the medicine distribution tray 30. As described above, the opening and closing of the bottom portion 62b of the holding tray 62 in the vertical state is performed in conjunction with the downward movement of the holding tray 62 in the Z direction. This operation is performed by, for example, a mechanism in which a convex portion is provided on the take-out device 50 and the holding tray 62 in the vertical state comes into contact with the bottom portion 62b and opens when the holding tray 62 reaches a certain position. The position of the convex portion provided on the take-out device 50 is not limited to the inside of the take-out device 50. For example, a part of the convex portion may be provided in the medicine distribution tray 30, or an intermediate member provided between the drawer 21 (see FIG. 1, 9B, and the like) and the medicine distribution tray 30 may have the function of the convex portion.

Next, as illustrated in FIG. 10C-e, the holding tray 62 in an empty state after the packs 2 in the holding tray 62 are transferred to the medicine distribution tray 30 moves upward in the Z direction along the guide rod 64 via the guide rod holder 65 as the belt 68 rotates in reverse.

As described above, one feature of the take-out device 50 is that the pack 2 stored in the container 10 is taken out from the lower side of the container 10. With such a configuration, the next pack 2 remaining in the container 10 moves by its own weight to the pack take-out opening 17 (see FIG. 8A) located at the lower portion of the container 10. Thus, the take-out device 50 can take out the pack 2 by the same operation regardless of the remaining amount of the pack 2 remaining in the container 10.

Figure 11A:
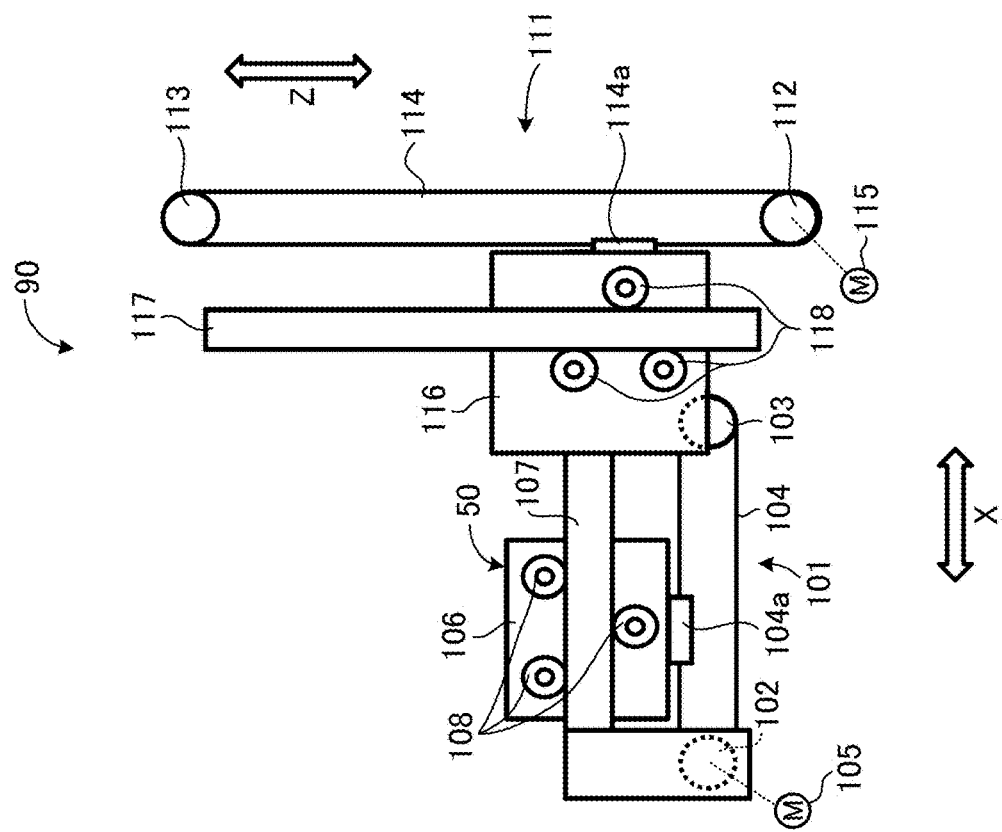
FIG. 11A is a front view of a main part of a transfer device according to an embodiment of the present disclosure.
Figure 11B:
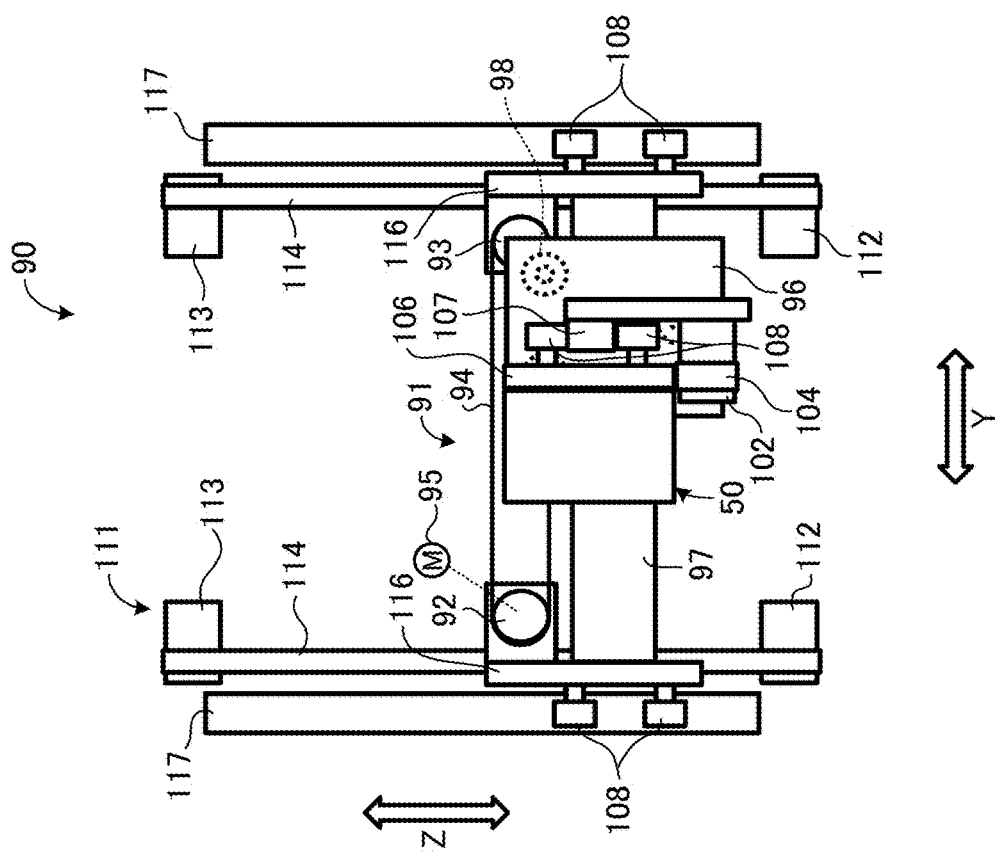
FIG. 11B is a side view of the main part of the transfer device of FIG. 11A.

The configuration and operation of the transfer device 90 are described with reference to FIGS. 11A and 11B. FIG. 11A is a front view of the configuration of a main part of the transfer device 90. FIG. 11B is a side view of the transfer device 90 illustrated in FIG. 11A. As in the configuration of the medication support apparatus 200 of FIGS. 1A and 1B, the containers 10 are placed on the planes of the upper and lower portions of the medication support apparatus 200 in the Z direction with the medicine distribution tray 30 interposed between the upper and lower portions. The medicine distribution tray 30 is located above the lowermost container 10, so that the take-out device 50 moves in three directions: front-back or depth direction (X direction), left-right or lateral direction (Y direction), and up-down or vertical direction (Z direction). In this manner, the transfer device 90 moves the pack 2 in the X direction, the Y direction, and the Z direction to transfer the pack 2 taken out from the container 10 by the take-out device 50 and to deliver the pack 2 to the medicine distribution tray 30.

The take-out device 50 is moved in the Y direction by a Y-direction transfer device 91, in the X direction by a X-direction transfer device 101, and in the Z direction by a Z-direction transfer device 111. The Y-direction transfer device 91, the X-direction transfer device 101, and the Z-direction transfer device 111 have similar configurations.

The Y-direction transfer device 91 includes a Y adapter 96 attached to the take-out device 50, a Y guide 97 to guide the take-out device 50 in the Y direction via the Y adapter 96, an endless belt 94 wound between a driving pulley 92 and a driven pulley 93, and a Y-direction transfer motor 95 connected to the driving pulley 92 via a driving force transmission member such as a gear or a belt. Three rollers 98 are rotatably attached to the Y adapter 96 in a state in which the Y guide 97 is sandwiched by the three rollers 98. The Y adapter 96 is connected and fixed to the endless belt 94 via a belt grip.

With the above-described configuration of the Y-direction transfer device 91, when the Y-direction transfer motor 95 is driven, the driving force is transmitted to the endless belt 94 via the driving force transmitting member and the driving pulley 92, the endless belt 94 rotates and the take-out device 50 moves in the Y direction along the Y guide 97 together with the Y adapter 96.

The X-direction transfer device 101 includes an X adapter 106 attached to the take-out device 50, an X guide 107 to guide the take-out device 50 in the X direction via the X adapter 106, an endless belt 104 wound between a driving pulley 102 and a driven pulley 103, and an X-direction transfer motor 105 connected to the driving pulley 102 via a driving force transmission member such as a gear or a belt. Three rollers 108 are rotatably attached to the X adapter 106 in a state in which the X guide 107 is sandwiched by the three rollers 108. The X adapter 106 is coupled and fixed to the endless belt 104 via a belt grip 104a.

With the above-described configuration of the X-direction transfer device 101, when the X-direction transfer motor 105 is driven, the driving force is transmitted to the endless belt 104 via the driving force transmitting member and the driving pulley 102, the endless belt 104 rotates and the take-out device 50 moves in the X direction along the X guide 107 together with the X adapter 106.

The Z-direction transfer device 111 includes a pair of Z adapters 116 attached to both ends of the Y guide 97 in the Y-direction, a pair of Z guides 117 to guide the take-out device 50 in the Z-direction via the Y guide 97 and the pair of Z adapters 116, a pair of endless belts 114 wound between the driving pulley 112 and the driven pulley 113, and a Z-direction transfer motor 115 connected to the driving pulley 112 via a driving force transmission member such as a gear or a belt. In the Z-direction transfer device 111, the driving pulleys 112, the driven pulleys 113, and the endless belts 114 are provided on both sides of the Z-direction transfer device 111 in the X-direction. However, the Z-direction transfer motor 115 is provided only on one of the driving pulleys 112. Three rollers 118 are rotatably attached to each of the Z adapters 116 in a state in which each of the Z guides 117 is sandwiched by the three rollers 118. Each of the Z adapters 116 is connected and fixed to corresponding one of the endless belts 114 via corresponding one of the belt grips 114a.

With the above-described configuration of the Z-direction transfer device 111, when the Z-direction transfer motor 115 is driven, the driving force is transmitted to the endless belt 114 via the driving force transmitting member and the driving pulley 112. Thus, the endless belt 114 rotates and the take-out device 50 moves in the Z direction along the Z guide 117 together with the Y guide 97 and the Z adapter 116.

In FIGS. 11A and 11B, the take-out device 50 moves in three axial directions of the X-axis, the Y-axis, and the Z-axis. However, for example, in a configuration in which the container 10 is disposed in an upper portion of the transfer device 90 and the medicine distribution tray 30 is disposed in a lower portion of the transfer device 90 with the take-out device 50 interposed between the container 10 and the medicine distribution tray 30, the take-out device 50 may move only in the front-rear or depth direction (the X-direction) and in the left-right or lateral direction (the Y-direction). Thus, the number of directions in which the take-out device 50 moves can be reduced from three to two.

Figure 12:
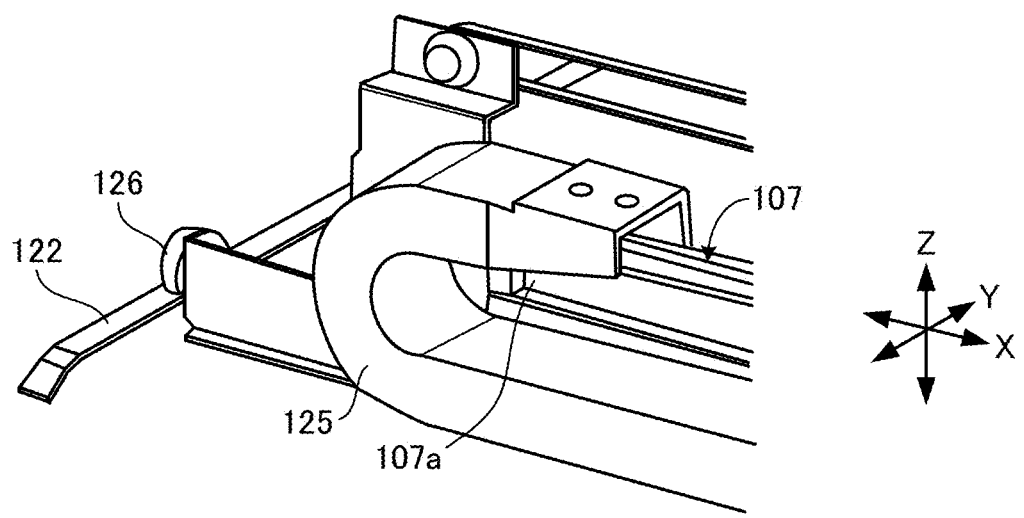
FIG. 12 is a perspective view of a configuration example in which a transfer device holds an end of a Y guide in a transfer device according to an embodiment of the present disclosure.

In the configuration of the transfer device 90 of FIGS. 11A and 11B, a tip end of the X guide 107 in the X direction is not held. Therefore, as illustrated in FIG. 12, a roller 126 may be provided at a tip end of a bracket 125 to hold the tip end 107a of the X guide 107. The tip end 107a of the X guide 107 is attached to and supported by the bracket 125. In addition, the roller 126 may be rotatably disposed on a receiver 122 provided on the body frame 199 side. With the above-described configuration, the tip end 107a of the X guide 107 can be prevented from being bent by its own weight. This reduces variations in the distance between the take-out device 50 and the container 10 or the distance between the take-out device 50 and the medicine distribution tray 30. Thus, the packs 2 can be stably taken out from or inserted into the medicine distribution tray 30.

Figure 13:
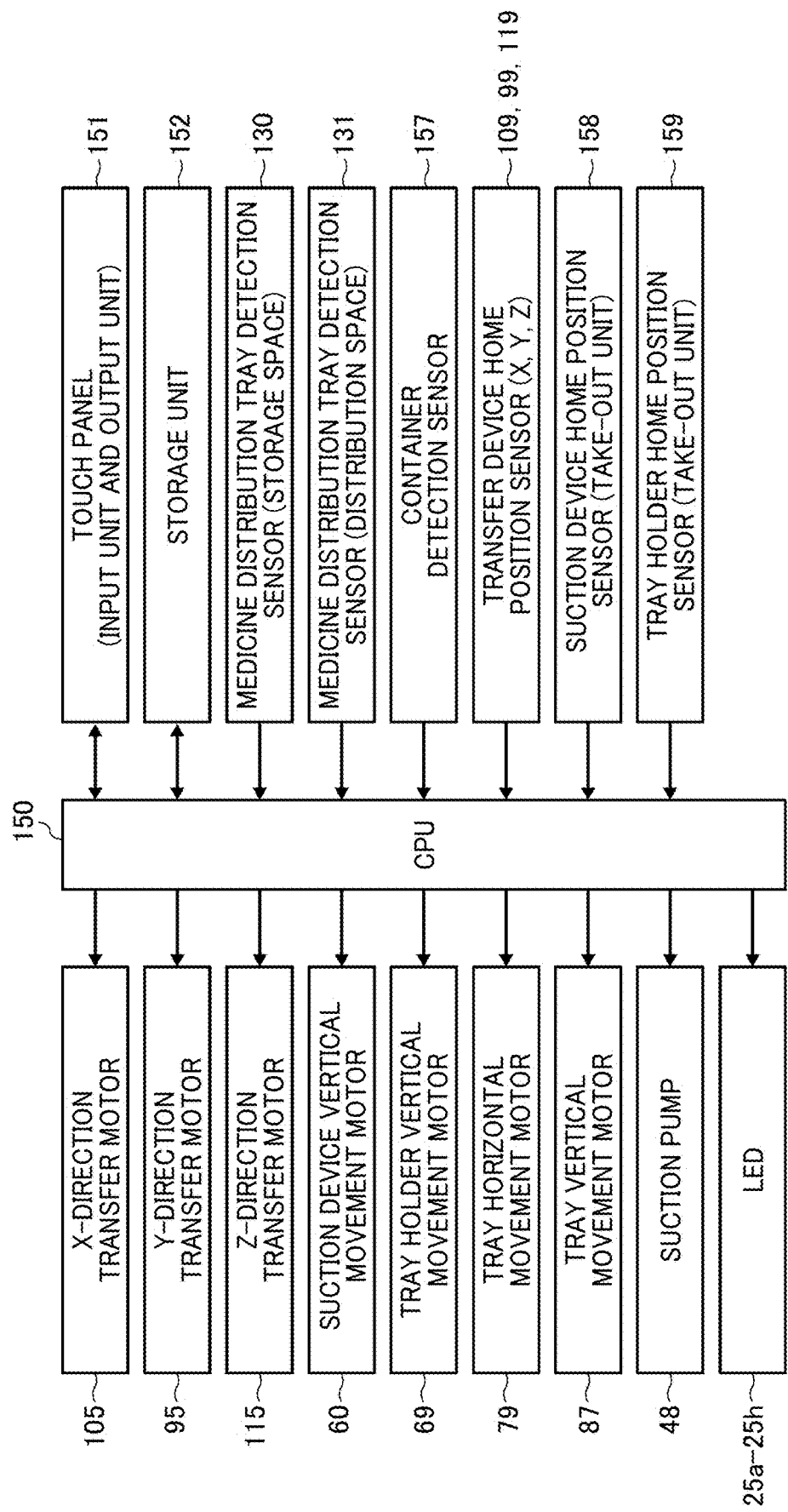
FIG. 13 is a control block diagram of a main control configuration of the medication support apparatus of FIG. 1 according to an embodiment of the present disclosure.

With reference to FIG. 13, a control configuration of the medication support apparatus 200 according to an embodiment of the present disclosure is described. As illustrated in FIG. 13, the medication support apparatus 200 includes a CPU (central processing unit) 150 that functions as a controller that performs operation control of each unit and the like of the medication support apparatus 200. The CPU 150 includes a storage unit, a timer unit, and the like. The CPU 150 issues a notification to a staff or the like and an instruction for an operation of the medication support apparatus 200 at a timing according to a program based on various inputs described later.

The CPU 150 may include a timer (time measuring) function in addition to the calculation and control functions. Examples of the storage unit 152 include a read-only memory (ROM), a random access memory (RAM), an external memory, and the like. In the ROM, a program (for example, a program such as a control flowchart described later) readable by the CPU 150, various data, and the like are stored in advance. Examples of the data include data on the relationship between the compartment 33 of the medicine distribution tray 30 and the pack 2 allocated to each individual medicine taker, data on the relationship between the compartment 33 of the medicine distribution tray 30 and the pack 2 allocated to each medication timing, and data on the relationship between the compartment 33 of the medicine distribution tray 30 and the pack 2 allocated based on each medication order.

A touch panel 151 as a user interface is electrically connected to an input and output port of the CPU 150. The touch panel 151 is not limited to the above configuration. For example, an input unit and a display unit may be separated from each other and a keyboard and an LED display unit may be combined.

The input port of the CPU 150 is electrically connected to a medicine-distribution-tray detection sensor 130 that detects the type of the medicine distribution tray 30 stored in the medicine distribution tray stocker 45, a medicine-distribution-tray detection sensor 131 that detects whether the medicine distribution tray 30 is positioned in the medicine distribution unit 29, and a container detection sensor 157 that detects the presence or absence of the pack 2 in the container 10. The input port of the CPU 150 is also electrically connected to a transfer device HP sensor 99 to detect a home position (hereinafter abbreviated as "HP") of the Y-direction transfer device 91 in the take-out device 50, a transfer device HP sensor 109 to detect a HP of the X-direction transfer device 101 in the take-out device 50, and a transfer device HP sensor 119 to detect a HP of the Z-direction transfer device 111 in the take-out device 50. The input port of the CPU 150 is also electrically connected to a suction device HP sensor 158 that detects a HP of the suction device 51 (particularly, the suction pad 52) in the take-out device 50, and a holder HP sensor 159 that detects a HP of the holder 61 (particularly, the holding tray 62) in the take-out device 50.

The output port of the CPU is electrically connected to the LEDs 25a, 25b, 25c, 25d, 25e, 25f, 25g, and 25h of the drawer 21, the suction pumps 48, the lateral movement motor 79 of the medicine-distribution-tray lateral mover 70, the vertical movement motor 87 of the medicine-distribution-tray vertical mover 82, the suction-device vertical movement motor 60, the holder vertical movement motor 69, the Y-direction transfer motor 95 of the Y-direction transfer device 91, the X-direction transfer motor 105 of the X-direction transfer device 101, and the Z-direction transfer motor 115 of the Z-direction transfer device 111. A notification unit may be electrically connected to the output port of the CPU 150. The notification unit notifies the state of the medication support apparatus 200 and each of the above-described units by light of an LED or the like, sound including voice, or vibration. A speaker, lights, and the like are provided to inform the timing of medication and the like even if the staff and the like are away from the medication support apparatus 200.

When input information from the touch panel 151 and various signals from various sensors are input to the CPU 150, the CPU 150 outputs the following command signals. That is, the CPU 150 outputs command signals for controlling an audio device and an optical device of a display device (including the notification unit) of the touch panel 151, the LEDs 25a, 25b, 25c, 25d, 25e, 25f, 25g, and 25h, the suction pumps 48, the lateral movement motor 79, the vertical movement motor 87, the suction-device vertical movement motor 60, the holder vertical movement motor 69, the Y-direction transfer motor 95, the X-direction transfer motor 105, and the Z-direction transfer motor 115. The CPU 150 has a function of executing a control operation illustrated in a control flowchart described later.

Figure 14:
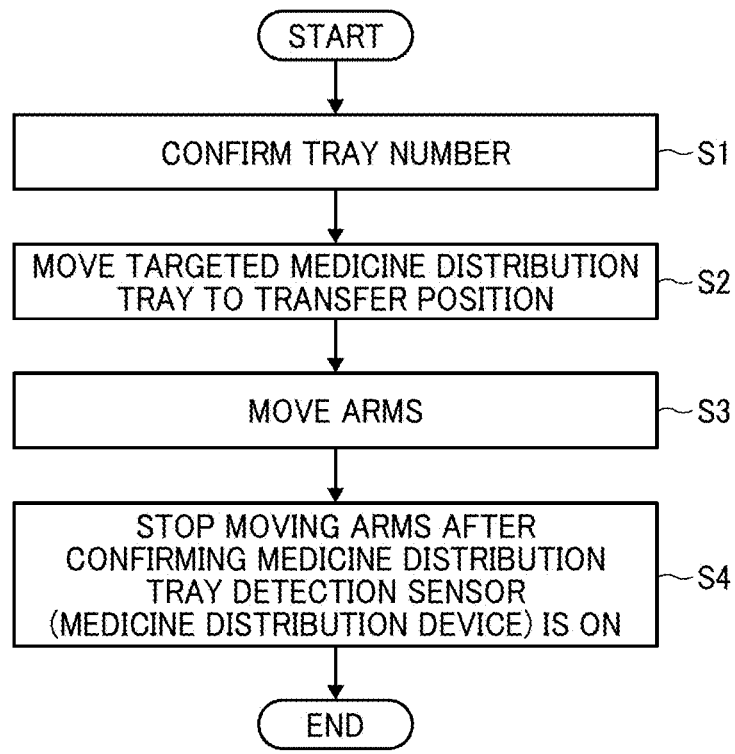
FIG. 14 is a flowchart illustrating an operation flow in which a target medicine distribution tray is taken out from the medicine distribution tray stocker according to an embodiment of the present disclosure.

With reference to the flowchart illustrated in FIG. 14, an operation flow (see FIG. 7B) of taking out the target medicine distribution tray 30 from the medicine distribution tray stocker 45 is described. First, in step S1, the number of the medicine distribution tray 30 to be taken out from the medicine distribution tray stocker 45 is confirmed. Next, the target medicine distribution tray 30 is moved to a predetermined movement position on the bottom plate 39 of the medicine distribution unit 29. At this time, the lateral movement motor 79 is driven to move the target medicine distribution tray 30 sandwiched between the pair of arms 71a and 71b (step S2 and step S3). Next, when the medicine-distribution-tray detection sensor 131 of the medicine distribution unit 29 is turned on and it is confirmed that the target medicine distribution tray 30 occupies the movement position, the driving of the lateral movement motor 79 is stopped. Accordingly, the movement of the pair of arms 71a and 71b stops (step S4).

Figure 15:
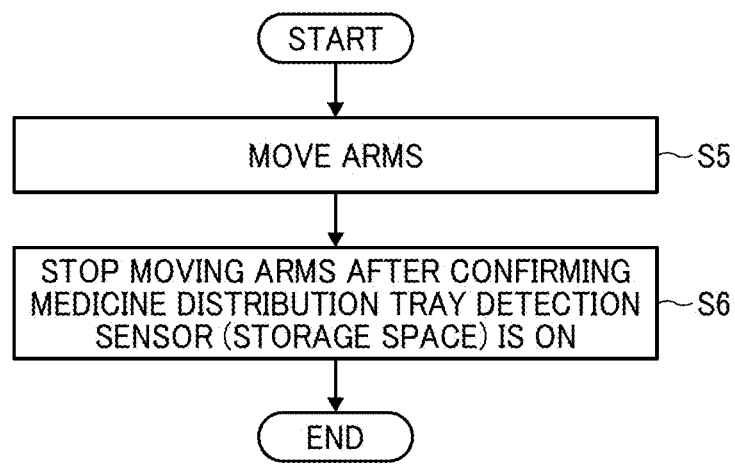
FIG. 15 is a flowchart illustrating an operation flow in which a medicine distribution tray located in a medicine distribution space is returned to the medicine distribution tray stocker according to an embodiment of the present disclosure.

With reference to the flowchart illustrated in FIG. 15, the operation flow (see FIG. 7A) of returning the medicine distribution tray 30 located in the medicine distribution unit 29 to the medicine distribution tray stocker 45 is described. The lateral movement motor 79 is driven so as to move the medicine distribution tray 30 positioned in the medicine distribution unit 29 sandwiched between the pair of arms 71a and 71b to the medicine distribution tray stocker 45 (in step S5, described as arm movement). Next, when the medicine-distribution-tray detection sensor 130 of the medicine distribution tray stocker 45 is turned on and it is confirmed that the target medicine distribution tray 30 has moved onto the medicine-distribution-tray stocker bottom plate 46 of the medicine distribution tray stocker 45, the driving of the lateral movement motor 79 is stopped. Accordingly, the movement of the pair of arms 71a and 71b stops (step S6).

The main overall operation of the medication support apparatus 200 is described with reference to FIGS. 16A1, 16A2, 16A3, 16B, and 16C. This operation is executed under the control command of the CPU 150 as the controller. As illustrated in FIGS. 16A1, 16A2, and 16A3, the operation of taking out the pack 2 from the lower side of the container 10 by the take-out device 50 is performed. The detailed operation has been described with reference to FIGS. 10B-a, 10B-b, 10B-c, 10B-d, and 10B-e. After the pack 2 taken out from the container 10 is received by the holding tray 62, the pack 2 is held in the holding tray 62 of the take-out device 50 in the posture illustrated in FIG. 16B by the posture change operation of the holding tray 62 similar to the posture change operation described with reference to FIGS. 10C-a and 10C-b. Then, as illustrated in FIG. 16B, the take-out device 50 holding the pack 2 in the holding tray 62 is transferred by the transfer device 90 to the medicine distribution unit 29 in which the medicine distribution tray 30 is installed. When the take-out device 50 is conveyed to a position substantially directly above the medicine distribution tray 30 of the medicine distribution unit 29, the pack 2 is inserted into a predetermined compartment 33 which is a predetermined position on the medicine distribution tray 30 by the operation described in FIGS. 10C-c, 10C-d, and 10C-e.

After the above operation is performed a plurality of times and the necessary packs 2 are inserted into the predetermined compartments 33 of the medicine distribution tray 30, as illustrated in FIG. 16C, the medicine distribution tray 30 is taken out to the outside of the medication support apparatus 200 from, for example, the second port 42, and is received by a staff member or the like of a care facility or a medication supporter.

Figure 17:
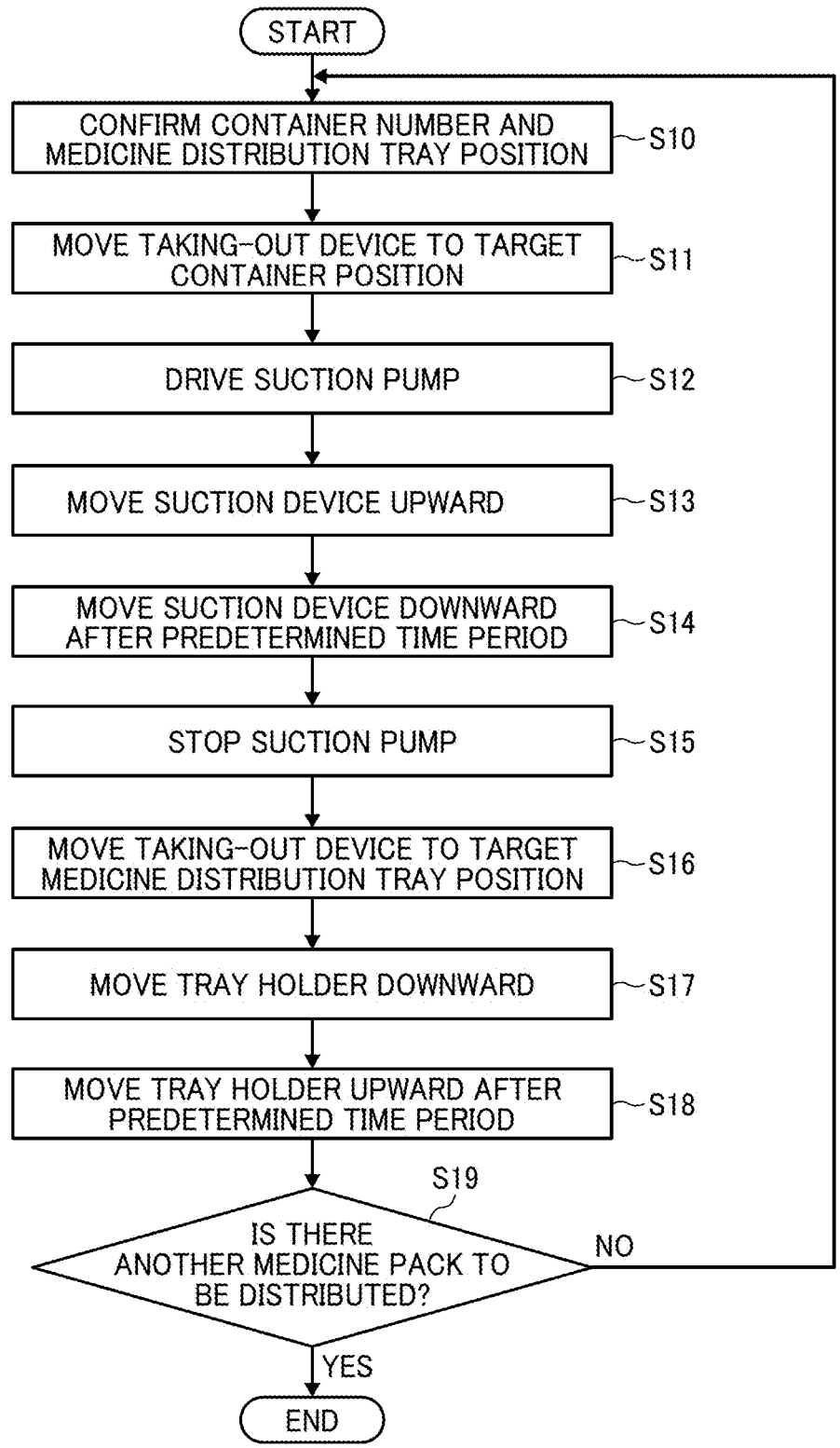
FIG. 17 is a flowchart illustrating an operation flow of a take-out device according to an embodiment of the present disclosure.

The operation flow of the take-out device 50 illustrated in FIGS. 16A1, 16A2, 16A3, 16B, and 16C is supplemented with reference to FIG. 17. FIG. 17 is a flowchart of an operation flow of the take-out device 50. In step S10 of FIG. 17, the number of the container 10 in which the pack 2 to be distributed is confirmed, and the position of the medicine distribution tray 30 into which the pack 2 is inserted and delivered is confirmed. Next, the take-out device 50 is moved to the target container 10 by the transfer operation of the transfer device 90 (step S11). Next, the suction-device vertical movement motor 60 while driving the suction pumps 48 to move the suction device 51 upward (step S12 and step S13). After a certain period of time in which the lowermost pack 2 in the container 10 is sucked and held by the suction pad 52, the suction-device vertical movement motor 60 is driven in reverse to move the suction device 51 downward. Thereafter, the suction pumps 48 are stopped (step S14 and step S15).

Next, the take-out device 50 is moved to the position of the target medicine distribution tray 30 by the transfer operation of the transfer device 90. When the take-out device 50 has moved to the position of the target medicine distribution tray 30, the holder vertical movement motor 69 is driven to move the holder 61 downward (step S16 to step S17). After a certain period of time required for the holder 61 to be moved downward and the pack 2 in the holding tray 62 to be inserted into and delivered to the predetermined compartment 33 of the medicine distribution tray 30, the holder vertical movement motor 69 is driven in reverse to move the holder 61 upward (step S18). Then, it is checked whether there is any other pack 2 to be distributed, and when there is no other pack 2 to be distributed, the series of operation flows is ended (step S19). On the other hand, when there is another pack 2 to be distributed in the step S19, the process returns to the step S10, and the same operation as described above is repeated.

A selection display screen (hereinafter simply referred to as "screen") of the touch panel 151 is described with reference to FIGS. 18 to 26. The information of the resident (medicine taker) includes a name, a room number, a pack type (a medicine type), a medication timing (morning, afternoon, evening, bedtime, etc.), an additional medicine, and a deleted medicine, and these pieces of information are registered in advance in the medication support apparatus 200 or the control system. FIGS. 18 to 26 illustrate screen contents of the touch panel 151 for this purpose.

Figure 18:
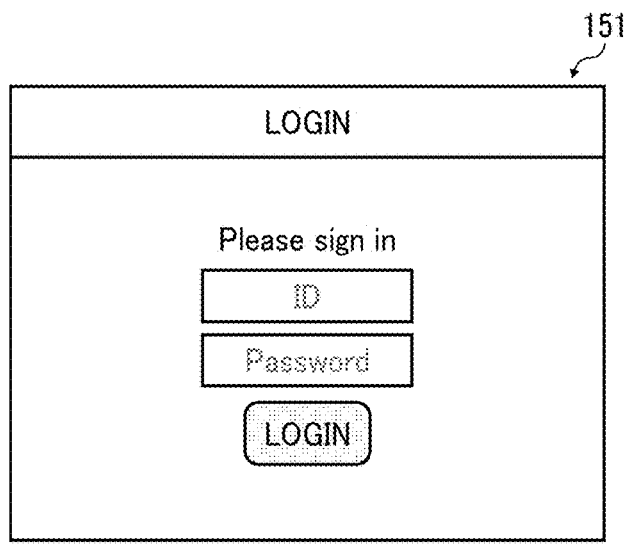
FIG. 18 is a diagram illustrating an initial screen displayed on a touch panel of a medication support apparatus according to an embodiment of the present disclosure.
Figure 19:
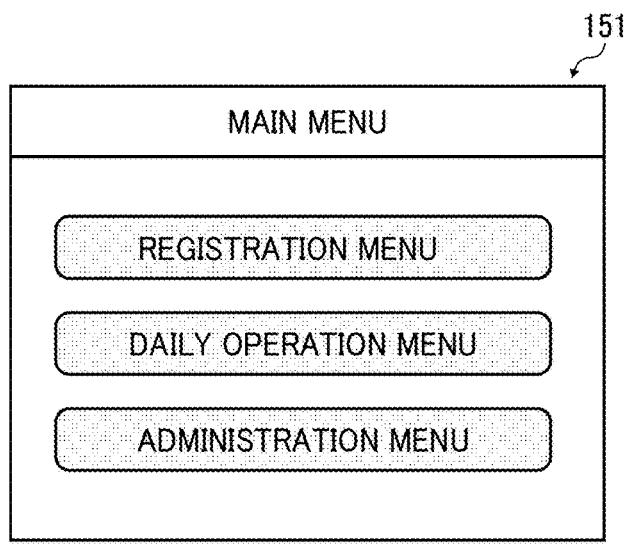
FIG. 19 is a diagram illustrating a "main menu" screen displayed on a touch panel of a medication support apparatus according to an embodiment of the present disclosure.

FIG. 18 illustrates an initial screen displayed on the touch panel 151 after the medication support apparatus 200 is powered on. When the "LOGIN" button displayed in gray is touched on the initial screen displayed on the touch panel 151 in FIG. 18, the screen shifts to the "MAIN MENU" screen illustrated in FIG. 19. When the "REGISTRATION MENU" button is touched on the "MAIN MENU" screen illustrated in FIG. 19, the screen shifts to the "REGISTRATION MENU" screen illustrated in FIG. 20. The "REGISTRATION MENU" screen includes buttons of "NEW REGISTRATION", "CHANGE OR DELETE", and "CONFIRMATION OF REGISTRATION INFORMATION". Using the "CHANGE OR DELETE" and "CONFIRMATION OF REGISTRATION INFORMATION" buttons allows to appropriately change or delete registered information and confirm registered information, which is described later.

Figure 20:
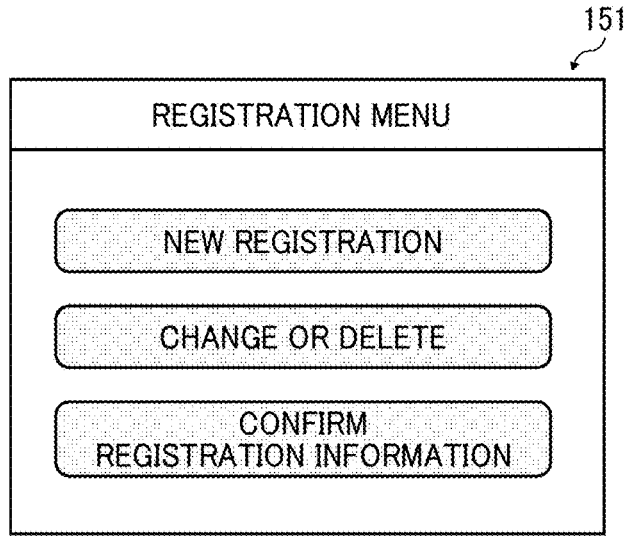
FIG. 20 is a diagram illustrating a "registration operation menu" screen displayed on a touch panel of a medication support apparatus according to an embodiment of the present disclosure.

When the "NEW REGISTRATION" button in FIG. 20 is selected, the screen shifts to the "BASIC INFORMATION" screen in FIG. 21, and detailed information such as name, room number, age, and the like as basic information of the resident can be registered. In addition, on the "MEDICATION INFORMATION" screen of FIG. 22, the detailed content of the pack (medicine) in which types of medicines to be taken by the resident are packaged as one-dose package can be registered. Specifically, the name of the resident (e.g., a medicine taker A) and the pack number (e.g., 1) and the content of the pack (two tablets of drug A and one capsule of drug B are packaged as one-dose package to be taken by the medicine taker A) can be registered. (The same applies hereinafter).

On the "MEDICATION INFORMATION (CONTAINER)" screen of FIG. 23, as the container 10 storing the pack No. 1 to be taken in the morning at the medication timing of the medicine taker A registered in FIG. 22, the No. 1 of the drawer 21 placed in the lower part of FIG. 1 or No. 2 of the drawer 21 placed in the upper portion of FIG. 1 can be selected.

As in the "MEDICATION INFORMATION (MEDICINE DISTRIBUTION TRAY)" screen illustrated in FIG. 24, predetermined compartments of the medicine distribution tray 30 in which packs are placed and medicine distribution position information are also registered in advance in the resident information. As in the "MEDICATION INFORMATION" screen illustrated in FIG. 25, the containers are also provided with numbers, bar codes and QR codes, non-contact IC tags, and the like so that the individual containers can be recognized, and when the packs are placed in the containers, the container numbers and the resident information (who and what medicine at what medication timing) are associated with each other.

On the "MEDICATION INFORMATION" screen illustrated in FIG. 25, the medication information of the pack is registered. As the pack No. 1 to be taken by the medicine taker A, "DRAWER NO. 1", "COLUMN NO. A", "ROW NO. 1" are set as the position information of the pack No. 1 in the container 10. In addition, a predetermined compartment provided at the position of "TRAY NO. A (MORNING)", "COLUMN NO. A" and "ROW NO. 1" in the medicine distribution tray 30 is set. Then, on the "MEDICATION INFORMATION" screen illustrated in FIG. 26, "REGISTRATION OK" indicates that the above-described registration content has been registered.

Touching the "RETURN" button as needed allows the screen to return to the "REGISTRATION MENU" screen of FIG. 20. Then, touching the "CONFIRMATION OF REGISTRATION INFORMATION" button in FIG. 20, a table of medication timing can be created based on the above-described setting information on the "CONFIRMATION OF REGISTRATION INFORMATION (CONTAINER AND TRAY)" screen illustrated in FIG. 27 and the "CONFIRMATION OF REGISTRATION INFORMATION (MEDICATION TIMING)" screen illustrated in FIG. 28.

Owing to the setting as described above, for example, when the morning medicine distribution tray is created, it can be recognized as follows. The packs are transferred from the container No. 1-A-1 containing the morning packs of the medicine taker A to the medicine distribution tray No. A (morning)-A-1 and from the container No. 1-B-1 containing the morning packs of the medicine taker B to the medicine distribution tray No. A (morning)-A-2. Repeating these operations allows to complete the medicine distribution tray 30 for morning illustrated in FIG. 2B.

The completed medicine distribution tray 30 is temporarily returned to the medicine distribution tray stocker 45 and can be stored until the staff or the like takes out the medicine distribution tray 30. In this case, preparation of the medicine distribution tray 30 for the next medication for lunch may be started. In this way, creating the medicine distribution tray 30 in advance allows to smoothly perform assistance in taking medication to the residents and to check in advance whether the medicine is suitable for the conditions of the residents at a specific time.

Figure 30:
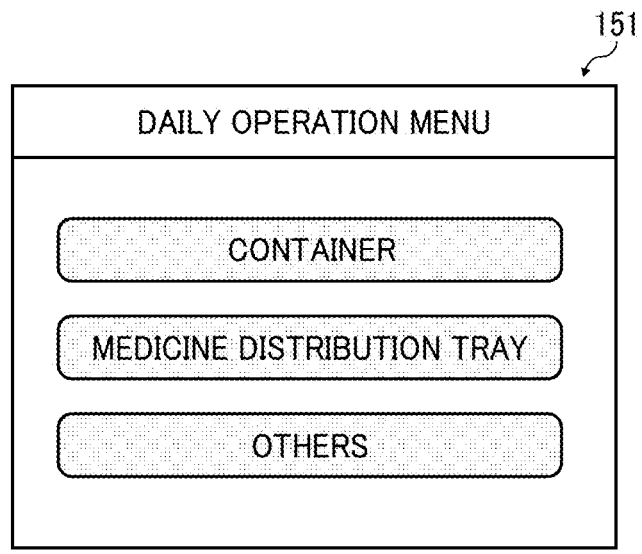
FIG. 30 is a diagram illustrating a "daily work menu" screen displayed on a touch panel of a medication support apparatus according to an embodiment of the present disclosure.
Figure 31:
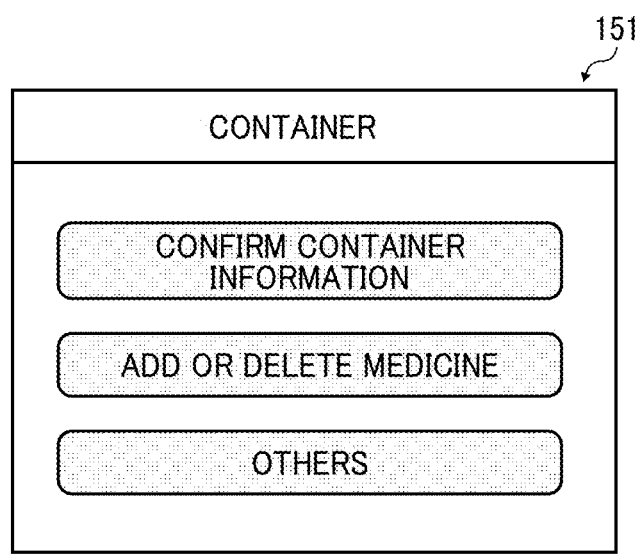
FIG. 31 is a diagram illustrating a "container" screen displayed on a touch panel of a medication support apparatus according to an embodiment of the present disclosure.

The "CHANGE OR DELETE" screen illustrated in FIG. 29 allows to change or delete the "CONFIRMATION OF REGISTRATION INFORMATION (MEDICATION TIMING)" illustrated in FIG. 28. The "DAILY OPERATION MENU" screen illustrated in FIG. 30 allows to perform daily operation related to "CONTAINER", "MEDICINE DISTRIBUTION TRAY", and "OTHERS". The "CONTAINER" screen illustrated in FIG. 31 corresponds to the "CONTAINER" screen illustrated in FIG. 30, and is used to perform the operations of "CONFIRMATION OF CONTAINER INFORMATION", "ADD OR DELETE MEDICINE", and "OTHERS". The "CONFIRMATION OF CONTAINER INFORMATION" screen illustrated in FIG. 32 allows to perform the operation corresponding to the "CONFIRMATION OF CONTAINER INFORMATION" of FIG. 31.

The "ADD OR DELETE" screen illustrated in FIG. 33 allows to add or delete information registered in the "CHANGE OR DELETE" screen illustrated in FIG. 29. The "ADD OR DELETE MEDICINE" screen illustrated in FIG. 34 allows to add or delete information registered in the "MEDICATION INFORMATION" screen illustrated in FIG. 25.

Figure 35:
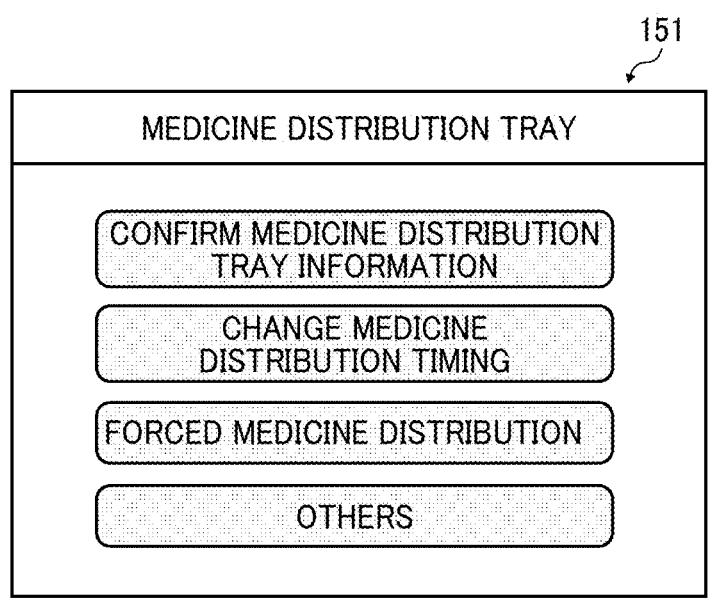
FIG. 35 is a diagram illustrating a "medicine distribution tray" screen displayed on a touch panel of a medication support apparatus according to an embodiment of the present disclosure.

The "MEDICINE DISTRIBUTION TRAY" screen illustrated in FIG. 35 allows to perform the operations related to "CONFIRMATION OF MEDICINE DISTRIBUTION TRAY INFORMATION", "CHANGE OF MEDICINE DISTRIBUTION TIME", "FORCED MEDICINE DISTRIBUTION", and "OTHERS". FIG. 36 illustrates an example of "CONFIRMATION OF MEDICINE DISTRIBUTION TRAY INFORMATION" in FIG. 35. FIGS. 37 and 38 illustrate examples of "CHANGE OF MEDICINE DISTRIBUTION TIMING" in FIG. 35.

The timing at which the medicine distribution tray is created may be a timing at which a staff member or the like issues an execution command to the medication support apparatus 200 or the control system, and the medicine distribution operation (moving the pack from the target container to a predetermined position of the medicine distribution tray) may be performed (see FIGS. 40 to 47 described later). However, in such a case, there is a possibility that workload of the staff of the care facility or the like is increased, or the medicine distribution tray is not prepared when an execution instruction is forgotten. Thus, the medicine might not be immediately taken when the medication is necessary. Therefore, as in the screen illustrated in FIG. 37, the "MEDICINE DISTRIBUTION COMPLETION TIME" when the medicine distribution of the pack to the medicine distribution tray is completed can be registered in the medicine distribution support device or the control system.

As a result, the number of packs required at each medication timing and the time taken to convey the packs from the container to the medicine distribution tray can be grasped in advance from each resident information, and the medicine distribution tray completion time can be grasped. Therefore, starting the operation of the medication support apparatus 200 when the above-described time is traced back allows to prepare the medicine distribution tray at the set medicine distribution completion time. At this time, the above-described configuration is not limited to setting the medication support apparatus 200 to start operating when the above-described time is traced back. For example, the staff or the like may register the "medicine distribution start time" and display the "medicine distribution completion time". Conversely, when the "medicine distribution completion time" is set, the operation start time of the medication support apparatus 200 may be displayed. Such a configuration as described above allows to cope with a sudden change in medicine information.

When there is no target tray to be distributed, the user (staff or the like) is notified, and the medicine distribution operation is not performed. In this case, the medicine distribution tray is not completed, and the residents cannot take medicine. Therefore, as illustrated in FIG. 38, the time for taking in and out the medicine distribution tray is set. Such an arrangement allows for stable operation without stopping the medicine distribution operation of the medication support apparatus 200. Such an arrangement is also helpful to forget to remove the medicine distribution tray.

With reference to FIGS. 39A and 39B, a medication support apparatus 200A as a variation of the medication support apparatus 200 in FIG. 1 is described. FIG. 39A is a schematic front view of a main configuration of the entire medication support apparatus 200A according to a variation. FIG. 39B is a schematic side view of the configuration of the entire medication support apparatus 200 illustrated in FIG. 39A. As illustrated in FIGS. 39A and 39B, the medication support apparatus 200A according to the variation is different from the medication support apparatus 200 of FIG. 1 as follows. In the medication support apparatus 200A, a pack tray 120 as a forced medicine distribution device or a forced medicine distribution table is provided in the vicinity of the medicine distribution tray 30, and a take-out port 121 through which the pack tray 120 can be taken out to the inside and outside of the body frame 199 is attached.

Figure 40:
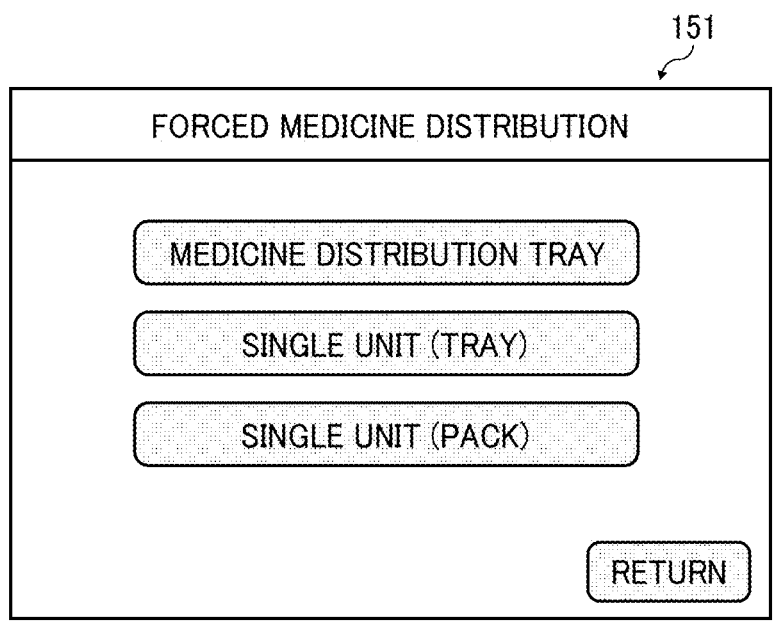
FIG. 40 is a diagram illustrating a screen of "Forced Medicine Distribution" displayed on a touch panel of a medication support apparatus according to an embodiment of the present disclosure.
Figure 42:
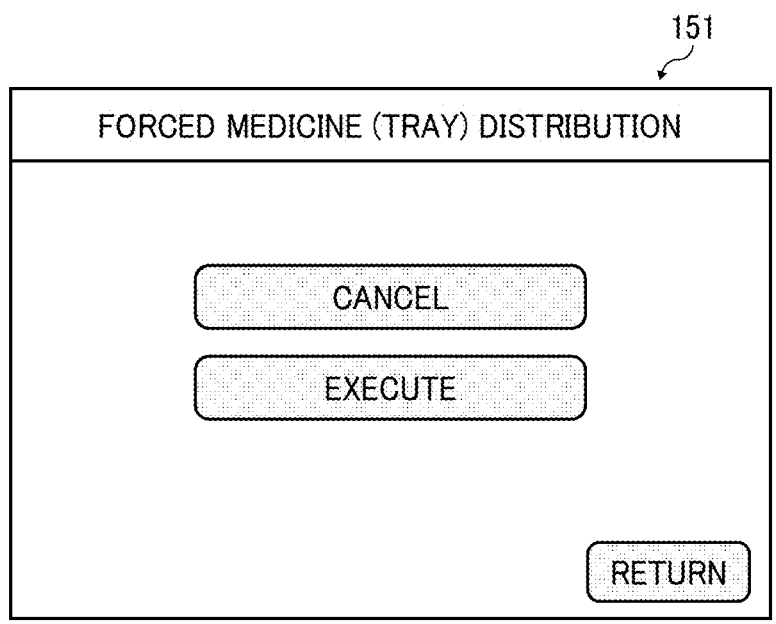
FIG. 42 is a diagram illustrating a "Forced Medicine Distribution (tray)" screen displayed on a touch panel of a medication support apparatus according to an embodiment of the present disclosure.
Figure 47:
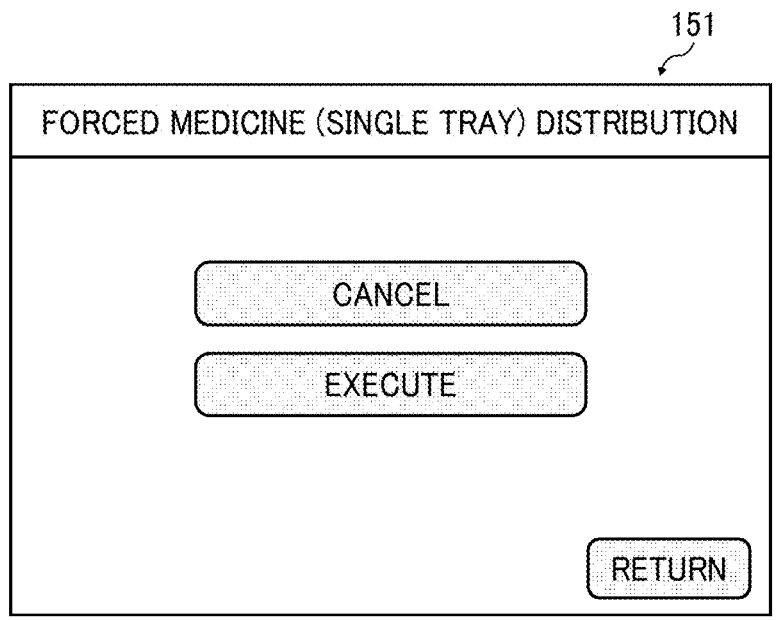
FIG. 47 is a diagram illustrating a "Forced Medicine Distribution (Single tray)" screen displayed on a touch panel of a medication support apparatus according to an embodiment of the present disclosure.

Some medicines are taken depending on the resident's condition of the day. Medication timing of such a medicine may not be necessarily the same timing (before and after a meal) as the medication timing for other residents. Further, there is a possibility that the medicine taken out from the pack is damaged (dropped) by mistake during medication assistance. Therefore, having an operation mode in which a specific pack is taken out from the container and transferred to the medicine distribution tray according to an instruction (taking out processing is performed by the medication support apparatus or the control system) of a user (staff or the like) allows to deliver a necessary medicine to a resident (see FIGS. 40 and 43 to 45 described later). Further, the place to which the pack is finally moved is not limited to the medicine distribution tray, and the take-out port 121 may be provided in the medication support apparatus 200A and the pack 2 is received from the take-out port 121 (FIGS. 40, 46, and 47). Thus, the medicine distribution tray in the medication support apparatus 200A is not wastefully consumed, and the medicine distribution tray can be prevented from being left behind when a small number of packs remains.

FIG. 40 illustrates a screen when a medicine distribution tray is created at an arbitrary timing (the title display is described as "FORCED MEDICINE DISTRIBUTION"). In FIG. 40, three types of buttons are prepared to carry out the normal medicine distribution operation of the medicine distribution tray for a plurality of medicine takers: a "MEDICINE DISTRIBUTION TRAY" button, a "SINGLE UNIT (TRAY)" button for additionally distributing medicine to empty compartments of the medicine distribution tray, and a "SINGLE UNIT (PACK)" button for distributing medicine to the pack tray 120 without passing through the medicine distribution tray. As illustrated in FIG. 41, when the medicine distribution tray to be forcibly taken out is selected, and "EXECUTE" is selected in FIG. 42, the medicine distribution operation in the medication support apparatus 200A is executed. Thus, the medicine distribution tray is taken out and the medicine distribution tray can be received outside the set time. Accordingly, the medication can be prepared in advance.

Figure 44:
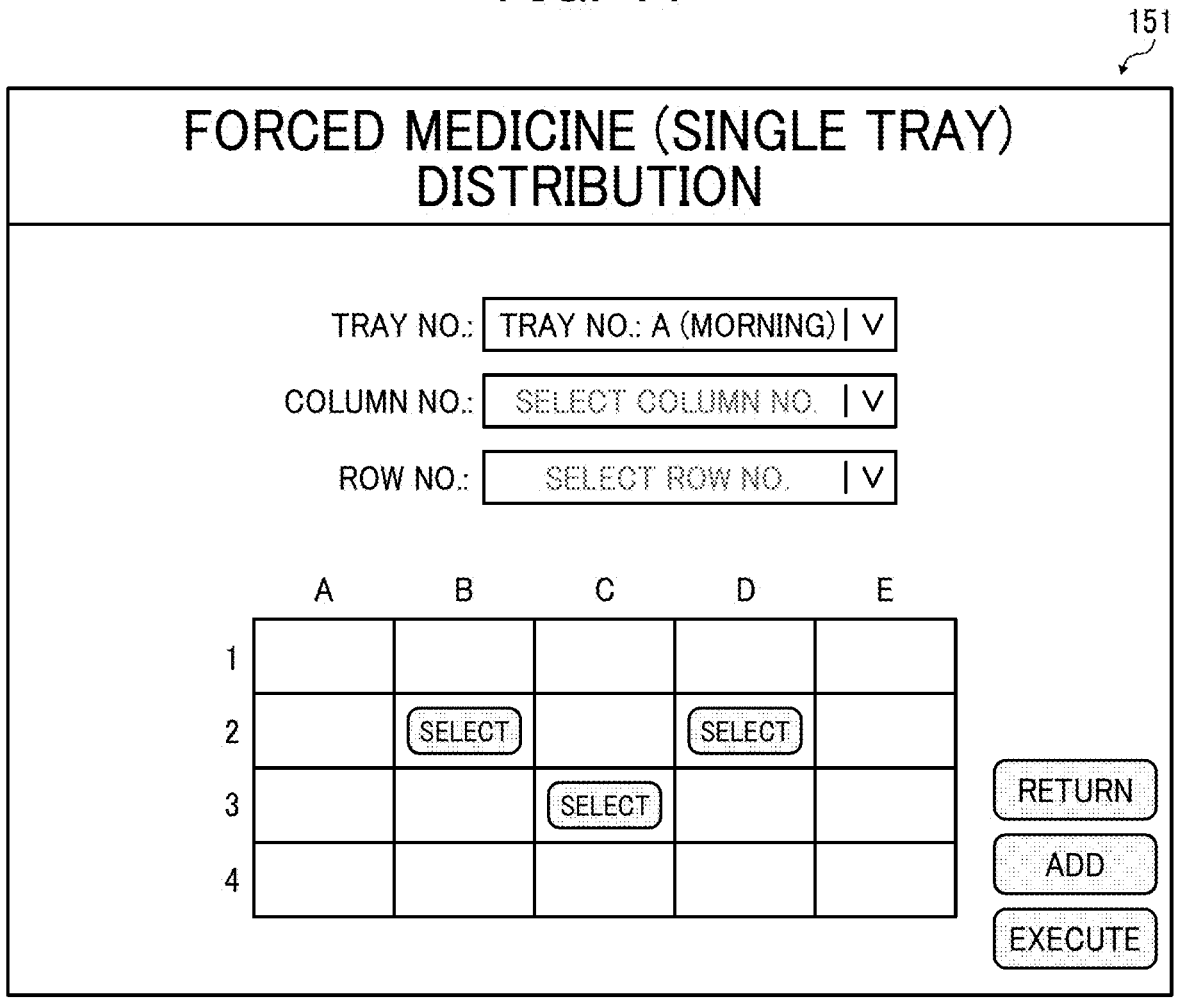
FIG. 44 is a diagram illustrating a "Forced Medicine Distribution (Single tray)" screen displayed on a touch panel of a medication support apparatus according to an embodiment of the present disclosure.
Figure 45:
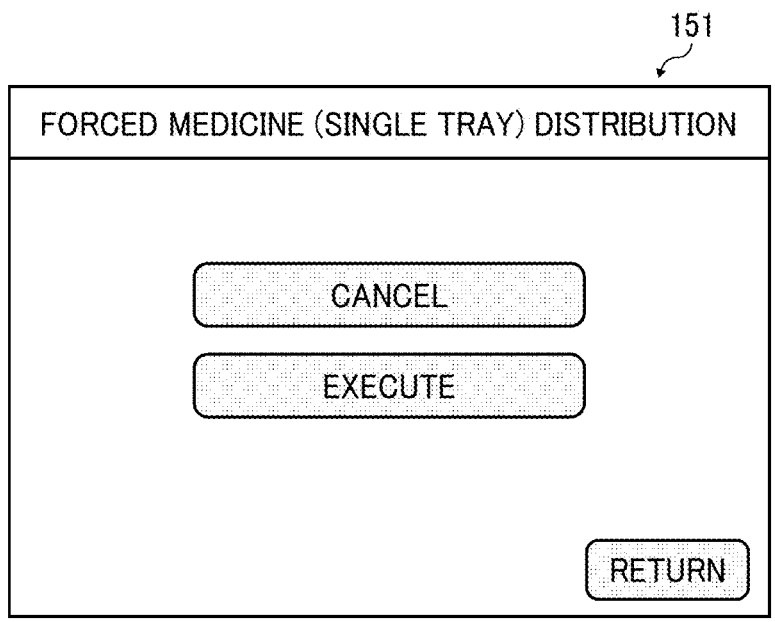
FIG. 45 is a diagram illustrating a "Forced Medicine Distribution (Single tray)" screen displayed on a touch panel of a medication support apparatus according to an embodiment of the present disclosure.
Figure 48:
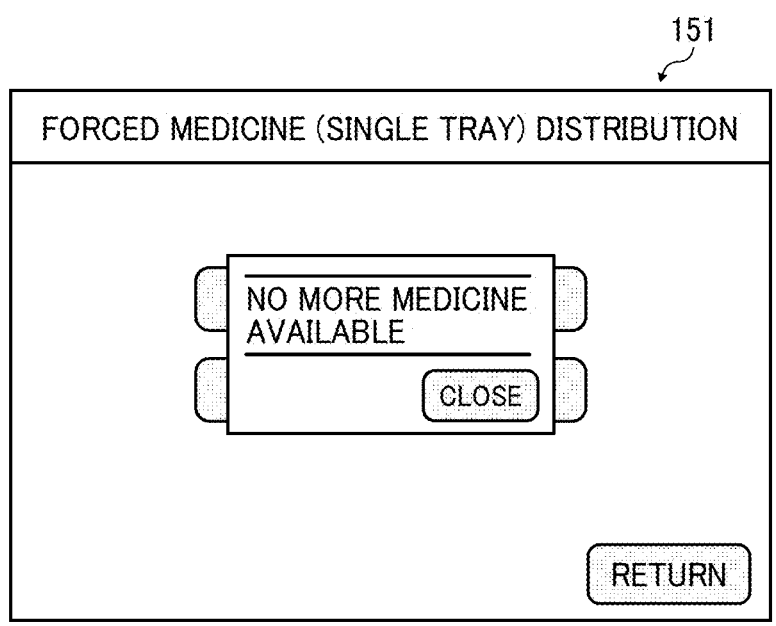
FIG. 48 is a diagram illustrating a "Forced Medicine Distribution (Single tray)" screen displayed on a touch panel of a medication support apparatus according to an embodiment of the present disclosure.

With the "SINGLE UNIT (TRAY)" button, for example, when a medicine is required in advance for the convenience of the resident (temporarily away from home or temporarily coming home), the medicine is selected on the screen of FIG. 43, and an empty place of the medicine distribution tray is selected on the screen of FIG. 44. Thus, the medicine can be taken out from the medicine taking support device. In addition to the above situation, the "single unit (take-out port)" may be taken out temporarily when the medicine is broken during administration (including the case in which the medicine is dropped on the floor and removed), and when the target medicine is selected on the screen of FIG. 46 and "execute" is selected on the screen of FIG. 47, the operation of discharging the medicine to the pack tray 120 is performed and the medicine can be received. However, when there is no remaining amount of medicine (or when there is only a small amount of medicine), these operations cannot be performed, and an execution error, "NO MEDICINE AVAILABLE" is displayed (see FIG. 48).

Figure 49:
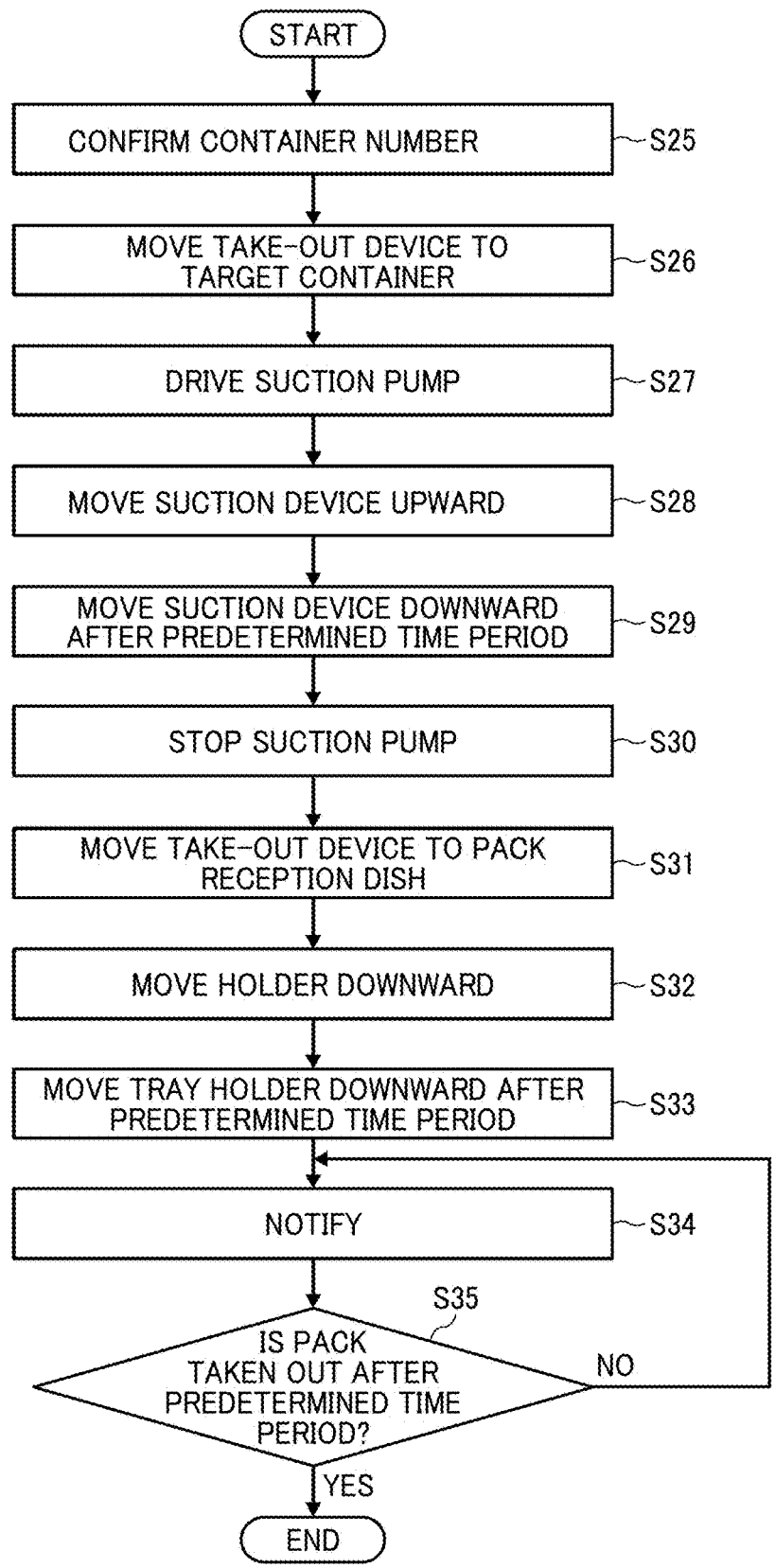
FIG. 49 is a flowchart illustrating an operation flow according to the variation of FIG. 39.

The operation flow according to the variation is supplemented with reference to FIG. 49. FIG. 49 is a flowchart of an operation flow according to the variation. In step S25 of FIG. 49, the number of the container 10 storing the pack 2 to be distributed is confirmed. Next, the take-out device 50 is moved to the target container 10 by the transfer operation of the transfer device 90 (step S26). Next, the suction-device vertical movement motor 60 is driven while driving the suction pumps 48 to move the suction device 51 upward (step S27 to step S28). After a certain period of time in which the lowermost pack 2 in the container 10 is sucked and held by the suction pad 52, the suction-device vertical movement motor 60 is driven in reverse to move the suction device 51 downward. Thereafter, the suction pumps 48 are stopped (step S29 to step S30).

Next, the take-out device 50 is moved to the position of the pack tray 120 by the transfer operation of the transfer device 90. When the take-out device 50 moves to the position of the target pack tray 120, the holder vertical movement motor 69 is driven to move the holder 61 downward (step S31 to step S32). After a certain period of time required for the holder 61 to move downward and the pack 2 in the holding tray 62 to be inserted into and delivered to a predetermined position of the pack tray 120, the holder vertical movement motor 69 is driven in reverse to move the holder 61 upward (step S33). Then, when there is no remaining amount of medicine (or when there is a small amount of medicine), these operations cannot be performed. Thus, this is notified (step S34). It is checked whether the pack 2 in the pack tray 120 has been taken out after the lapse of a fixed time, and when the pack 2 is taken out, a series of operations ends. When the pack 2 in the pack tray 120 is not taken out, the process returns to the step S34 and the notification operation is performed (step S35).

The following aspects and effects are substantially described in the above embodiments, examples, variations, and the like. That is, according to Aspect 1, a medication support apparatus such as the medication support apparatus 200 includes a container such as the container 10 to store one-dose packages of medicines such as the packs 2 in which one dose of medicines such as the drug 3 is packaged, a medicine distribution member such as the medicine distribution tray 30 including a plurality of partitions such as the partitions 31 in which the one-dosage packages of medicines are separately disposed, a port such as the first port 41 to the fourth port 44 through which the medicine distribution member enters and exits the medication support apparatus, a take-out device such as the take-out device 50 to take out a specific one of the one-dose package of medicines from the container 10, and a transfer device such as the transfer device 90 to transfer the specific one of the one-dose package of medicines taken out from the container 10. The one-dose packages of medicines are placed at predetermined positions partitioned by the plurality of partitions in the medicine distribution member.

With such a configuration, according to Aspect 1, the time and effort required for medicine takers or medication supporters can be reduced.

According to Aspect 2, the predetermined positions in the medicine distribution member are allocated to different medicine takers. With such a configuration, according to Aspect 2, the predetermined positions in the medicine distribution member are allocated to different medicine takers. Accordingly, the positions in the medicine distribution member allocated to respective medicine takers do not change day by day. Thus, workload of a medication supporter such as a staff member in a care facility or the like can be reduced.

According to Aspect 3, the predetermined positions in the medicine distribution member are allocated for different medication timings. With such a configuration, according to Aspect 3, the predetermined positions in the medicine distribution member are allocated to respective medication timing, such as morning, noontime, evening, and bedtime. Thus, performing medication at a wrong timing can be prevented.

According to Aspect 4, in Aspect 1, the predetermined positions in the medicine distribution member are allocated in the order of medication. With such a configuration, according to Aspect 4, in a care facility, a medical facility, or the like in which the order of medication is determined in advance, one-dose packages of medicines are taken for medication in order from an end in the medicine distribution member. Thus, errors of taking wrong medicines can be prevented. In other words, for example, one medicine distribution tray as the medicine distribution member becomes one dedicated medicine distribution tray for each medicine taker.

According to Aspect 5, in any one of Aspect 1 to Aspect 4, a housing such as the subdivision box 34A or the subdivision box 34B which is detachably attached to the medicine distribution member is provided in a space partitioned by the plurality of partitions in the medicine distribution member, and the one-dose package of medicines is placed in the housing. With such a configuration, according to Aspect 5, the housing in which the one-dose package of medicines is placed is taken out and a medication supporter goes to a medicine taker to perform medication assistance. In this manner, carrying the entire medicine distribution member, such as the entire medicine distribution tray, is not required. Further, mistakes of taking wrong medicines and one-dose packages of medicines placed on the medicine distribution tray from being loose and scattered can be prevented.

According to Aspect 6, in any one of Aspect 1 to Aspect 5, a specific one of the one-dose packages of medicines is placed in the medicine distribution member by a specific preset time. With such a configuration, according to Aspect 6, the distribution of the one-dose packages of medicines can be effectively prepared by using the available time.

According to Aspect 7, in any one of Aspect 1 to Aspect 5, a specific one of the one-dose packages of medicines is placed in the medicine distribution member at an arbitrary timing. With such a configuration, according to the Aspect 7, a specific one of the one-dose packages of medicines can be taken out even when urgently needed.

According to Aspect 8, in any one of Aspect 1 to Aspect 7, a take-out port such as the take-out port 121 (see FIG. 39) through which a specific one of the one-dose packages of medicines can be taken out is provided. With such a configuration, according to the Aspect 8, a specific one of the one-dose packages of medicines can be taken out even when urgently needed.

According to Aspect 9, in any one of Aspect 1 to Aspect 8, the take-out device takes out the one-dose packages of medicines stored in the container from a lower side of the container. With such a configuration, according to Aspect 9, the take-out device takes out one of one-dose package of medicines remaining in the container. Thus, the take-out device can take out the one of the one-dose packages of medicines remaining in the container by the same operation regardless of the remaining amount of the one-dose package of medicines in the container.

The above-described embodiments are illustrative and do not limit the present disclosure. Thus, numerous additional variations are possible in light of the above teachings. For example, elements and/or features of different illustrative embodiments may be combined with each other and/or substituted for each other within the scope of the present disclosure. For example, the technical matters described in the above embodiments, examples, variations, and the like may be appropriately combined.

The effects described in the embodiments of this disclosure are listed as most preferable effects derived from this disclosure, and therefore are not intended to limit to the embodiments of the present disclosure.

What is claimed is:
1. A medication support apparatus comprising:
a container configured to store one-dose packages of medicines;
a medicine distribution member including a plurality of partitions configured to separately include the one-dose packages of medicines;
a port through which the medicine distribution member is configured to enter and exit the medication support apparatus;
a take-out device configured to take out a specific one of the one-dose packages of medicines from the container; and
a transfer device configured to transfer the specific one of the one-dose packages of medicines taken out from the container,
wherein the one-dose packages of medicines are configured to be placed at predetermined positions partitioned by the plurality of partitions in the medicine distribution member.

2. The medication support apparatus according to claim 1, wherein the predetermined positions in the medicine distribution member are allocated to different medicine takers.

3. The medication support apparatus according to claim 1, wherein the predetermined positions in the medicine distribution member are allocated to different medication timings.

4. The medication support apparatus according to claim 1, wherein the predetermined positions in the medicine distribution member are allocated in order of medication.

5. The medication support apparatus according to claim 1, further comprising a housing detachably attached to the medicine distribution member in a space partitioned by the plurality of partitions in the medicine distribution member, wherein the housing is configured to store one of the one-dose packages of medicines.

6. The medication support apparatus according to claim 1, wherein a specific one of the one-dose packages of medicines is placed in the medicine distribution member by a preset time.

7. The medication support apparatus according to claim 1, wherein a specific one of the one-dose packages of medicines is placed in the medicine distribution member at an arbitrary timing.

8. The medication support apparatus according to claim 1, further comprising a take-out port configured to take out a specific one of the one-dose packages of medicines through the take-out port.

9. The medication support apparatus according to claim 1, wherein the take-out device is configured to take out the one-dose packages of medicines stored in the container from a lower side of the container.

* * * * *